United States Patent [19]
Travis et al.

[11] Patent Number: 5,707,620
[45] Date of Patent: Jan. 13, 1998

[54] **LYSINE-SPECIFIC *PORPHYROMONAS GINGIVALIS* PROTEINASE**

[75] Inventors: James Travis; Jan Stanislaw Potempa; Robert Neil Pike, all of Athens, Ga.

[73] Assignee: University of Georgia Research Foundation, Inc., Athens, Ga.

[21] Appl. No.: 541,902

[22] Filed: Oct. 10, 1995

Related U.S. Application Data

[62] Division of Ser. No. 141,324, Oct. 21, 1993, Pat. No. 5,475,097.
[51] Int. Cl.$^6$ .............................. A61K 38/48; C12N 9/52
[52] U.S. Cl. .......................... 424/94.63; 435/2.1; 435/23; 435/220; 530/388.26; 530/389.4
[58] Field of Search .............................. 435/220, 2.1, 23; 424/94, 63; 530/389.4, 388.26

[56] References Cited

PUBLICATIONS

Scott et al. (1993), "Purification and Characterization of a Potent 70-kDa Thiol Lysyl-proteinase (Lys-gingivain) from *Porphyromonas gingivalis* That Cleaves Kininogens and Fibrinogen", J. Biol. Chem. 268: 7935–7942.
Travis et al. (1993) "Activation of the Complement and Kinin Pathways by Non-Mammalian Proteinases," Abstract, Kinin 93 Brazil, 21.16.
Chen et al. (1991) "Stimulation of Proteinase and Amidase Activities in *Porphyromonas (Bacteroides) gingivalis* by Amino Acids and Dipeptides,"Infect. Immun. 59: 2846–2850.
Birkedal–Hansen et al. (1988) "Characterization of Collagenolytic Activity from Strains of *Bacteroides gingivalis*," J. Periodontal Res. 23: 258–264.
Grenier et al. (1989) "Characterization of Sodium Dodecyl Sulfate-Stable *Bacteroides gingivalis* Proteases by Polyacrylamide Gel Electrophoresis," Infect. Immun. 57: 95–99.
Ono et al. (1987) "Purification and Characterization of a Thiol-protease from *Bacteroides gingivalis* Strain 381"; Oral Micr. Immun. 2:77–81.
Madden et al. (1992), "Expression of *Porphyromonas gingivalis* proteolytic activity in *Escherichia coli*", Oral Micro. Imm. 7: 349–356.
Uitto V.J. (1987) "Human Gingival Proteases. 1: Extraction and Preliminary Characterization of Trypsin–like and Elastase–like Enzymes"; J. Periodontal Res. 22:58–63.
Sorsa et al. (1987) "A Trypsin–like Protease from *Bacteroides Gingivalis*; Partial Purification and Characterization"; J. Periodont Res. 22:375–380.
Hinode et al. (1992) "Genaration of Plasma Kinin by Three Types of Protease Isolated from *Porphyromonas gingivalis* 381," Archs Oral Biol. 10 (37):859–861.
Bourgeau et al. (1992) "Cloning, expression and sequencing of a protease gene (tpr) from *Porphyromonas gingivalis* W83 in *Escherichia coli*," Infect. Immun. 60:3186–3192.
Scott, C.F., et al. (1993) J Biol Chem. 268(11), 7935–7942.
Fujimura, S., et al. (1993) FEMS Microbiol. Letts. 113, 113–138.
Pike, R., et al. (1994) J. Biol. Chem. 269(1), 408–411.
Wingrove, J.A. (1992) J. Biol. Chem. 267(26), 18902–18907.
Chen, Z., et al. (1992) J. Biol. Chem. 267(26) 18896–18901.

*Primary Examiner*—Charles L. Patterson, Jr.
*Attorney, Agent, or Firm*—Greenlee, Winner and Sullivan, P.C.

[57] ABSTRACT

Provide herein is a substantially pure Lys-gingipain complex preparation, Lys-gingipain being characterized as having an apparent molecular mass of 105 kDa as estimated by sodium dodecyl sulfate polyacrylamide gel electrophoresis, where sample is prepared without boiling, said Lys-gingipain having amidolytic and proteolytic activity for cleavage after lysine residues and having no amidolytic and/or proteolytic activity for cleavage after arginine residues, wherein the amidolytic and/or proteolytic activity is inhibited by TLCK, cysteine protease group-specific inhibitors including iodoacetamide and iodoacetic acid, wherein the amidolytic and/or proteolytic activity of said Lys-gingipain is not sensitive to inhibition by leupeptin, antipain, trans-epoxysuccinyl-L-leucylamido-(4-guanidino)butane, serine protease group-specific inhibitors including diisopropylfluorophosphate and phenylmethyl sulfonylfluoride, and antibodies specific for the Lys-gingipain protein complex and its catalytic component, methods for preparation. As specifically exemplified, a Lys-gingipain protein complex is purified from *Porphyromonas gingivalis* H66, and the 60 kDa catalytic component of the Lys-gingipain protein complex has an amino acid sequence as given in SEQ ID NO:14 from amino acid 1 through amino acid 509. Also provided are nucleic acid sequences encoding this catalytic protein. The nucleotide coding sequence of the 60 kDa catalytic component of the Lys-gingipain protein complex is given in SEQ ID NO:13, from nucleotide 1336 through nucleotide 2863. The Lys-gingipain complex also comprises a hemagglutinin component identified by an N-terminal amino acid sequence as given in SEQ ID NO:14, amino acids 510–714.

18 Claims, 9 Drawing Sheets

LYSINE-SPECIFIC PORPHYROMONAS GINGIVALIS PROTEINASE

CROSS REFERENCE TO RELATED APPLICATION

The present application is a divisional application of U.S. patent application Ser. No. 08/141,324, filed Oct. 21, 1993, now U.S. Pat. No. 5,475,097.

This invention was made, in part, with funding from the National Institutes of Health (Grant DE 09761). The United States Government may have certain rights in this invention.

FIELD OF THE INVENTION

The field of this invention is bacterial proteases, more particularly those of *Porphyromonas gingivalis*, most particularly the lysine-specific proteases collectively termed Lys-gingipain herein.

BACKGROUND OF THE INVENTION

*Porphyromonas gingivalis* (formerly *Bacteroides gingivalis*) is an obligately anaerobic bacterium which is implicated in periodontal disease. *P. gingivalis* produces proteolytic enzymes in relatively large quantities; these proteinases are recognized as important virulence factors [Smalley et al. (1989) *Oral Microbiol. Immun.* 4, 178–179; Marsh et al. (1989) *FEMS Microbiol, Lett.* 59, 181–186; Grenier and Mayrand (1987) *J. Clin. Microbiol,* 25, 738–740]. A number of physiologically significant proteins, including collagen [Birkedal-Hansen et al. (1988) *J. Periodontal Res.* 23, 258–264; Sundquist et al. (1987) *J. Periodontal Res.* 22, 300–306]; fibronectin [Wikstrom and Linde (1986) *Infect. Immun.* 51, 707–711; Uitto et al. (1989) *Infect. Immun.* 57, 213–218]; immunoglobulins [Kilian, M. (1981) *J. Infect. Immun.* 34, 757–765; Sundqvist et al. (1985) *J. Med. Microbiol,* 19, 85–94; Sato et al. (1987) *Arch. Oral Biol.* 32, 235–238]; complement factors C3, C4, C5, and B [Sundqvist, et al. 1985) supra; Schenkein, H. A. (1988) *J. Periodontal Res.* 23, 187–192]; lysozyme [Otsuka et al. (1987) *J. Periodontal Res.* 22, 491–498]; iron-binding proteins [Carlsson et al. (1984) *J. Med. Microbiol,* 18, 39–46]; plasma proteinase inhibitors [Carlsson et al. (1984) *Infect. Immun.* 43, 644–648; Herrmann et al. (1985) *Scand. J. Dent. Res.* 93, 153–157]; fibrin and fibrinogen [Wikstrom et al. (1983) *J. Clin. Microbiol.* 17, 759–767; Lantz et al. (1986) *Infect. Immun.* 54, 654–658]; and key factors of the plasma coagulation cascade system [Nilsson et al. (1985) *Infect. Immun.* 50, 467–471], are hydrolyzed by proteinases from this microorganism. Such broad proteolytic activity may play a major role in the evasion of host defense mechanisms and the destruction of gingival connective tissue associated with progressive periodontitis [Saglie et al. (1988) *J. Periodontol.* 59, 259–265].

Progressive periodontitis is characterized by acute tissue degradation promoted by collagen digestion and a vigorous inflammatory response characterized by excessive neutrophil infiltration [White and Maynard (1981) *J. Periodontal Res.* 16, 259–265]. Gingival crevicular fluid accumulates in periodontitis as gingival tissue erosion progresses at the foci of the infection, and numerous plasma proteins are exposed to proteinases expressed by the bacteria at the injury site. It was speculated that neutrophils may have been recruited to the gingiva, in part, by the humoral chemotactic factor C5a. The complement components C3 and C5 are activated by complex plasma proteases with "trypsin-like" specificities called convertases [Muller-Eberhard (1988) *Ann. Rev. Biochem.* 57, 321–347]. The human plasma convertases cleave the α-chains of C3 and C5 at a specific site generating biologically active factors known as anaphylatoxins (i.e. C3a and C5a). The anaphylatoxins are potent proinflammatory factors exhibiting chemotactic and/or spasmogenic activities as well as promoting increased vascular permeability. The larger products from C3 and C5 cleavage (i.e. C3b and C5b) participate in functions including complement cascade activation, opsinization, and lytic complex formation.

There are conflicting data as to the number and types of proteinases produced by *P. gingivalis*. In the past, proteolytic activities of *P. gingivalis* were classified into two groups; those enzymes which specifically degraded collagen and the general "trypsin-like" proteinases which appeared to be responsible for other proteolytic activity. Trypsin (and trypsin-like proteases) cleaves after arginine or lysine in the substrates [See, e.g. Lehninger A. L. (1982), *Principles of Biochemistry*, Worth Publishing, Inc., New York]. An Arg-specific proteinase described in Chen et al. (1992), *J. Biol. Chem.* 267, 18896–18901 differs in that it is specific for cleavage after only arginine, with no activity for cleavage after lysine residues.

More recently, Birkedal-Hansen et al. [Birkedal-Hansen, et al. (1988) supra.] performed a systematic analysis of the effect of six classes of proteinase inhibitors on Porphyromonas collagenolytic activity which strongly suggested that all proteinases from this organism are dependent on free cysteine groups and metal ions, as indicated by inhibition by thiol-blocking reagents and metal chelators. On the other hand, Grenier et al. [Grenier et al. (1989) *Infect Immun.* 57, 95–99] identified at least eight proteolytic enzymes with molecular masses in the range of 29–110 kDa. Two of these appeared to be serine proteinases with glycyl-prolyl peptidase activity, one of which appears to be about 29 kDa [Grenier and McBride (1987) *Infect. Immun.* 55, 3131–3136].

Many *P. gingivalis* proteolytic enzymes were shown to be activated by cysteine and to hydrolyze the synthetic substrate Benzoyl-L-Arginyl-p-Nitroanilide. Whether these represent distinct proteolytic enzymes or autocatalytic products of a single proteinase remains to be established. Although many attempts have been made to separate one of these trypsin-like proteinases [Otsuka, et al. (1987) supra.; Ono et al. (1987) *Oral Microbiol. Immunol.* 2, 77–81; Fujimura and Nakamura (1987) *Infect. Immun.* 55, 716–720; Suido et al. (1987) *J. Periodontal Res.* 22, 412–418; Tsutsui et al. (1987) *Infect. Immun.* 55, 420–427; Uitto, V. J. (1987) *J. Periodontal Res.* 22, 58–63; Sorsa et al. (1987) *J. Periodontal Res.* 22, 375–380] until now none has been purified sufficiently for rigorous biochemical and enzymological characterization. In this application, a thiol-activated, lysine-specific proteinase of *P. gingivalis*, which has been purified to apparent homogeneity for the first time, is described and termed lys-gingipain herein.

There is a need in the art for purified Lys-gingipain, for example, as antigen for preparing antibodies specific to this protein or for vaccines useful in protection against periodontal disease, and for studies to identify inhibitors of this enzyme.

SUMMARY OF THE INVENTION

An object of the present invention is to provide a proteinase preparation comprising a substantially pure high molecular weight Lys-gingipain, termed Lys-gingipain-1 herein, said gingipain-1 having an apparent molecular mass of 105 kDa as estimated by sodium dodecyl sulfate polyacrylamide gel electrophoresis (without boiling of samples) or as estimated by gel filtration chromatography, said Lys-gingipain-1 having amidolytic and proteolytic activity for cleavage after lysine residues and having no amidolytic and/or proteolytic activity for cleavage after arginine residues, wherein the amidolytic and/or proteolytic activity is inhibited by cysteine protease group-specific inhibitors including iodoacetamide, iodoacetic acid, N-ethylmaleimide, and by Glycyl-glycine, and wherein the amidolytic and/or proteolytic activity of said gingipain-1 is not sensitive to inhibition by EDTA, leupeptin, antipain, E-64, and serine protease group-specific inhibitors including diisopropylfluorophosphate and phenylmethyl sulfonylfluoride. In a specifically exemplified Lys-gingipain complex, the catalytic protein is characterized by an N-terminal amino acid sequence as given in SEQ ID NO:1 (Asp-Val-Tyr-Thr-Asp-His-Gly-Asp-Leu-Tyr-Asn-Thr-Pro-Val-Arg-Met-Leu-Val-Val-Ala-Gly).

As specifically exemplified, the mature, 60 kDa catalytic component of Lys-gingipain protein has a complete deduced amino acid sequence as given in SEQ ID NO:14 from amino acid 1 through amino acid 509.

It is an additional object of the invention to provide a method for the preparation of a substantially pure Lys-gingipain-1 protein. Said substantially pure Lys-gingipain-1 exhibits amidolytic and/or proteolytic activity with specificity for cleavage after lysine, but exhibits no amidolytic and/or proteolytic activity with specificity for cleavage after arginine residues. The purification method exemplified herein comprises the steps of precipitating extracellular protein from cell-free culture supernatant of *Porphyromonas gingivalis* with acetone, fractionating the precipitated proteins by gel filtration, further fractionating by anion exchange chromatography those proteins in the fractions from gel filtration with the highest specific activity for amidolytic activity as measured with Benzoyloxycarbonyl-L-Lysine-p-nitroanilide by affinity chromatography over L-arginyl-agarose. Preferably the *P. gingivalis* used is strain H66, and preferably the culture is grown to early stationary phase. Lys-gingipain can also be purified from cells using appropriate modifications of the foregoing procedures (cells must be disrupted, e.g., by lysis in a French pressure cell). Preferably the gel filtration step is carried out using Sephadex G-150, and the affinity chromatography is carried out using L-arginyl-Sepharose 4B.

It is a further object of this invention to provide recombinant polynucleotides (e.g., a recombinant DNA molecule) comprising a nucleotide sequence encoding a Lys-gingipain protein, preferably having an amino acid sequence as given in SEQ ID NO:14 from amino acid 1 through amino acid 509. As specifically exemplified herein, the nucleotide sequence encoding a mature Lys-gingipain proteolytic component protein is given in SEQ ID NO:13 from nucleotides 1336 through 2862. The skilled artisan will understand that the amino acid sequence of the exemplified gingipain protein can be used to identify and isolate additional, nonexemplified nucleotide sequences which will encode a functional protein of the same amino acid sequence as given in SEQ ID NO:14 from amino acid 1 through amino acid 509 or an amino acid sequence of greater than 90% identity thereto and having equivalent biological activity. The skilled artisan understands that it may be desirable to express the Lys-gingipain as a secreted protein; if so, he knows how to modify the exemplified coding sequence for the "mature" Lys-gingipain 60 kDa catalytic component by adding a nucleotide sequence encoding a signal peptide appropriate to the host in which the sequence is expressed. When it is desired that the sequence encoding an Lys-gingipain protein be expressed, then the skilled artisan will operably link transcription and translational control regulatory sequences to the coding sequences, with the choice of the regulatory sequences being determined by the host in which the coding sequence is to be expressed. With respect to a recombinant DNA molecule carrying a Lys-gingipain coding sequence, the skilled artisan will choose a vector (such as a plasmid or a viral vector) which can be introduced into and which can replicate in the host cell. The host cell can be a bacterium, preferably *Escherichia coli*, or a yeast or mammalian cell.

In another embodiment, recombinant polynucleotides which encode a Lys-gingipain, including, e.g., protein fusions or deletions, as well as expression systems are provided. Expression systems are defined as polynucleotides which, when transformed into an appropriate host cell, can express a proteinase. The recombinant polynucleotides possess a nucleotide sequence which is substantially similar to a natural Lys-gingipain-encoding polynucleotide or a fragment thereof.

The polynucleotides include RNA, cDNA, genomic DNA, synthetic forms, and mixed polymers, both sense and antisense strands, and may be chemically or biochemically modified or contain non-natural or derivatized nucleotide bases. DNA is preferred. Recombinant polynucleotides comprising sequences otherwise not naturally occurring are also provided by this invention, as are alterations of a wild type proteinase sequence, including but not limited to deletion, insertion, substitution of one or more nucleotides or by fusion to other polynucleotide sequences. Nonexemplified sequences encoding a Lysine-specific proteinase having at least about 70%, preferably at least about 80%, and more preferably at least about 90%, homology to an exemplified sequence can be readily isolated using art-known techniques.

The present invention also provides for fusion polypeptides comprising a Lys-gingipain. Homologous polypeptides may be fusions between two or more proteinase sequences or between the sequences of a proteinase and a related protein. Likewise, heterologous fusions may be constructed which would exhibit a combination of properties or activities of the proteins from which they are derived. Fusion partners include but are not limited to immunoglobulins, ubiquitin, bacterial β-galactosidase, trpE, protein A, β-lactamase, alpha amylase, alcohol dehydrogenase and yeast alpha mating factor, [Godowski et al. (1988) *Science*, 241, 812–816]. Fusion proteins will typically be made by recombinant methods but may be chemically synthesized.

Compositions and vaccine preparations comprising substantially purified Lys-gingipain derived from *P. gingivalis* and a suitable carrier therefor are provided. Such vaccines are useful, for example, in immunizing an animal, including humans, against inflammatory response and tissue damage caused by *P. gingivalis* in periodontal disease. The vaccine preparations comprise an immunogenic amount of a proteinase or an immunogenic fragment or subunit thereof. Such vaccines may comprise one or more Lys-gingipain proteinases, or an Lys-gingipain in combination with another protein or other immunogen. Particularly preferred is a vaccine composition comprising the Lys-gingipain complex and High Molecular Weight Arg-gingipain. By "immunogenic amount" is meant an amount capable of eliciting the production of antibodies directed against one or more Lys-gingipains in an individual to which the vaccine has been administered.

*gingivalis* culture supernatant. The acetone fraction was applied to a Sephadex G-150 column (5×115 cm=2260 ml), equilibrated with 20 mM Bis-Tris-HCl, 150 mM NaCl, 5 mM CaCl$_2$, 0.02% (w/v) NAN$_3$, pH 6.8, and the fractionation was carried out at a flow rate of 30 ml/h (1.5 cm/h). Fractions (9 ml) were assayed for amidolytic activity against Bz-L-Arg-pNa (-○-) and Z-L-Lys-pNa (-■-) and for protein content by monitoring A$_{280nm}$(-).

Figure 2:
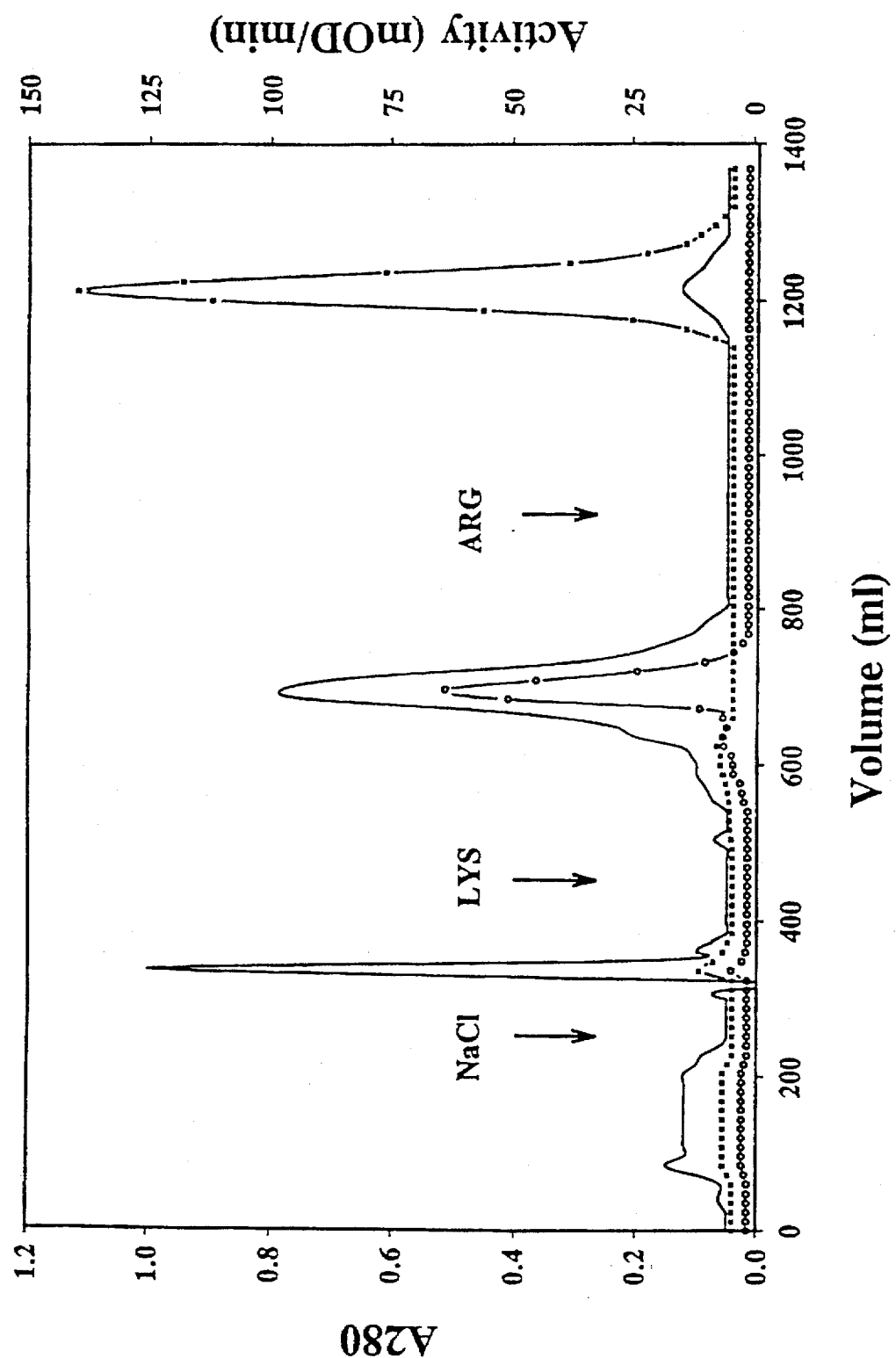

FIG. 2 illustrates chromatography of high MW peak from Sephadex G-150 on L-Arginine-Sepharose. The high MW fraction was applied to L-Arginine-Sepharose (1.5×30 cm=50 ml), equilibrated with 50 mM Tris-HCl, 1 mM CaCl$_2$, 0.02% NAN$_3$, pH 7.4 buffer (Buffer B) at a flow rate of 20 ml/hr (11.3 cm/h), following which the column was washed with two column volumes of Buffer B. A step gradient of 500 mM NaCl was applied, followed by a gradient from 0–750 mM L-lysine in a total volume of 300 ml, and then 100 ml of 750 mM L-lysine. After re-equilibration, a further gradient to 100 mM L-arginine in 300 ml was applied. Fractions (6 ml) were collected and assayed for A$_{280nm}$(-) amidolytic activity (-○-) on Z-L-Lys-pNa; amidolytic activity on Bz-L-Arg-pNa (-■-). ↓ denotes the positions at which gradients were applied.

Figure 3:
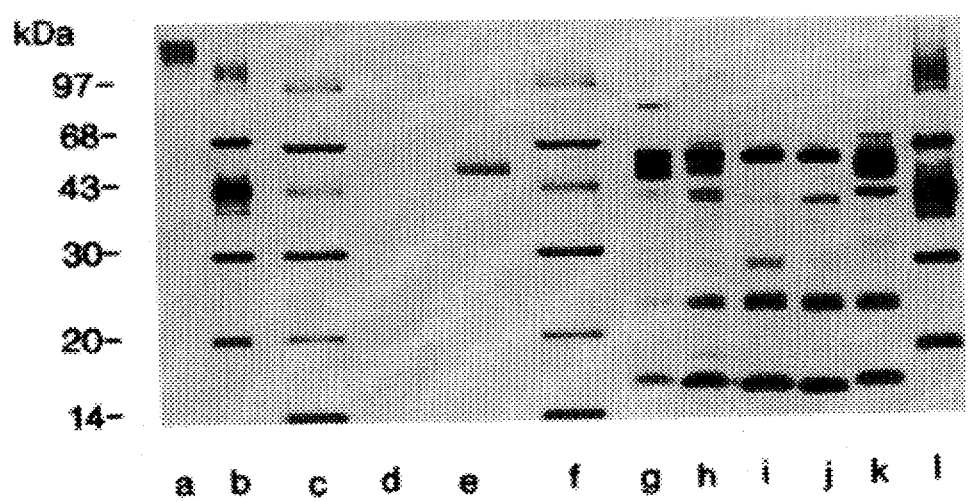

FIG. 3 is a photograph illustrating SDS-PAGE of fractions from the purification of Lys-gingipain and high molecular weight Arg-gingipain. Lanes b), c), f), l) molecular weight markers (phosphorylase b, 97 kDa; bovine serum albumin, 68 kDa; ovalbumin, 43 kDa; carbonic anhydrase, 30 kDa; soybean trypsin inhibitor, 20 kDa; α-lactalbumin, 14 kDa). The following lanes contain unboiled samples: a) purified Lys-gingipain; d) purified high MW Arg-gingipain; e) Arg-gingipain. The following lanes contained boiled samples: g) acetone precipitate of *P. gingivalis* culture fluid; h) peak 1 from Sephadex G-150; i) form 1 of Lys-gingipain from Mono Q; j) form 2 of Lys-gingipain from Mono Q; k) high MW gingipain.

Figure 4:
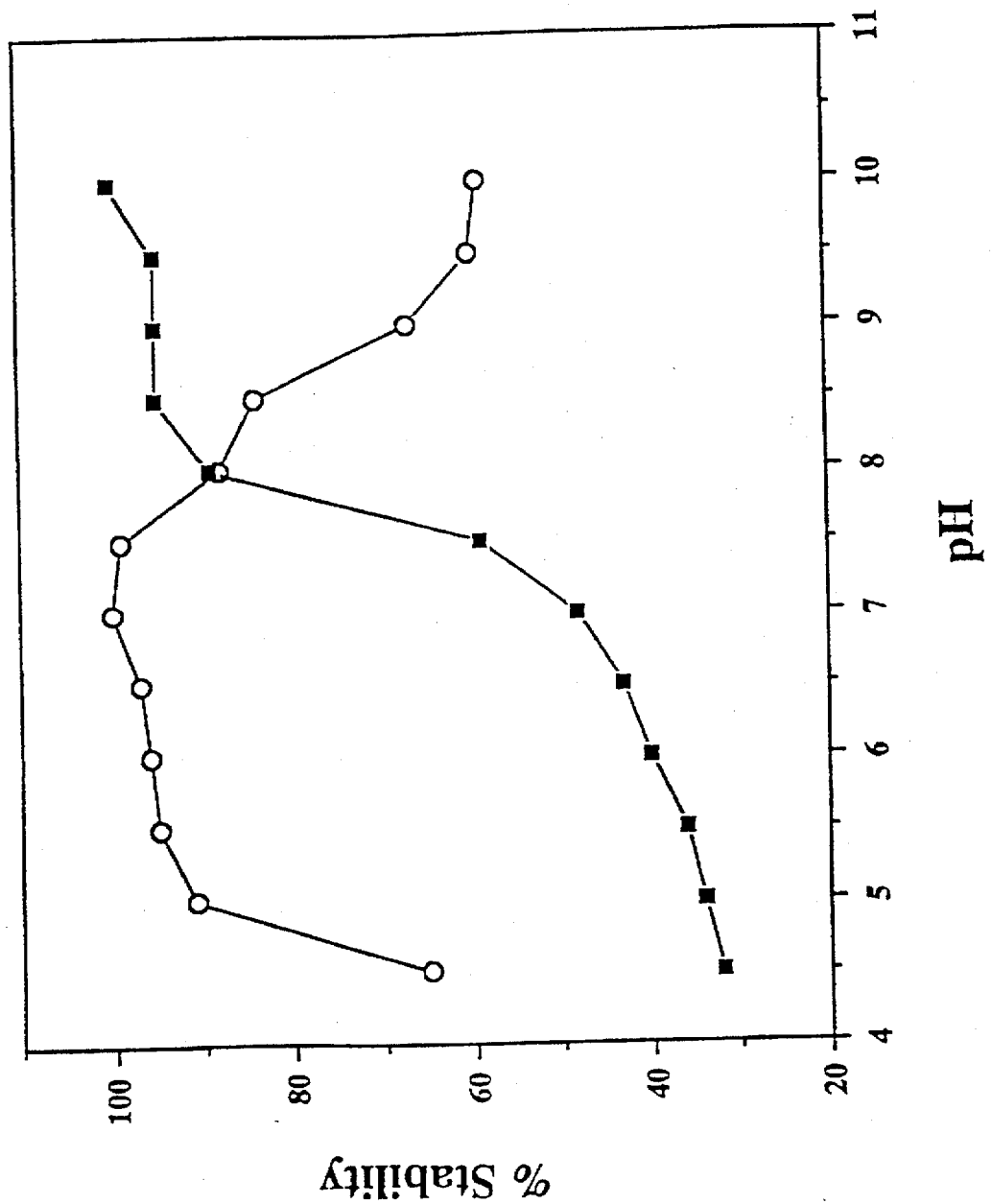

FIG. 4 illustrates pH stability of Lys-gingipain in the presence and absence of cysteine. The enzyme was incubated for 1 h at 37° C. in buffers (as described in [Chen et al. (1991), *Infect. Immun.*, 59, 2846–2850] and then assayed for activity against Z-Lys-pNa in 0.2M Tris-HCl, 0.02% (w/v) NAN$_3$, 10 mM L-cysteine, pH 8.0. ○, Stability in buffer only and ■, stability in buffer containing 10 mM cysteine.

Figure 5:
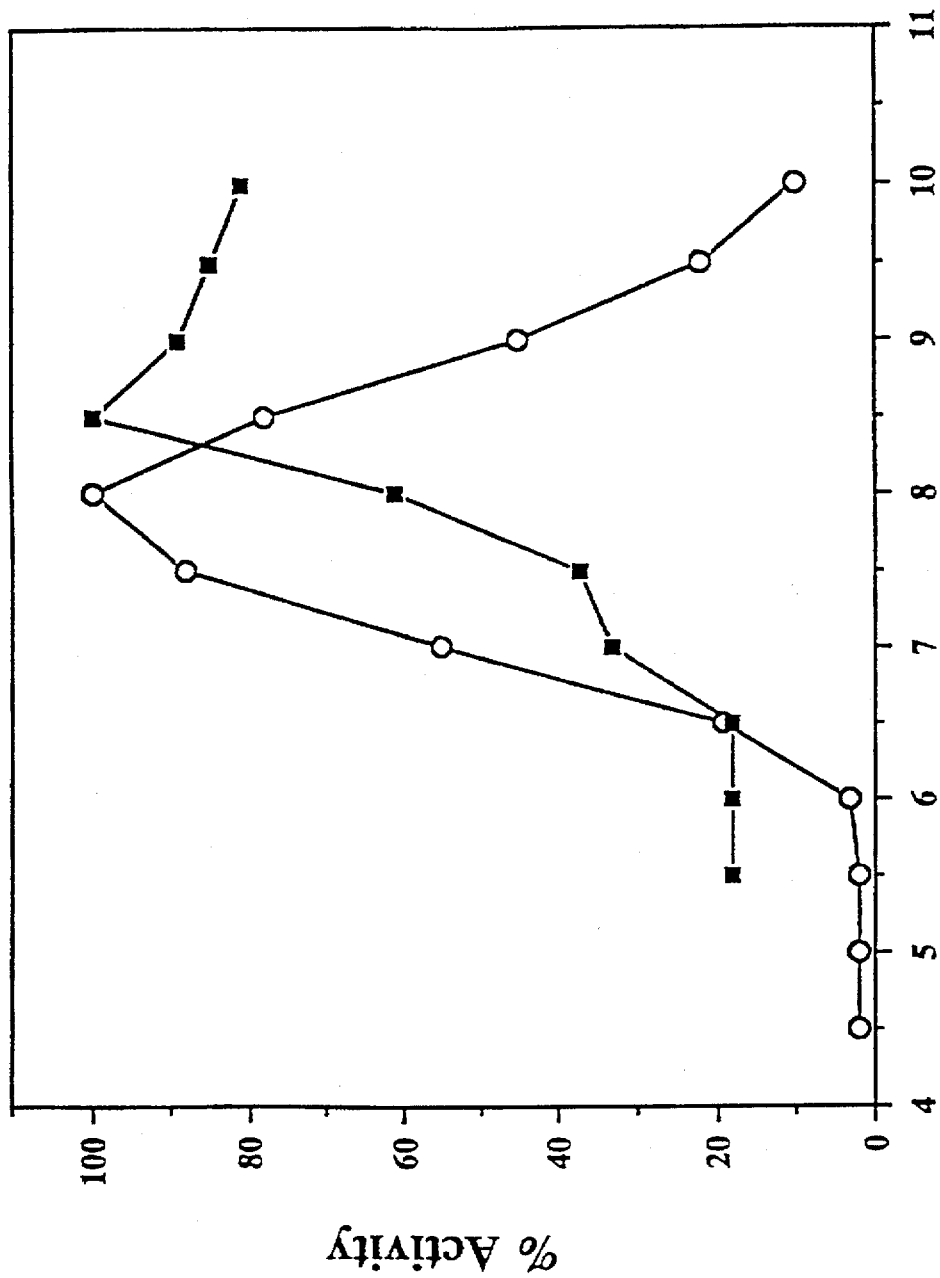

FIG. 5 illustrates the proteolytic and amidolytic activity of Lys-gingipain over a range of Ph values. ○, Activity against Z-L-Lys-pNa over 15 min and ■, activity against azocasein over 1 h.

Figure 6:
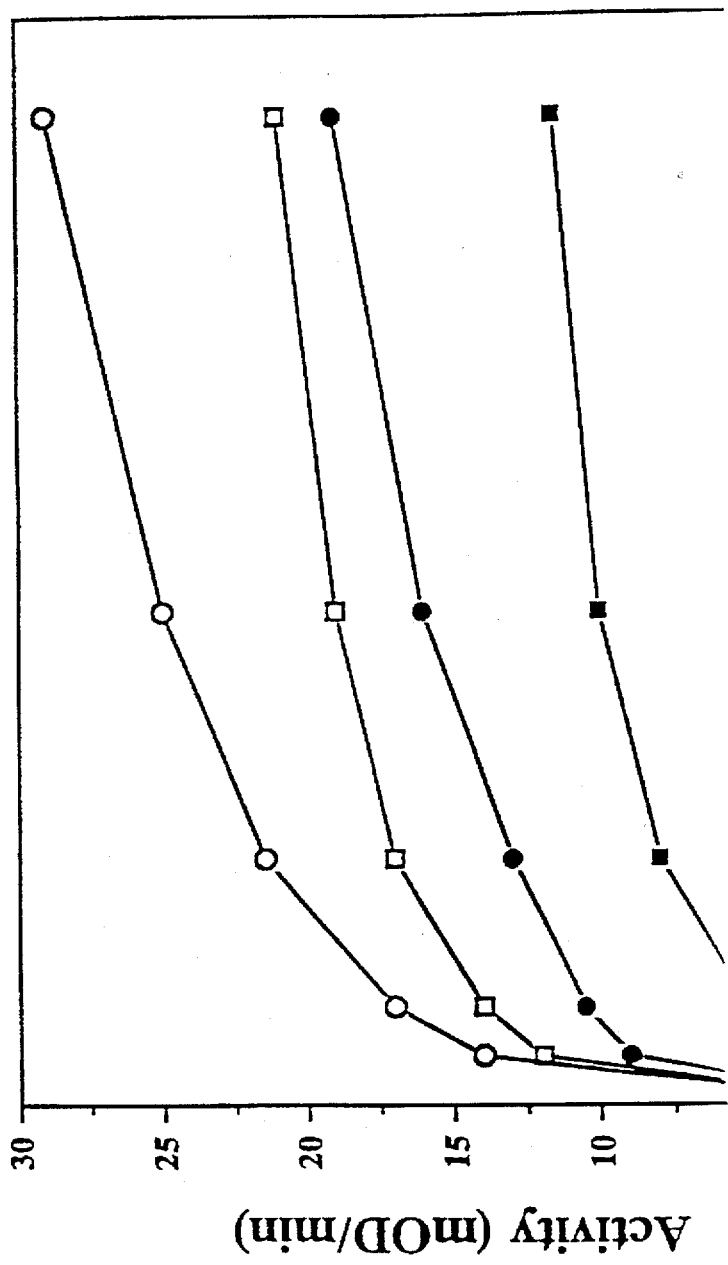

FIG. 6 illustrates the effects of various activators on Lys-gingipain over a range of concentrations. Lys-gingipain was incubated for 5 min at room temperature with the various activators and assayed for hydrolysis of Z-L-Lys-pNa. Activators were β-mercaptoethanol (■), glutathione (●), dithiothreitol (□) and cysteine (○).

Figure 7:
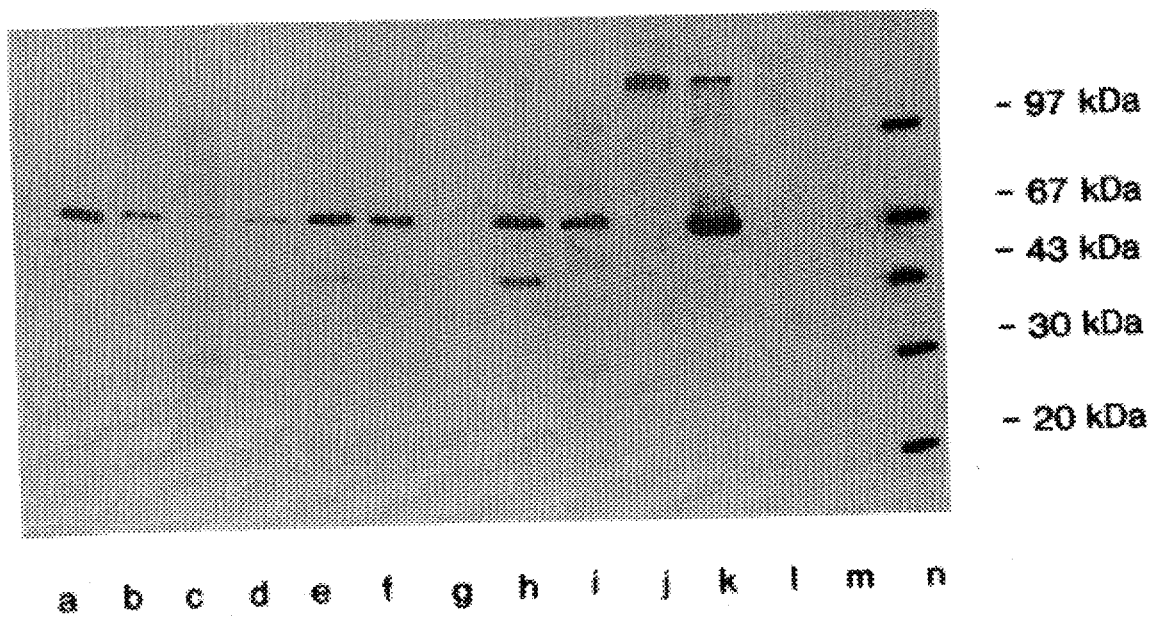

FIG. 7 is a photograph of an immunoblot of fractions from various strains of *P. gingivalis* using anti-Lys-gingipain anti-peptide antibodies. a) Culture fluid, b) vesicles, and c) membranes from strain H66. d) culture fluid, e) vesicles and f) membranes from strain ATCC 33277, g) culture fluid, h) vesicles and i) membranes from strain ATCC 53978, j) Lys-gingipain unboiled, k) Lys-gingipain boiled, l) High MW Arg-gingipain unboiled, m) low MW Arg-gingipain boiled and n) molecular weight standards (weights as marked).

Figure 8:
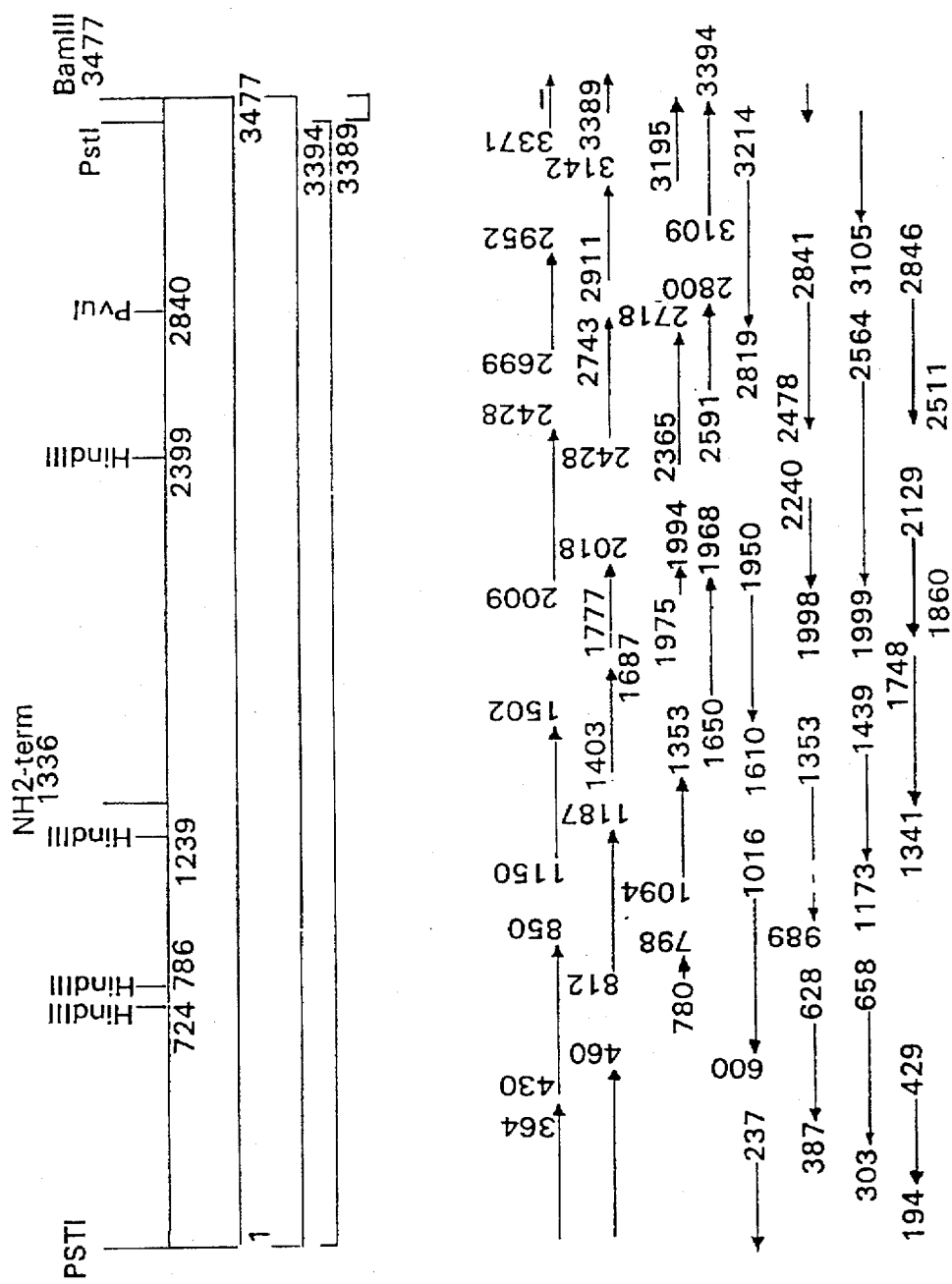

FIG. 8 presents the composite physical map of Lys-gingipain DNA clones. The first codon of the mature Lys-gingipain is indicated. Clones PstI(1)/PstI(3394), PstI(1)/BamHI(3477) and PstI(3389)/BamHI(3477) are represented. The numbers in parenthesis represent the position within the sequenced region. The arrows indicate the extent and direction of sequencing. M13 primers and internal primers were used to sequence both strands of Lys-gingipain DNA as single strand sequencing on PstI/PstI (3394) clone and on PstI(3389)/BamHI(3477) clone in both directions. The junction PstI(3389) was sequenced on double stranded clone PstI(1)/BamHI(3477). Only selected restriction sites are indicated. Numbers are relative to the numbers in Table 7 (SEQ ID NO:13).

Figure 9:
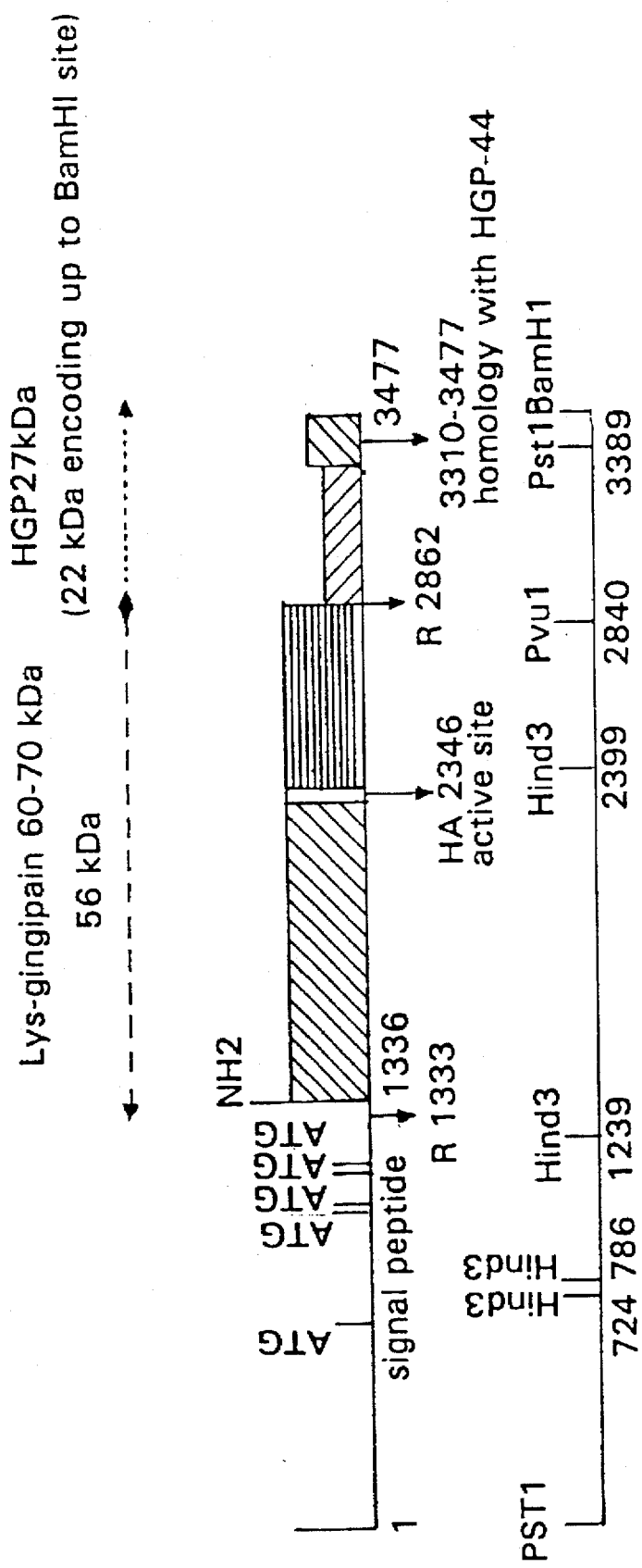

FIG. 9 illustrates the structure of the Lys-gingipain polypeptide coding region within the 3.5 kb PstI/BamHI region. The five ATGs, the codon encoding the amino-terminus, of the mature Lys-gingipain catalytic protein, the two arginine cleaving sites, the potential active site and the 27 kDa hemagglutinin component of the Lys-gingipain complex are shown. Only selected restriction endonuclease recognition sites are indicated.

DETAILED DESCRIPTION OF THE INVENTION

Abbreviations used herein for amino acids are standard in the art: X or Xaa represents an amino acid residue that has not yet been identified but may be any amino acid residue including but not limited to phosphorylated tyrosine, threonine or serine, as well as cysteine or a glycosylated amino acid residue. The abbreviations for amino acid residues as used herein are as follows: A, Ala, alanine; V, Val, valine; L, Leu, leucine; I, Ile, isoleucine; P, Pro, proline; F, Phe, phenylalanine; W, Trp, tryptophan; M, Met, methionine; G, Gly, glycine; S, Ser, serine; T, Thr, threonine; C, Cys, cysteine; Y, Tyr, tyrosine; N, Asn, asparagine; Q, Gln, glutamine; D, Asp, aspartic acid; E, Glu, glutamic acid; K, Lys, lysine; R, Arg, arginine; and H, His, histidine. Other abbreviations used herein include Bz, benzoyl; Cbz, carboxybenzoyl; pNA, p-nitroanilide; benzoyloxycarbonyl; MeO, methoxy; Suc, succinyl; OR, ornithyl; Pip, pipecolyl; SDS, sodium dodecyl sulfate; TLCK, tosyl-L-lysine chloromethyl ketone; TPCK, tosyl-L-phenylalanine chloromethyl ketone; S-2238, D-Phe-Pip-Arg-pNA, S-2222, Bz-Ile-Glu-(γ-OR)-Gly-pNA; S-2288, D-Ile-Pro-Arg-pNA; S-2251, D-Val-Leu-Lys-pNA; Bis-Tris, 2-[bis(2-hydroxyethyl)amino]-2-(hydroxymethyl)-propane-1,3-diol; FPLC, fast protein liquid chromatography; HPLC, high performance liquid chromatography; Tricine, N-[2-hydroxy-1,1-bis(hydroxymethyl) ethyl]glycine; EGTA, [ethylene-bis (oxyethylene-nitrile) tetraacetic acid; EDTA, ethylenediamine-tetraacetic acid; Z-L-Lys-pNa, Z-L-Lysine-p-Nitroanilide; TBS, Tris-buffered saline; PVDF, polyvinylidene difluoride; TFA, trifluoroacetic acid; DTT, dithiothreitol; SRBC, sheep red blood cells; E-64, trans-epoxysuccinyl-L-leucylamide-(4-guanidino) butane.

Lys-gingipain is the term given to a *P. gingivalis* enzyme with specificity for proteolytic and/or amidolytic activity for cleavage of an amide bond in which L-Lysine contributes the carboxyl group. The Lys-gingipain described herein has identifying characteristics of cysteine dependence, inhibition response as described, and molecular weight. Particular forms of Lys-gingipain are distinguished by their apparent molecular masses of the mature proteins (as measured with or without boiling before SDS-PAGE). Lys-gingipains of the present invention have no amidolytic or proteolytic activity for amide bonds in which L-arginine contributes the —COOH moiety.

Lys-gingipain complex is the name given herein to a protein characterized as having a molecular mass of 105 kDa as estimated by gel filtration and components of molecular masses of 60 kDa, 44 or 30, 27 and 17 kDa as measured by SDS-PAGE, having amidolytic and/or proteolytic activity for substrates having L-Lys in the $P_1$ position, i.e. on the N-terminal side of the peptide bond to be hydrolyzed but having no activity against corresponding arginine-containing substrates, being dependent on cysteine (or other thiol groups for full activity), having sensitivity to cysteine protease group-specific inhibitors including iodoacetamide, iodoacetic acid, and N-methylmaleimide, TLCK and FPRCK, but being resistant to inhibition by leupeptin, antipain, E-64, EDTA, and serine protease group-specific inhibitors including diisopropylfluorophosphate and phenylmethyl sulfonylfluoride.

An exemplified Lys-gingipain described herein exists in the native form as a high molecular weight form, termed a Lys-gingipain complex, having an apparent molecular mass of 105 kDa as determined by gel-filtration or SDS-PAGE, without boiling of samples. When boiled before SDS-PAGE, the high molecular weight form appears to dissociate into components of 60 kDa, 43 kDa, 30 kDa, 27 kDa and 17 kDa. The 60 kDa protein is the enzymatically active component of the high molecular weight complex.

The complete amino acid sequence of an exemplified mature 60 kDa catalytic component of the Lys-gingipain complex is given in SEQ ID NO:14, from amino acid 1 through amino acid 509. In nature this protein is produced by the archebacterium Porphyromonas gingivalis; it can be purified from cells or from culture supernatant using the methods provided herein.

As used herein with respect to the Lys-gingipain complex, a substantially pure Lys-gingipain preparation means that there is only one protein band visible after silver-staining an SDS polyacrylamide gel run with the preparation (not boiled), and the only amidolytic and/or proteolytic activities are those with specificity for L-lysine in the $P_1$ position relative to the bond cleaved. A substantially pure high molecular weight Lys-gingipain preparation has only one band (105 kDa) on SDS-PAGE (sample not boiled) or four bands (60 kDa, 43 kDa, 30 kDa, 27 kDa, 17 kDa; sample boiled). No amidolytic or proteolytic activity for substrates with arginine in the $P_1$ position is evident in a substantially pure high molecular weight or Lys-gingipain-2 preparation. Furthermore, a substantially pure preparation of Lys-gingipain has been separated from components with which it occurs in nature. Substantially pure Lys-gingipain is substantially free of naturally associated components when separated from the native contaminants which accompany them in their natural state. Thus, Lys-gingipain that is chemically synthesized or synthesized in a cellular system different from the cell from which it naturally originates will be substantially free from its naturally associated components. Techniques for synthesis of polypeptides are described, for example, in Merrifield (1963) J. Amer. Chem. Soc., 85, 2149–2156.

A chemically synthesized Lys-gingipain protein is considered an "isolated" polypeptide, as is an Lys-gingipain produced as an expression product of an isolated proteinase-encoding polynucleotide which is part of an expression vector (i.e., a "recombinant proteinase"), even if expressed in a homologous cell type.

Recombinant Lys-gingipain can be obtained by culturing host cells transformed with the recombinant polynucleotides comprising nucleotide sequences encoding an Lys-gingipain as described herein under conditions suitable to attain expression of the proteinase-encoding sequence.

Example 1 below describes the purification of Lys-gingipain-1 from P. gingivalis culture supernatant, i.e., from a natural source. Various methods for the isolation of a Lys-gingipain from other biological material, such as from nonexemplified strains of P. gingivalis or from cells transformed with recombinant polynucleotides encoding such proteins, may be accomplished by methods known in the art. Various methods of protein purification are known in the art, including those described, e.g., in Guide to Protein Purification, ed. Deutscher, Vol. 182 of Methods in Enzymology (Academic Press, Inc.: San Diego, 1990) and Scopes, Protein Purification: Principles and Practice (Springer-Verlag: New York, 1982).

The purification of Arg-gingipain-1 (low molecular weight form) has been described in Chen et al. (1992) J. Biol. Chem. 267, 18896–18901. One major problem overcome in the purification of the extracellular proteinases of P. gingivalis involved the removal of the large quantity of hemin and protohemin found to be present in the spent medium after growth of this bacterium.

Figure 1:
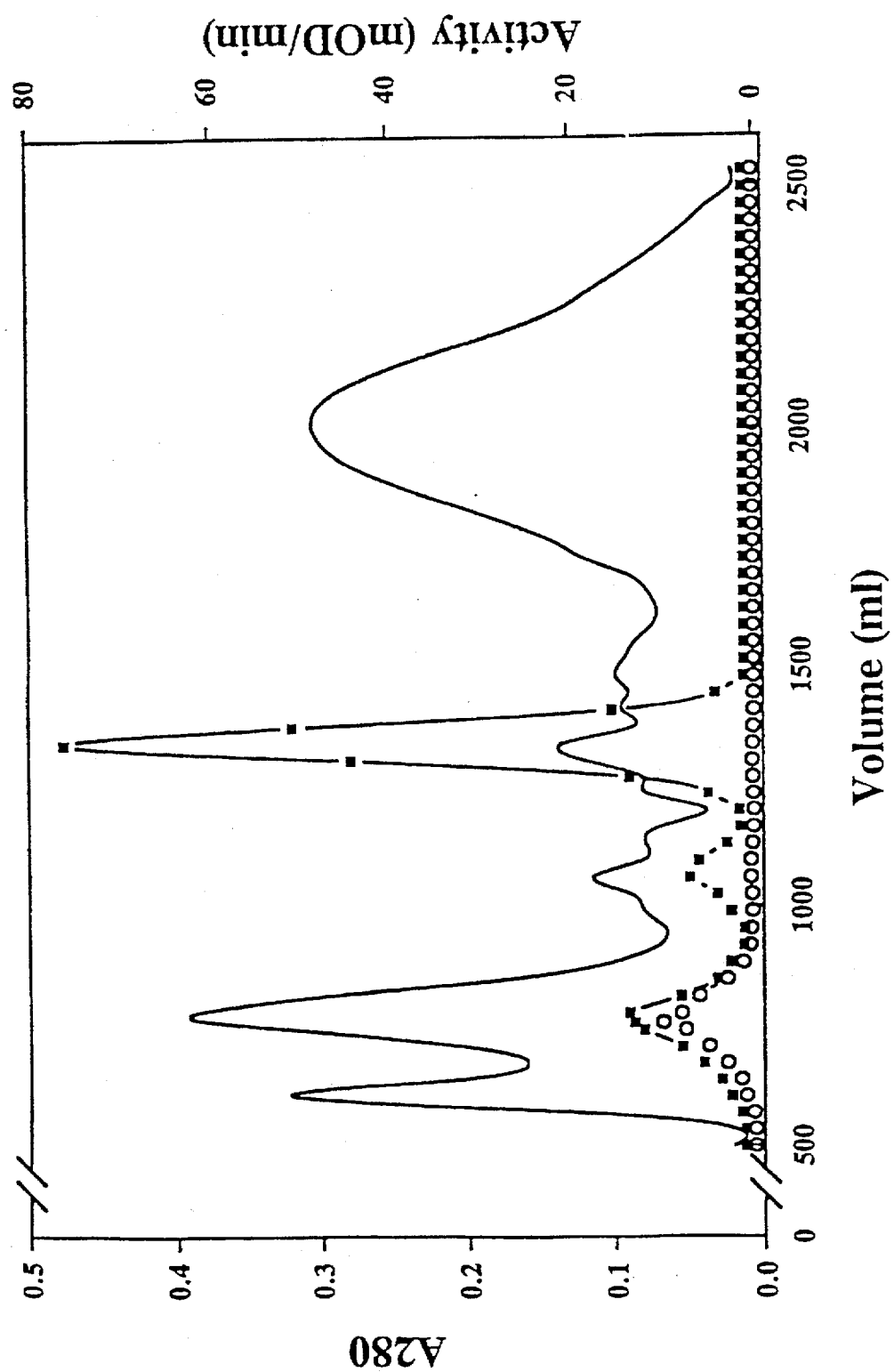
FIG. 1 illustrates gel filtration chromatography over Sephadex G-150 of acetone-precipitated protein from *P.*

Acetone precipitation of culture supernatant was found to give very high yields of the activities cleaving Bz-L-Arg-pNa and Z-L-Lys-pNa, while leaving most of the hemin pigment in solution. Gel filtration chromatography gave a highly reproducible activity profile, yielding three active fractions (FIG. 1), which served as a useful starting point for the purification of Lys-gingipain. The activity for cleaving after lysine residues was primarily found in the highest molecular weight peak, and this fraction was therefore chosen for further study.

Initial results with inhibitors tested on the Bz-L-Arg-pNa and Z-L-Lys-pNa activities indicated that two different enzymes were responsible for the cleavage of these substrates, since the Z-L-Lys-pNa activity was insensitive to EDTA and leupeptin, unlike the Bz-L-Arg-pNa activity. Several modes of chromatography, including anion exchange on a Mono Q column and hydrophobic interaction chromatography on phenyl-superose, were unsuccessful in separating the two activities and therefore the eventual use of L-arginine-sepharose, with differential gradients of lysine and arginine, was vital for their separation. As can be seen in FIG. 2, there was a small amount of unbound protein, and the NaCl step gradient was useful for eluting a large peak of inactive material. The lysine gradient eluted the activity cleaving Z-L-Lys-pNa, and the arginine gradient released that which hydrolyzed Bz-L-Arg-pNa.

Anion exchange chromatography on Mono Q separated the lysine cleaving activity into two predominant forms, and it was also useful as a final purification step for the activity cleaving Bz-L-Arg-pNa. The purification procedure described herein allows the isolation of large quantities of Lys-gingipain, e.g., 20 mg being isolated from about 3 l of culture fluid; 320-fold purification (Table 1).

TABLE 1

Purification of Lys-gingipain

| Fraction | Volume (ml) | Protein (mg) | Total Activity units[a] | Specific units/mg | Purification fold | Yield % |
|---|---|---|---|---|---|---|
| Culture fluid | 2,900 | 36,798 | 206,000 | 5.6 | 1 | 100 |
| Acetone precipitate | 260 | 615 | 181,000 | 294 | 52 | 88 |
| Sephadex G-150 | 60 | 79 | 88,000 | 1114 | 200 | 43 |
| Arginine-Sepharose | 91 | 20 | 36,000 | 1800 | 320 | 18 |

[a]units = mmol/min at 37° C.

SDS-PAGE of Lys-gingipain, without boiling, gave a single band with an estimated molecular mass of 105 kDa. This molecular weight estimate was confirmed for the native enzyme by chromatography on a TSK 3000SW gel filtration column. When the enzymes were boiled before electrophoresis, however, a more complex situation was found. For the Z-L-Lys-pNa activity, major bands were seen at 60 kDa, 27 kDa and 17 kDa in both forms 1 and 2 from the Mono Q column, while minor bands at 30 kDa and 44 kDa seemed specific for forms 1 and 2, respectively, which corresponded to the two active peaks from the Mono Q column.

Inhibition of the enzymes with TLCK prior to boiling before SDS-PAGE, and various other strategies attempted in order to prevent autodigestion, failed to change the electrophoretic patterns. Boiling was necessary for dissociation, as incubation in treatment buffer at temperatures below this point did not release any bands from the high MW position, and the addition of reducing agent had no effect, with or without boiling. Incubation in various detergents, including SDS, Triton X-100, sodium deoxycholate, Nonidet P-40 and CHAPS, for prolonged periods at elevated temperatures, below boiling point, also failed to convert the Lys-gingipain complex to lower MW forms. It was concluded, therefore, that the multiple bands obtained after boiling were due to the dissociation of strong non-covalent bonds between the proteins, rather than due to autodigestion.

The N-terminal sequences were determined for the various bands seen after SDS-PAGE (with boiling) in an effort to determine their identities and/or functions within the complexes (Table 2).

TABLE 2

N-terminal sequences of Lys-gingipain complex components and HGP bands found after SDS-PAGE

| Band | N-Terminal Sequence |
|---|---|
| Lys-gingipain: | |
| 60 kDa | DVYTDHGDLYNTPVRMLVVAG (SEQ ID NO:1) |
| 44,30,27 kDa | ANEAKVVLAADNVWGDNTGYSFLLDA (SEQ ID NO:2) |
| 17 kDa | PQFTEIFRQVDLPAGT (SEQ ID NO:3) |
| High Molecular Weight Arg-gingipain (HGP) | |
| 50 kDa | YTPVEEKQNGRMIVTVAKKYEG (SEQ ID NO:4) |
| 44 kDa | SGQAEIVLEAHDVXNDG (SEQ ID NO:5) |
| 27 kDa | ANEAKVVLAADNVWGDNTGYSFLLDA (SEQ ID NO:2) |
| 17 kDa | PQFTEIFRQVDLPAGT (SEQ ID NO:3) |

The situation is complex for Lys-gingipain in that it was not possible to purify the free 60 kDa enzyme or binding proteins from the culture fluid (initial results indicate the presence of low MW Lys-gingipain activity (60 kDa) in membrane fractions of P. gingivalis H66, but in all fractions the higher MW activity was predominant). By analogy with the high MW Arg-gingipain (HGP), however, since the 27 and 17 kDa bands associated with both activities share the same N-terminal sequence and without wishing to be bound by any theory, it appears that the major 27 and 17 kDa bands combine in the native protein to form a 44 kDa protein, which is the MW of a minor band found in the Lys-gingipain form 2, with the same N-terminal sequence. In this hypothesis the 44 kDa proteins are associated with the major band at 60 kDa to give the overall MW of 105 kDa found by gel filtration and SDS-PAGE, without boiling of the sample for Lys-gingipain. In form 1 of Lys-gingipain there appears to be a minor 30 kDa version of the binding protein, which may be a different cleavage form of the same protein. Since all bands in the lys-gingipain except the 60 kDa one are also found in the Arg-gingipain sample, it is postulated that the 60 kDa band represents the catalytic portion of the Lys-gingipain proteinase.

Table 3 shows the inhibition of Lys-gingipain by common proteinase inhibitors. The lack of inhibition by inhibitors characteristic of the other classes of proteinases, the absolute dependence of the activity on the presence of cysteine, and the inhibition by some common cysteine proteinase inhibitors, indicate, as is known for Arg-gingipain, that Lys-gingipain is a cysteine proteinase. High concentrations of inhibitors such as iodoacetamide are required to inhibit the enzyme, however, indicating that the active-site cysteine group in the Lys-gingipain may be less reactive than in the "classical" papain superfamily of cysteine proteinases. Lys-gingipain differs markedly from Arg-gingipain in that the inhibitors $ZnCl_2$, p-aminobenzamidine, leupeptin, antipain and EDTA failed to inhibit Lys-gingipain even at higher concentrations, while they were effective inhibitors of Arg-gingipain. The compound E-64, which is an effective inhibitor of most cysteine proteinases of the papain family, has previously been shown to inhibit Arg-gingipain, but not in the normal equimolar manner [Chen et al. (1992) supra]. This compound failed to inhibit Lys-gingipain at all, indicating again that it is probably quite different from other cysteine proteinases. TLCK and Phe-Pro-Arg-CK (FPRCK) were effective inhibitors of both enzymes. Glycyl-glycine, which strongly stimulates the hydrolysis of Bz-L-Arg-pNa by Arg-gingipain, was inhibitory towards Lys-gingipain.

TABLE 3

Effect of inhibitors on the amidolytic activity of Lys-gingipain

| Inhibitor | Conc. (mM) | % Activity |
|---|---|---|
| Diisopropylfluorophosphate | 10 | 100 |
| Phenylmethylsulfonyl fluoride | 10 | 100 |
| p-Aminobenzamidine | 10 | 100 |
| Iodoacetamide | 10 | 0 |
|  | 1 | 50 |
| Iodoacetate | 10 | 0 |
|  | 1 | 100 |
| N-Ethylmaleimide | 10 | 0 |
|  | 1 | 100 |
| $ZnCl_2$ | 10 | 100 |
| TLCK | 0.1 | 0 |
| FPRCK | 0.1 | 5 |
| E-64 | 1 | 100 |
| Leupeptin | 0.1 | 100 |
| Antipain | 0.1 | 98 |
| EDTA | 10 | 90 |
| Gly—Gly | 200 | 50 |

Lys-gingipain, in the absence of cysteine, is stable over the pH range from 5–9 over several hours (FIG. 4), but in the presence of cysteine, it loses activity fairly quickly below pH 8. The enzyme (without cysteine) was stable at room temperature and 37° C., and it was denatured at 60° C.

The pH optimum of Lys-gingipain for the hydrolysis of small synthetic substrates was found to be at pH 8.0 (FIG. 5), while with protein substrates, such as azocasein, it was nearer pH 8.5.

Cysteine was the most effective reducing agent for activation of the enzyme, followed by DTT, glutathione and β-mercaptoethanol (FIG. 6). Low levels of cysteine were able to activate the enzyme, but 50 mM was required for full activity. Full activation by cysteine was found after 5 min; however, activity could be detected as soon as 30 sec after an incubation was started. As the cysteine concentration was increased above 50 mM, the enzyme was denatured.

The Km and Vmax values for Lys-gingipain, acting on four commercially available lysine-containing substrates, are given in Table 4.

N-p-tosyl-gly-Pro-Lys-pNa appears to be the best substrate for the enzyme in terms of the ratio of Vmax/Km, followed by D-Val-Phe-Lys-pNa, D-Val-Leu-Lys-pNa and Z-L-Lys-pNa.

TABLE 4

Kinetic constants for the hydrolysis of synthetic substrates by Lys-gingipain

| Substrate | Km(mM) | Vmax (mmol/min) | Vmax/Km |
|---|---|---|---|
| Z—L—Lys—pNa | 0.18 | 40 | 220 |
| HD—Val—Leu—Lys—pNa | 0.2 | 133 | 665 |
| HD—Val—Phe—Lys—pNa | 0.126 | 180 | 1420 |
| N-p-tosyl-Gly—Pro—Lys—pNa | 0.05 | 215 | 4280 |

Lys-gingipain cleaves specifically on the C-terminal side of lysine residues in the various peptides studied (Table 5). Apart from providing evidence of the specificity of the enzyme, the peptides provide a greater variety of amino acids in the $P_2$ position. These studies revealed that Lys-gingipain is not specific for amino acids in positions other than $P_1$, except that it does not hydrolyse a potential substrates when lysine or arginine is in the $P_2$ position. It also does not cleave after a lysine at the N-terminus, and it very slowly hydrolyses bonds after a lysine residue, one amino acid removed from the N-terminus.

TABLE 5

Cleavage of various peptides by Lys-gingipain

| Substrates | Cleavage sites |
|---|---|
| Neurotensin | LYENKPRRPYIL (SEQ ID NO:6) |
| Melittin | GIGAVLKVLTTGLPALISWIKRKREE (SEQ ID NO:7) |
| Adrenocorticotrophic Hormone Fragment 11-24 | KPVGKKRRPVKVYP (SEQ ID NO:8) |
| β- Endorphin | GGFMTSEKSQTPLVTLFKNAIIKNAYKKGE (SEQ ID NO:9) |
| Met-Lys-Bradykinin | MKRPPGFSPEFR (SEQ ID NO:10) |
| Synthetic Peptide 1 | EEISEVKMDAEFRHDSGYEVHHQKLVF (SEQ ID NO:11) |
| Synthetic Peptide 2 | EEISEVDLDAEFRHDSGYEVHHQKLVF (SEQ ID NO:12) |

The specific affinity of the Lys-gingipain for L-arginine-Sepharose was of great interest in comparison to the behavior of lower MW form of this enzyme. High molecular weight Arg-gingipain and crude preparations of low MW Lys-gingipain (60 kDa; from *P. gingivalis* membranes) show very little affinity for this matrix, and thus it appears that the other proteins bound to the enzymatic components in the high molecular weight complexes were mediating this affinity. The activity of hemagglutinins previously isolated from *P. gingivalis* was consistently found to be inhibited by arginine and, to a lesser extent, lysine [Grenier and Mayrand (1987) *Infect. Immun.* 55, 111–117; Inoshita et al. (1986) *Infect. Immun.* 52, 421–427; Okuda et al. (1986) *Infect. Immun.* 54, 659–665]. The hemagglutinating activities of the Lys-gingipain complex and the high molecular weight Arg-gingipain were compared to that of a culture fluid fraction and pure low molecular weight Arg-gingipain fractions. The results (Table 6) clearly show that High MW-Arg-gingipain (HGP) and the Lys-gingipain complex are equally effective as hemagglutinins and that the activity of each is inhibited by arginine and, to a lesser extent, by lysine. The culture fluid also had some hemagglutinating activity, but low MW Arg-gingipain (gingipain-1) was devoid of such activity. The addition of cysteine had no effect on the hemagglutinating activity of any purified fraction, neither did treatment by the irreversible proteinase inhibitor TLCK. Thus, it appears that the proteins associated with the enzymatic components of the Lys-gingipain and High MW-gingipain complexes are most likely hemagglutinins.

TABLE 6

The effect of several compounds on the hemagglutinating titer of *P. gingivalis* fractions

| | Hemagglutinating Titer (μg/ml) | | | |
|---|---|---|---|---|
| Effector | Culture fluid | Lys-gingipain | HGP | Gingipain-1 |
| TBS | 400 | 30 | 30 | NHA* |
| 10 mM cysteine | 400 | 30 | 30 | NHA |
| TLCK | 400 | 30 | 30 | NHA |
| 50 mM arginine | NHA | NHA | NHA | NHA |
| 100 mM lysine | 800 | 125 | 250 | NHA |

*NHA, no hemagglutinating activity.

Further analysis of the high molecular weight fractions containing Lys-specific amidolytic and proteolytic activity reveals that Lys-gingipain catalytic protein (60 kDa) occurs non-covalently bound to proteins of 44 kDa, 30 kDa and 27 kDa, subsequently identified tentatively as hemagglutinin (s), and to a protein of 17 kDa. The N-terminal amino acid sequence of the complexed 44, 30 and 27 kDa proteins was ANEAKVVLAADNVWGDNTGYSFLLDA (SEQ ID NO:2). This latter N-terminal sequence was the same as that of the 27 kDa protein in the high molecular weight Arg-gingipain complex.

As exemplified herein, the Lys-gingipain complex is isolated from the culture fluid of the H66 strain of *P. gingivalis*, which strain is not well characterized in terms of its behavior in in vivo models. Two commercially available strains were therefore used: ATCC 33277, which is non-invasive in in vivo models, and ATCC 53978 (W50), which is highly invasive and even lethal in in vivo models [Genco et al. (1991) *Infect. Immun.* 59, 1255–1263]. The distribution and characteristics of the enzyme in the different strains was studied using a Lys-gingipain-specific antibody in immunoblotting studies. Lys-gingipain, as isolated from H66, occurs as a complex between a catalytic subunit and at least one hemagglutinin subunit, and, therefore, antibodies were not produced to the whole molecule, but rather a peptide from the N-terminus of the 60 kDa catalytic portion of the molecule. Gene sequencing studies revealed that the protein was synthesized as a polyprotein containing both proteinase and hemagglutinin domains, but the anti-peptide antibodies are nevertheless useful for the immunoblotting studies to reveal the different forms of the catalytic component of Lys-gingipain.

Enzyme assays of the various fractions revealed that the ATCC 53978 vesicle fraction had the most activity against the Z-Lys-pNa substrate, and that the enzyme was mainly membrane bound in both the ATCC 33277 and ATCC 53978 strains. The immunoblotting studies confirmed this, in that the culture supernatants of ATCC 53978 and ATCC 33277 had very little of the catalytic 60 kDa band, in contrast to the H66 culture supernatant, which had the strongest band of any of the H66 fractions. The H66 strain produced a very small amount of vesicles, but the 60 kDa band was visible in this fraction. The H66 membrane fraction contained mainly a 32 kDa band which reacted with the antibody. In the ATCC 53978 and ATCC 33277 vesicular and membrane fractions there was a strong 60 kDa band, but only in the ATCC 53978 vesicles did a lower MW band appear with a molecular mass of about 45 kDa. The vesicles from *P. gingivalis* consist of small membrane "blebs" which are continually released by the bacteria and they are thought to be one of the main ways in which the virulence components of the bacteria are transported into tissues etc. [Mayrand and Grenier (1989) *Can. J. Microbiol.* 35, 607–613]. Thus the finding that the invasive ATCC 53978 strain of *P. gingivalis* had greater quantities of a different form of the Lys-gingipain enzyme than the non-invasive ATCC 33277 strain, suggests that this form of Lys-gingipain participates in the invasiveness of the ATCC 53978 strain in some way. The occurrence of this form in the vesicles was also interesting in terms of the putative role of these structures as one of the major components in the pathogenesis caused by this organism.

To test for in vivo biological activity of Lys-gingipain-1, the purified enzyme was injected into guinea pig skin. The Lys-gingipain complex alone did not induce vascular permeability enhancement (VPE), although it did augment the VPE response for Arg-gingipain (low molecular form), with an earlier peak.

Human plasma (but not guinea pig plasma) treated with the Lys-gingipain complex ($3 \times 10^{-7}$ to $10^{-6}$M) induced vascular permeability enhancement in the guinea pig skin assay. Vascular permeability enhancement by Lys-gingipain complex-treated human plasma was increased by addition of 1,10-phenanthroline (kininase inhibitor, chelating agent for Zn ions) to a final concentration of 1 mM and the activity was inhibited by soybean trypsin inhibitor at concentrations which did not affect proteolytic activity. Vascular permeability enhancement by Arg-gingipain-treated plasmas was markedly reduced when plasmas deficient in Hageman factor, prekallikrein or high molecular weight kininogen were used. The Lys-gingipain complex alone did not induce VPE from human plasma deficient in Hageman factor, prekallikrein or high molecular weight kininogen. These results suggest that vascular permeabilizing enhancement by Arg-gingipain-1 and Lys-gingipain occurs via activation of Hageman factor and the subsequent release of bradykinin from high molecular weight kininogen by kallikrein, and that the two gingipains act synergistically. Furthermore, the proteinases induced neutrophil accumulation by intradermal injection, which accumulation was dependent on the proteolytic activities.

The foregoing results demonstrate the participation of Lys-gingipain complex in the inflammatory response in guinea pig animal model.

A *P. gingivalis* enzyme reported to be lysine-specific was isolated from cellular membranes by Scott et al. (1993) *J. Biol. Chem.* 268, 7935–7942. It was characterized as a fibrinogenase and kininogenase, but no specificity studies or $NH_2$-terminal amino acid sequence data were presented therein. However, the current model for bradykinin release from high molecular weight kininogen requires cleavage after both arginine and lysine residues [Halkier et al. (1991) *Mechanisms in Blood Coagulation, Fibrinolysis and the Complement System*, 1st Ed., Cambridge University Press, Great Britain]. The Lys-gingipain of the present invention appears to have no ability to cleave after arginine residues. The Lys-gingipain complex does not appear to affect fibrin or fibrinogen.

The primary structure of the $NH_2$-terminus of Lys-gingipain enzymatically active 60 kDa component was determined by direct amino acid sequencing, as given in SEQ ID NO:1. This information was used to design mixtures of synthetic oligonucleotides primer MK-9-29 (SEQ ID NO:15) coding for amino acids 1–6 and primer MK-10-29 (SEQ ID NO:16) coding for amino acids 16–21 of the mature active 60 kDa protein, these primers were used in PCR on *P. gingivalis* DNA (see Example 5). A single 76-base pair product (P76) resulted. This was cloned into M13mp18 and 19 (NEN Biolabs) and sequenced. Sequence analysis of P76 generates 28 nucleotides from the 60 kDa active component's coding sequence. On the basis of the sequence of P76, another oligonucleotide (lys-1-33; SEQ ID NO:17) corresponding to the coding strand of this partial Lys-gingipain DNA (33-mers) was synthesized in order to screen the λDASH DNA library using a $^{32}$P-labeled lys-1-33 probe. Sequence of Lys-gingipain DNA (nucleotides 1–3477, Table 7, SEQ ID NO:13) was determined by screening the *P. gingivalis* DNA library using $^{32}$P-labeled lys-1-33 probe. A total of $2 \times 10^5$ independent plaques were screened. Seven positive clones were isolated and purified. After extraction and purification, the DNA was analyzed by restriction enzymes. All positive clones had a 3.8 kb BamHI fragment and a 3.4 kb PstI fragment. This result is similar to that obtained by Southern analysis of *P. gingivalis* DNA (Example 5). The 3.8 kb-BamHI fragment and the 3.4 kb-PstI fragment from clone A2 were subsequently cloned into pbluescript SK(−). The 3.4 kb-PstI fragment and the 0.9 Kb-PstI/BamHI 3'end- fragment were subcloned in M13mp18 and 19 and sequenced.

The nucleotide sequence of approximately 3.5 kb encompassed by the 3.4 kb PstI and the 0.9 kb PstI/BamHI fragments is presented in Table 7 (SEQ ID NO:13); this sequence contains 3477 nucleotides.

TABLE 7

Nucleotide sequence and deduced amino acid sequence
of the approximately 3.5 kb PstI/BamHI fragment
comprising lys-gingipain coding sequences

```
         10           20           30           40
          *            *            *            *
CTG CAG AAG TTC ACT CTT TCG CAT ATA GTG ACC CTC TTT TCT CTC AGC
GAC GTC TTC AAG TGA GAA AGC GTA TAT CAC TGG GAG AAA AGA GAG TCG 50           60           70           80           90
  *            *            *            *            *
ATA ATG GCA CCT ATC ATA TCA GTA AGG GGC GTA TTG TCT TTT CGA ACA
TAT TAC CGT GGA TAG TAT AGT CAT TCC CCG CAT AAC AGA AAA GCT TGT
```

TABLE 7-continued

Nucleotide sequence and deduced amino acid sequence
of the approximately 3.5 kb PstI/BamHI fragment
comprising lys-gingipain coding sequences

```
            100          110          120          130          140
             *            *            *            *            *
      ATG TAC AGC CCG AGA ACT CTT TAC TTC CAC ATC ACA CCC CCG ACT CCT
      TAC ATG TCG GGC TCT TGA GAA ATG AAG GTG TAG TGT GGG GGC TGA GGA 150          160          170          180          190
             *            *            *            *            *
      TAG TCA AGG ATC TTT TTT CCG CTT TCC CCT CCG CTC TCT TCC TCA TGC
      ATC AGT TCC TAG AAA AAA GGC GAA AGG GGA GGC GAG AGG AGT ACG 200          210          220          230          240
             *            *            *            *            *
      TGG ACT GAC TTA ACC TTG GTC TGC TCT ACT TTT CGG TTG TAA ATA CAT
      ACC TGA CTG AAT TGG AAC CAG ACG AGA TGA AAA GCC AAC ATT TAT GTA 250          260          270          280
             *            *            *            *
      GCA ACA CAA TAA CTT TTT TAA GTG TTG TTA GAC AAC ACT TTT ACA AGA
      CGT TGT GTT ATT GAA AAA ATT CAC AAC AAT CTG TTG TGA AAA TGT TCT 290          300          310          320          330
       *            *            *            *            *
      CTC TGA CTT TTA ATG AGG TGG AGC ATG AAC CTT TTC CTC TTT CAT CTT
      GAG ACT GAA AAT TAC TCC ACC TCG TAC TTG GAA AAG GAG AAA GTA GAA 340          350          360          370          380
             *            *            *            *            *
      CTC CTT CAG ATT ACA GTC AAT ATT TTG GCA AAA GGC TAA TTG ACA GCC
      GAG GAA GTC TAA TGT CAG TTA TAA AAC CGT TTT CCG ATT AAC TGT CGG 390          400          410          420          430
             *            *            *            *            *
      TTT TAT AAG GGT TAA TCC CTT GTC GCT TAT ATT GAA AAC ATG TTC TTT
      AAA ATA TTC CCA ATT AGG GAA CAG CGA ATA TAA CTT TTG TAC AAG AAA 440          450          460          470          480
             *            *            *            *            *
      ACG ATC CGA TAC TCT TCT TAA ATC GAA ATT TTT CTC TAA ATT GCG CCG
      TGC TAG GCT ATG AGA AGA ATT TAG CTT TAA AAA GAG ATT TAA CTC GGC 490          500          510          520
             *            *            *            *
      CAA CAA AAC TCC TTG AGA AAA GTA CCA ATA GAA ATA GAA GGT AGC ATT
      GTT GTT TTG AGG AAC TCT TTT CAT GGT TAT CTT TAT CTT CCA TCG TAA 530          540          550          560          570
       *            *            *            *            *
      TTG CCT TTA AAT TCC TTT TCT TTT CTT GGA TTG TTC TTG AAA TGA ATC
      AAC GGA AAT TTA AGG AAA AGA AAA GAA CCT AAC AAG AAC TTT ACT TAG 580          590          600          610          620
             *            *            *            *            *
      TTA TTT GTG GAT CTT TTT TGT TTT TTT TAA CCC GGC CGT GGT TCT CTG
      AAT AAA CAC CTA GAA AAA ACA AAA AAA ATT GGG CCG GCA CCA AGA GAC 630          640          650          660          670
             *            *            *            *            *
      AAT CAC GAC CAT AAA TTG TTT TAA AGT ATG AGG AAA TTA TTA TTG CTG
      TTA GTG CTG GTA TTT AAC AAA ATT TCA TAC TCC TTT AAT AAT AAC GAC
                                              M   R   K   L   L   L>

680          690          700          710          720
             *            *            *            *            *
      ATC GCG GCG TCC CTT TTG GGA GTT GGT CTT TAC GCC CAA AAC GCC AAG
      TAG CGC CGC AGG GAA AAC CCT CAA CCA GAA ATG CGG GTT TTG CGG TTC
       I   A   A   S   L   L   G   V   G   L   Y   A   Q   N   A   K>

730          740          750          760
             *            *            *            *
      ATT AAG CTT GAT GCT CCG ACT ACT CGA ACG ACA TGC ACG AAC AAT AGC
      TAA TTC GAA CTA CGA GGC TGA TGA GCT TGC TGT ACG TGC TTG TTA TCG
       I   K   L   D   A   P   T   T   R   T   T   C   T   N   N   S>

770          780          790          800          810
       *            *            *            *            *
      TTC AAG CAG TTC GAT GCA AGC TTT TCG TTC AAT GAA CTC GAG CTG ACA
      AAG TTC GTC AAG CTA CGT TCG AAA AGC AAG TTA CTT CAG CTC GAC TGT
       F   K   Q   F   D   A   S   F   S   F   N   E   V   E   L   T>

820          830          840          850          860
             *            *            *            *            *
      AAG GTG GAG ACC AAA GGT GGT ACT TTC GCC TCA GTG TCA ATT CCG GGT
      TTC CAC CTC TGG TTT CCA CCA TGA AAG CGG AGT CAC AGT TAA GGC CCA
       K   V   E   T   K   G   G   T   F   A   S   V   S   I   P   G>
```

TABLE 7-continued

Nucleotide sequence and deduced amino acid sequence
of the approximately 3.5 kb PstI/BamHI fragment
comprising lys-gingipain coding sequences

```
       870           880           890           900           910
        *             *             *             *             *
GCA TTC CCG ACC GGT GAG GTT GGT TCT CCC GAA GTG CCA GCA GTT AGG
CGT AAG GGC TGG CCA CTC CAA CCA AGA GGG CTT CAC GGT CGT CAA TCC
 A   F   P   T   G   E   V   G   S   P   E   V   P   A   V   R>

920           930           940           950           960
        *             *             *             *             *
AAG TTG ATT GCT GTG CCT GTC GGA GCC ACA CCT GTT GTT CGC GTG AAG
TTC AAC TAA CGA CAC GGA CAG CCT CGG TGT GGA CAA CAA GCG CAC TTC
 K   L   I   A   V   P   V   G   A   T   P   V   V   R   V   K>

970           980           990          1000
        *             *             *             *
AGT TTT ACC GAG CAA GTT TAC TCT CTG AAC CAA TAC GGT TCC GAA AAG
TCA AAA TGG CTC GTT CAA ATG AGA GAC TTG GTT ATG CCA AGG CTT TTC
 S   F   T   E   Q   V   Y   S   L   N   Q   Y   G   S   E   K>

1010          1020          1030          1040          1050
  *             *             *             *             *
CTC ATG CCA CAT CAA CCC TCT ATG AGC AAG AGT GAT GAT CCC GAA AAG
GAG TAC GGT GTA GTT GGG AGA TAC TCG TTC TCA CTA CTA GGG CTT TTC
 L   M   P   H   Q   P   S   M   S   K   S   D   D   P   E   K>

1060          1070          1080          1090          1100
        *             *             *             *             *
GTT CCC TTC GCT TAC AAT GCT GCT GCT TAT GCA CGC AAA GGT TTT GTC
CAA GGG AAG CGA ATG TTA CGA CGA CGA ATA CGT GCG TTT CCA AAA CAG
 V   P   F   A   Y   N   A   A   A   Y   A   R   K   G   F   V>

1110          1120          1130          1140          1150
        *             *             *             *             *
GGA CAA GAA CTG ACC CAA GTA GAA ATG TTG GGG ACA ATG CGT GGT GTT
CCT GTT CTT GAC TGG GTT CAT CTT TAC AAC CCC TGT TAC GCA CCA CAA
 G   Q   E   L   T   Q   V   E   M   L   G   T   M   R   G   V>

1160          1170          1180          1190          1200
        *             *             *             *             *
CGC ATT GCA GCT CTT ACC ATT AAT CCT GTT CAG TAT GAT GTA GTT GCA
GCG TAA CGT CGA GAA TGG TAA TTA GGA CAA GTC ATA CTA CAT CAA CGT
 R   I   A   A   L   T   I   N   P   V   Q   Y   D   V   V   A>

1210          1220          1230          1240
        *             *             *             *
AAC CAA TTG AAG GTT AGA AAC AAC ATC GAA ATT GAA GTA AGC TTT CAG
TTG GTT AAC TTC CAA TCT TTG TTG TAG CTT TAA CTT CAT TCG AAA GTC
 N   Q   L   K   V   R   N   N   I   E   I   E   V   S   F   Q>

1250          1260          1270          1280          1290
  *             *             *             *             *
GGA GCT GAT GAA GTA GCT ACA CAA CGT TTG TAT GAT GCT TCT TTT AGC
CCT CGA CTA CTT CAT CGA TGT GTT GCA AAC ATA CTA CGA AGA AAA TCG
 G   A   D   E   V   A   T   Q   R   L   Y   D   A   S   F   S>

1300          1310          1320          1330          1340
        *             *             *             *             *
CCT TAT TTC GAA ACA GCT TAT AAA CAG CTC TTC AAT AGA GAT GTT TAT
GGA ATA AAG CTT TGT CGA ATA TTT GTC GAG AAG TTA TCT CTA CAA ATA
 P   Y   F   E   T   A   Y   K   Q   L   F   N   R   D   V   Y>

1350          1360          1370          1380          1390
        *             *             *             *             *
ACA GAT CAT GGC GAC TTG TAT AAT ACG CCG GTT CGT ATG CTT GTT GTT
TGT CTA GTA CCG CTG AAC ATA TTA TGC GGC CAA GCA TAC GAA CAA CAA
 T   D   H   G   D   L   Y   N   T   P   V   R   M   L   V   V>

1400          1410          1420          1430          1440
        *             *             *             *             *
GCA GGT GCA AAA TTC AAA GAA GCT CTC AAG CCT TGG CTC ACT TGG AAG
CGT CCA CGT TTT AAG TTT CTT CGA GAG TTC GGA ACC GAG TGA ACC TTC
 A   G   A   K   F   K   E   A   L   K   P   W   L   T   W   K>

1450          1460          1470          1480
        *             *             *             *
GCT CAA AAG GGC TTC TAT CTG GAT GTG CAT TAC ACA GAC GAA GCT GAA
CGA GTT TTC CCG AAG ATA GAC CTA CAC GTA ATG TGT CTG CTT CGA CTT
 A   Q   K   G   F   Y   L   D   V   H   Y   T   D   E   A   E>

1490          1500          1510          1520          1530
  *             *             *             *             *
GTA GGA ACG ACA AAC GCC TCT ATC AAG GCA TTT ATT CAC AAG AAA TAC
CAT CCT TGC TGT TTG CGG AGA TAG TTC CGT AAA TAA GTG TTC TTT ATG
 V   G   T   G   N   A   S   I   K   A   F   I   H   K   K   Y>
```

TABLE 7-continued

Nucleotide sequence and deduced amino acid sequence
of the approximately 3.5 kb PstI/BamHI fragment
comprising lys-gingipain coding sequences

```
     1540          1550          1560          1570          1580
      *             *             *             *             *
AAT GAT GGA TTG GCA GCT AGT GCT GCT CCG GTC TTC TTG GCT TTG GTT
TTA CTA CCT AAC CGT CGA TCA CGA CGA GGC CAG AAG AAC CGA AAC CAA
 N   D   G   L   A   A   S   A   A   P   V   F   L   A   L   V>

1590          1600          1610          1620          1630
      *             *             *             *             *
GGT GAC ACT GAC GTT ATT AGC GGA GAA AAA GGA AAG AAA ACA AAA AAA
CCA CTG TGA CTG CAA TAA TCG CCT CTT TTT CCT TTC TTT TGT TTT TTT
 G   D   T   D   V   I   S   G   E   K   G   K   K   T   K   K>

1640          1650          1660          1670          1680
      *             *             *             *             *
GTT ACC GAC TTG TAT TAC AGT GCA GTC GAT GGC GAC TAT TTC CCT GAA
CAA TGG CTG AAC ATA ATG TCA CGT CAG CTA CCG CTG ATA AAG GGA CTT
 V   T   D   L   Y   Y   S   A   V   D   G   D   Y   F   P   E>

1690          1700          1710          1720
            *             *             *             *
ATG TAT ACT TTC CGT ATG TCT GCT TCT TCC CAA GAA GAA CTG ACG AAC
TAC ATA TGA AAG GCA TAC AGA CGA AGA AGG GTT CTT CTT GAC TGC TTG
 M   Y   T   F   R   M   S   A   S   S   P   E   E   L   T   N>

1730          1740          1750          1760          1770
  *             *             *             *             *
ATC ATT GAT AAG GTA TTG ATG TAT GAA AAG GCT ACT ATG CCG GAT AAG
TAG TAA CTA TTC CAT AAC TAC ATA CTT TTC CGA TGA TAC GGC CTA TTC
 I   I   D   K   V   L   M   Y   E   K   A   T   M   P   D   K>

1780          1790          1800          1810          1820
      *             *             *             *             *
AGC TAT TTG GAA AAG GCC CTC TTG ATT GCC GGT GCT GAC TCC TAC TGG
TCG ATA AAC CTT TTC CGG GAG AAC TAA CGG CCA CGA CTG AGG ATG ACC
 S   Y   L   E   K   A   L   L   I   A   G   A   D   S   Y   W>

1830          1840          1850          1860          1870
      *             *             *             *             *
AAT CCT AAG ATA GGC CAG CAA ACC ATC AAA TAT GCT GTA CAG TAT TAC
TTA GGA TTC TAT CCG GTC GTT TGG TAG TTT ATA CGA CAT GTC ATA ATG
 N   P   K   I   G   Q   Q   T   I   K   Y   A   V   Q   Y   Y>

1880          1890          1900          1910          1920
      *             *             *             *             *
TAC AAT CAA GAT CAT GGC TAT ACA GAT GTG TAC AGT TAC CCT AAA GCT
ATG TTA GTT CTA GTA CCG ATA TGT CTA CAC ATG TCA ATG GGA TTT CGA
 Y   N   Q   D   H   G   Y   T   D   V   Y   S   Y   P   K   A>

1930          1940          1950          1960
            *             *             *             *
CCT TAT ACA GGC TGC TAT AGT CAC TTG AAT ACC GGT GTC GGC TTT GCC
GGA ATA TGT CCG ACG ATA TCA GTG AAC TTA TGG CCA CAG CCG AAA CGG
 P   Y   T   G   C   Y   S   H   L   N   T   G   V   G   F   A>

1970          1980          1990          2000          2010
  *             *             *             *             *
AAC TAT ACA GCG CAT GGA TCT GAG ACA TCA TGG GCA GAT CCG TCC GTG
TTG ATA TGT CGC GTA CCT AGA CTC TGT AGT ACC CGT CTA GGC AGG CAC
 N   Y   T   A   H   G   S   E   T   S   W   A   D   P   S   V>

2020          2030          2040          2050          2060
      *             *             *             *             *
ACC GCC ACT CAA GTG AAA GCA CTC ACA AAT AAG AAC AAA TAC TTC TTA
TGG CGG TGA GTT CAC TTT CGT GAG TGT TTA TTC TTG TTT ATG AAG AAT
 T   A   T   Q   V   K   A   L   T   N   K   T   K   Y   F   L>

2070          2080          2090          2100          2110
      *             *             *             *             *
GCT ATT GGG AAC TGC TGT GTT ACA GCT CAA TTC GAT TAT CCA CAG CCT
CGA TAA CCC TTG ACG ACA CAA TGT CGA GTT AAG CTA ATA GGT GTC GGA
 A   I   G   N   C   C   V   T   A   Q   F   D   Y   P   Q   P>

2120          2130          2140          2150          2160
      *             *             *             *             *
TGC TTT GGA GAG GTA ATG ACT CGT GTC AAG GAG AAA GGT GCT TAT GCC
ACG AAA CCT CTC CAT TAC TGA GCA CAG TTC CTC TTT CCA CGA ATA CGG
 C   F   G   E   V   M   T   R   V   K   E   K   G   A   Y   A>

2170          2180          2190          2200
            *             *             *             *
TAT ATC GGT TCA TCT CCA AAT TCT TAT TGG GGC GAG GAC TAC TAT TGG
ATA TAG CCA AGT AGA GGT TTA AGA ATA ACC CCG CTC CTG ATG ATA ACC
 Y   I   G   S   S   P   N   S   Y   W   G   E   D   Y   Y   W>
```

TABLE 7-continued

Nucleotide sequence and deduced amino acid sequence
of the approximately 3.5 kb PstI/BamHI fragment
comprising lys-gingipain coding sequences

```
     2210          2220          2230          2240          2250
      *             *             *             *             *
 AGT GTG GGT GCT AAT GCA GTA TTT GGT GTT CAG CCT ACT TTT GAA GGT
 TCA CAC CCA CGA TTA CGT CAT AAA CCA CAA GTC GGA TGA AAA CTT CCA
  S   V   G   A   N   A   V   F   G   V   Q   P   T   F   E   G>

2260          2270          2280          2290          2300
      *             *             *             *             *
 ACG TCT ATG GGT TCT TAT GAT GCT ACA TTC TTG GAA GAT TCG TAC AAC
 TGC AGA TAC CCA AGA ATA CTA CGA TGT AAG AAC CTT CTA AGC ATG TTG
  T   S   M   G   S   Y   D   A   T   F   L   E   D   S   Y   N>

2310          2320          2330          2340          2350
      *             *             *             *             *
 ACA GTG AAC TCT ATT ATG TGG GCA GGT AAT CTT GCT GCT ACT CAT GCC
 TGT CAC TTG AGA TAA TAC ACC CGT CCA TTA GAA CGA CGA TGA GTA CGG
  T   V   N   S   I   M   W   A   G   N   L   A   A   T   H   A>
                                                         ___ ___

2360          2370          2380          2390          2400
      *             *             *             *             *
 GAA AAT ATC GGC AAT GTT ACC CAT ATC GGT GCT CAT TAC TAT TGG GAA
 CTT TTA TAG CCG TTA CAA TGG GTA TAG CCA CGA GTA ATG ATA ACC CTT
  E   N   I   G   N   V   T   H   I   G   A   H   Y   Y   W   E>

2410          2420          2430          2440
              *             *             *             *
 GCT TAT CAT GTC CTT GGC GAT GGT TCG GTT ATG CCT TAT CGT GCA ATG
 CGA ATA GTA CAG GAA CCG CTA CCA AGC CAA TAC GGA ATA GCA CGT TAC
  A   Y   H   V   L   G   D   G   S   V   M   P   Y   R   A   M>
 ___ ___ ___ ___ ___

2450          2460          2470          2480          2490
  *             *             *             *             *
 CCT AAG ACC AAT ACT TAT ACG CTT CCT GCT TCT CTG CCT CAG AAT CAG
 GGA TTC TGG TTA TGA ATA TGC GAA GGA CGA AGA GAC GGA GTC TTA GTC
  P   K   T   N   T   Y   T   L   P   A   S   L   P   Q   N   Q>

2500          2510          2520          2530          2540
      *             *             *             *             *
 GCT TCT TAT AGC ATT CAG GCT TCT GCC GGT TCT TAC GTA GCT ATT TCT
 CGA AGA ATA TCG TAA GTC CGA AGA CGG CCA AGA ATG CAT CGA TAA AGA
  A   S   Y   S   I   Q   A   S   A   G   S   Y   V   A   I   S>

2550          2560          2570          2580          2590
      *             *             *             *             *
 AAA GAT GGA GTT TTG TAT GGA ACA GGT GTT GCT AAT GCC AGC GGT GTT
 TTT CTA CCT CAA AAC ATA CCT TGT CCA CAA CGA TTA CGG TCG CCA CAA
  K   D   G   V   L   Y   G   T   G   V   A   N   A   S   G   V>

2600          2610          2620          2630          2640
      *             *             *             *             *
 GCG ACT GTG AAT ATG ACT AAG CAG ATT ACG GAA AAT GGT AAT TAT GAT
 CGC TGA CAC TTA TAC TGA TTC GTC TAA TGC CTT TTA CCA TTA ATA CTA
  A   T   V   N   M   T   K   Q   I   T   E   N   G   N   Y   D>

2650          2660          2670          2680
      *             *             *             *
 GTA GTT ATC ACT CGC TCT AAT TAT CTT CCT GTG ATC AAG CAA ATT CAG
 CAT CAA TAG TGA GCG AGA TTA ATA GAA GGA CAC TAG TTC GTT AAG TC
  V   V   I   T   R   S   N   Y   L   P   V   I   K   Q   I   Q>

2690          2700          2710          2720          2730
  *             *             *             *             *
 GCA GGA GAG CCT AGC CCC TAC CAG CCT GTT TCC AAC TTG ACT GCT ACA
 CGT CCT CTC GGA TCG GGG ATG GTC GGA CAA AGG TTG AAC TGA CGA TGT
  A   G   E   P   S   P   Y   Q   P   V   S   N   L   T   A   T>

2740          2750          2760          2770          2780
      *             *             *             *             *
 ACG CAG GGT CAG AAA GTA ACG CTC AAG TGG GAT GCC CCG AGC GCA AAG
 TGC GTC CCA GTC TTT CAT TGC GAG TTC ACC CTA CGG GGC TCG CGT TTC
  T   Q   G   Q   K   V   T   L   K   W   D   A   P   S   A   K>

2790          2800          2810          2820          2830
          *             *             *             *             *
 AAG GCA GAA GGT TCC CGT GAA GTA AAA CGG ATC GGA GAC GGT CTT TTC
 TTC CGT CTT CCA AGG GCA CTT CAT TTT GCC TAG CCT CTG CCA GAA AAG
  K   A   E   G   S   R   E   V   K   R   I   G   D   G   L   F>

2840          2850          2860          2870          2880
      *             *             *             *             *
 GTT ACG ATC GAA CCT GCA AAC GAT GTA CGT GCC AAC GAA GCC AAG GTT
 CAA TGC TAG CTT GGA CGT TTG CTA CAT GCA CGG TTG CTT CGG TTC CAA
  V   T   I   E   P   A   N   D   V   R   A   N   E   A   K   V>
                                         ___ ___ ___ ___ ___
```

TABLE 7-continued

Nucleotide sequence and deduced amino acid sequence
of the approximately 3.5 kb PstI/BamHI fragment
comprising lys-gingipain coding sequences

```
        2890            2900            2910            2920
         *               *               *               *
GTG CTC GCA GCA GAC AAC GTA TGG GGA GAC AAT ACG GGT TAC CAG TTC
CAC GAG CGT CGT CTG TTG CAT ACC CCT CTG TTA TGC CCA ATG GTC AAG
 V   L   A   A   D   N   V   W   G   D   N   T   G   Y   Q   F>

2930            2940            2950            2960            2970
 *               *               *               *               *
TTG TTG GAT GCC GAT CAC AAT ACA TTC GGA AGT GTC ATT CCG GCA ACC
AAC AAC CTA CGG CTA GTG TTA TGT AAG CCT TCA CAG TAA GGC CGT TGG
 L   L   D   A   D   H   N   T   F   G   S   V   I   P   A   T>

2980            2990            3000            3010            3020
     *               *               *               *               *
GGT CCT CTC TTT ACC GGA ACA GCT TCT TCC AAT CTT TAC AGT GCG AAC
CCA GGA GAG AAA TGG CCT TGT CGA AGA AGG TTA GAA ATG TCA CGC TTG
 G   P   L   F   T   G   T   A   S   S   N   L   Y   S   A   N>

3030            3040            3050            3060            3070
         *               *               *               *               *
TTC GAG TAT TTG ATC CCG GCC AAT GCC GAT CCT GTT GTT ACT ACA CAG
AAG CTC ATA AAC TAG GGC CGG TTA CGG CTA GGA CAA CAA TGA TGT GTC
 F   E   Y   L   I   P   A   N   A   D   P   V   V   T   T   Q>

3080            3090            3100            3110            3120
             *               *               *               *               *
AAT ATT ATC GTT ACA GGA CAG GGT GAA GTT GTA ATC CCC GGT GGT GTT
TTA TAA TAG CAA TGT CCT GTC CCA CTT CAA CAT TAG GGG CCA CCA CAA
 N   I   I   V   T   G   Q   G   E   V   V   I   P   G   G   V>

3130            3140            3150            3160
             *               *               *               *
TAC GAC TAT TGC ATT ACG AAC CCG GAA CCT GCA TCC GGA AAG ATG TGG
ATG CTG ATA ACG TAA TGC TTG GGC CTT GGA CGT AGG CCT TTC TAC ACC
 Y   D   Y   C   I   T   N   P   E   P   A   S   G   K   M   W>

3170            3180            3190            3200            3210
 *               *               *               *               *
ATC GCA GGA GAT GGA GGC AAC CAG CCT GCA CGT TAT GAC GAT TTC ACA
TAG CGT CCT CTA CCT CCG TTG GTC GGA CGT GCA ATA CTG CTA AAG TGT
 I   A   G   D   G   G   N   Q   P   A   R   Y   D   D   F   T>

3220            3230            3240            3250            3260
     *               *               *               *               *
TTC GAA GCA GGC AAG AAG TAC ACC TTC ACG ATG CGT CGC GCC GGA ATG
AAG CTT CGT CCG TTC TTC ATG TGG AAG TGC TAC GCA GCG CGG CCT TAC
 F   E   A   G   K   K   Y   T   F   T   M   R   R   A   G   M>

3270            3280            3290            3300            3310
         *               *               *               *               *
GGA GAT GGA ACT GAT ATG GAA GTC GAA GAC GAT TCA CCT GCA AGC TAT
CCT CTA CCT TGA CTA TAC CTT CAG CTT CTG CTA AGT GGA CGT TCG ATA
                                                                 *
 G   D   G   T   D   M   E   V   E   D   D   S   P   A   S   Y>

3320            3330            3340            3350            3360
             *               *               *               *               *
ACC TAC ACG GTG TAT CGT GAC GGC ACG AAG ATC AAG GAA GGT CTG ACG
TGG ATG TGC CAC ATA GCA CTG CCG TGC TTC TAG TTC CTT CCA GAC TGC
     *   *   *
 T   Y   T   V   Y   R   D   G   T   K   I   K   E   G   L   T>

3370            3380            3390            3400
             *               *               *               *
GCT ACG ACA TTC GAA GAA GAC GGT GTA GCT GCA GGC AAT CAT GAG TAT
CGA TGC TGT AAG CTT CTT CTG CCA CAT CGA CGT CCG TTA GTA CTC ATA
                                     * *
 A   T   F   E   E   D   G   V   A   A   G   N   H   E   Y>

3410            3420            3430            3440            3450
 *               *               *               *               *
TGC GTG GAA GTT AAG TAC ACA GCC GGC GTA TCT CCG AAG GTA TGT AAA
ACG CAC CTT CAA TTC ATG TGT CGG CCG CAT AGA GGC TTC CAT ACA TTT

C   V   E   V   K   Y   T   A   G   V   S   P   K   V   C   K>

3460            3470
 *               *
GAC GTT ACG GTA GAA GGA TCC
CTG CAA TGC CAT CTT CCT AGG

D   V   T   V   E   G   S>
```

The first ATG begins at nucleotide 652 and is followed by a long open reading frame (ORF) of 2825 nucleotides. This ORF is the largest one observed. However, the first ATG is followed by 4 others (at nucleotides 1012, 1030, 1129 and 1141). The deduced amino acid sequence for the ORF extending from nucleotide 652 through nucleotide 3477 is given in Table 7 and in SEQ ID NO:13. The ATG at nucleotide 652 is the most likely candidate to initiate translation because it is followed by a typical signal peptide sequence. This can be confirmed by expressing in a bacterial host and determining the N-terminal amino acid sequence of the precursor.

The 60 kDa enzymatically active component of the Lys-gingipain protein complex has an N-terminal amino acid sequence as given in SEQ ID NO:1. This sequence is encoded (and underlined) at nucleotides 1336–1398 in Table 7 (see also SEQ ID NO:13).

Without wishing to be bound by any particular theory, it is believed that the coding sequence of the 60 kDa active component of the Lys-gingipain complex extends through nucleotide 2863 in Table 7 (see also SEQ ID NO:13). The amino acid sequence identical to the amino-terminal sequence of the 44, 27 and 17 kDa Lys-gingipain complex components (SEQ ID NO:2), at least one of which is believed to function as a hemagglutinin, is encoded at nucleotides 2864–2938 in Table 7 (see also SEQ ID NO:13). Again, without wishing to be bound by any particular theory, it is believed that a protease with specificity for cleavage after arginine residues processes the polyprotein which is (in part) encoded within the nucleotide sequence of Table 7 (SEQ ID NO:13). The predicted molecular mass of 55.9 kDa for a 509 amino acid protein encoded from nucleotides 1336–2863 is consistent with the empirically determined estimate of 60 kDa (SDS-PAGE). However, this processed protein has a lower molecular weight than the Lys-specific P. gingivalis protease of 70 kDa described by Scott et al. (1993) J. Biol. Chem. supra.

Table 8 presents an alignment of portions of the 60 kDa active component of the exemplified P. gingivalis Lys-gingipain complex with portions of other cysteine proteases. Sequences 1–10 (SEQ ID NOS:19–28) are taken from Bourgeau et al. (1992) Infect. Immun. 60, 3186–3192. The first His residue of the Lys-gingipain 60 kDa component is encoded at nucleotides 2346–2348 (Table 7; SEQ ID NO:13). The N-terminal amino acid sequence of the hemagglutin component of the Lys-gingipain protein complex is given in SEQ ID NO:2. This amino acid sequence is encoded (and underlined) at nucleotides 2863–2937 in Table 7 (see also SEQ ID NO:13).

TABLE 8

Composite alignment of the deduced amino acid sequence of Lys-gingipain complex catalytic component (amino acids 338–361) with sequences of certain other cysteine proteases

|     | Sequence | |
| --- | --- | --- |
|     | HAENI-GNVTHIGAHYYWEAYHVLG | (SEQ ID NO:18) |
| 1.  | HAYTVLGYTVSNGA-YYLIIRNPWG | (SEQ ID NO:19) |
| 2.  | HAVTAVGYGKSGGKG-YILIKNSWG | (SEQ ID NO:20) |
| 3.  | HAVLAVGYGEQNGLL-YWIVKNSWG | (SEQ ID NO:21) |
| 4.  | HAVNIVGYSNAQGVD-YWIVRNSWD | (SEQ ID NO:22) |
| 5.  | GCVTAVGYGSNSNGK-YWIVKNSW | (SEQ ID NO:23) |
| 6.  | HGVLLVGYNDNSNPP-YWIVKNSW | (SEQ ID NO:24) |
| 7.  | GGLLLVGYNDSAAVP-YWIIKNSW | (SEQ ID NO:25) |
| 8.  | HAIVIVGYGTEGGVD-YWIVKNSWD | (SEQ ID NO:26) |
| 9.  | HAIRILGWGVENGTP-YWLVANSWN | (SEQ ID NO:27) |
| 10. | HAVAAVGY-NPG---YILVKNSWG | (SEQ ID NO:28) |

1: P. gingivalis, protease (trp);

TABLE 8-continued

Composite alignment of the deduced amino acid sequence of Lys-gingipain complex catalytic component (amino acids 338–361) with sequences of certain other cysteine proteases 2: Carica papaya;
3: rat cathepsin;
4: Dermatophagoides pteronysinus;
5: Entamoeba histolytica;
6: Trypanosoma brucei;
7: Trypanosoma cruzi;
8: Chinese gooseberry actinidin;
9: human cathepsin B;
10: papaya papain.

A comparison of the available deduced amino acid sequence of the hemagglutinin component of Lys-gingipain in the available deduced amino sequence of the hemagglutinin component of Arg-gingipain reveals a region of high DNA sequence homology between nucleotides 3543–3710 of the Arg-gingipain-hemagglutinin available coding sequence disclosed in U.S. Ser. No. 08/119,361, incorporated by reference herein, and nucleotides 3310–3477 of the coding sequence of the hemagglutinin component of Lys-gingipain disclosed herein (in SEQ ID NO:13). (It is noted that the ORF in Table 7 (SEQ ID NO:13) does not include a translation termination codon). These 167 nucleotides show 96% sequence identity and encode 56 amino acids which show 98% sequence identity. The 205 amino acids of hemagglutinin component, encoded from nucleotides 2864–3477 in Table 7 (SEQ ID NO:13) give rise to a molecule with a calculated molecular weight of 22 kDa which is smaller than the 27 kDa predicted. However, no stop codon is present. It is a matter of ordinary skill to isolate the remainder of the protease-hemagglutinin polyprotein's coding sequence. For example, one can create a genomic library of a Sau3A partial digest, e.g., of P. gingivalis DNA and screening with hybridization probes from the 5' end of the ORF of SEQ ID NO:13 [e.g., MK-9-29 (SEQ ID NO:15), MK-10-29 (SEQ ID NO:16), and/or lys-1-33 (SEQ ID NO:17)] with a probe from near the 3' end of SEQ ID NO:13, where that latter probe is at least about 30 nucleotides in length. A clone(s) hybridizing to these probes is subjected to restriction analysis and sequencing to locate the 3' end of the Lys-specific protease-hemagglutin coding sequence.

The Lys-gingipain complex may be used in methods of identifying agents that modulate Lys-gingipain proteinase activity, whether by acting on the proteinase itself or preventing the interaction of a proteinase with a protein in gingival area. One such method comprises the steps of incubating a proteinase with a putative therapeutic, i.e., Lys-gingipain inhibiting, agent; determining the activity of the proteinase incubated with the agent; and comparing the activity obtained in step with the activity of a control sample of proteinase that has not been incubated with the agent. The Lys-gingipain of the present invention is also useful for mediating specific proteolytic cleavage following lysine residues in proteins or oligopeptides and analogs thereof.

Methods of treating or ameliorating the effects of Lys-gingipain on affected gingival crevices of a human or animal with periodontal disease are provided. Such methods include administering to the animal (or human) an effective amount of a physiologically acceptable Lys-gingipain inhibitor. Known proteinase inhibitors are generally not physiologically acceptable, but acceptable inhibitors will include agents that inhibit Lys-gingipain but do not affect, or affect only marginally, the activity of endogenous proteinases.

Such inhibitors can be obtained from a variety of sources including but not limited to inhibitory antibodies and small molecules. The inhibitors can be administered by a variety of methods including but not limited to topically, via aerosol to the nasal passages or lungs, subdermally and intravenously. The inhibitors can be administered as needed, particularly when applied topically. These methods of administration are known in the art and will not be described in detail herein.

It is understood by the skilled artisan that there can be limited numbers of amino acid substitutions in a protein without significantly affecting function, and that nonexemplified Lys-gingipain proteins can have some amino acid sequence divergence from the exemplified amino acid sequence. Such naturally occurring variants can be identified, e.g., by hybridization to the exemplified (mature) Lys-gingipain 60 kDa component coding sequence under conditions appropriate to detect at least about 70% nucleotide sequence homology, preferably about 80%, more preferably about 90% and most preferably 95–100% sequence homology.

It is well known in the biological arts that certain amino acid substitutions can be made in protein sequences without affecting the function of the protein. Generally, conservative amino acids are tolerated without affecting protein function. Similar amino acids can be those that are similar in size and/or charge properties, for example, aspartate and glutamate and isoleucine and valine are both pairs of similar amino acids. Similarity between amino acid pairs has been assessed in the art in a number of ways. For example, Dayhoff et al. (1978) in *Atlas of Protein Sequence and Structure*, Volume 5, Supplement 3, Chapter 22, pages 345–352, which is incorporated by reference herein, provides frequency tables for amino acid substitutions which can be employed as a measure of amino acid similarity. Dayhoff et al.'s frequency tables are based on comparisons of amino acid sequences for proteins having the same function from a variety of evolutionarily different sources.

A polynucleotide or fragment thereof is "substantially homologous" (or "substantially similar") to another polynucleotide if, when optimally aligned (with appropriate nucleotide insertions or deletions) with another polynucleotide, there is nucleotide sequence identity for approximately 60% of the nucleotide bases, usually approximately 70%, more usually about 80%, preferably about 90%, and more preferably about 95% to 100% of the nucleotide bases.

Alternatively, substantial homology (or similarity) exists when a polynucleotide or fragment thereof will hybridize to another under polynucleotide under selective hybridization conditions. Selectivity of hybridization exists under hybridization conditions which allow one to distinguish the target polynucleotide of interest from other polynucleotides. Typically, selective hybridization will occur when there is approximately 55% similarity over a stretch of about 14 nucleotides, preferably approximately 65%, more preferably approximately 75%, and most preferably approximately 90%. See Kanehisa (1984) Nuc. *Acids Res.*, 12:203–213. The length of homology comparison, as described, may be over longer stretches, and in certain embodiments will often be over a stretch of about 17 to 20 nucleotides, and preferably about 36 or more nucleotides.

The hybridization of polynucleotides is affected by such conditions as salt concentration, temperature, or organic solvents, in addition to the base composition, length of the complementary strands, and the number of nucleotide base mismatches between the hybridizing polynucleotides, as will be readily appreciated by those skilled in the art. Stringent temperature conditions will generally include temperatures in excess of 30° C., typically in excess of 37° C., and preferably in excess of 45° C. Stringent salt conditions will ordinarily be less than 1M, typically less than 500 mM, and preferably less than 200 mM. However, the combination of parameters is much more important than the measure of any single parameter (Wetmur and Davidson (1968) *J. Mol. Biol.* 31, 349–370).

An "isolated" or "substantially pure" polynucleotide is a polynucleotide which is substantially separated from other polynucleotide sequences which naturally accompany a native gingipain-1 sequence. The term embraces a polynucleotide sequence which has been removed from its naturally occurring environment, and includes recombinant or cloned DNA isolates, chemically synthesized analogues and analogues biologically synthesized by heterologous systems.

A polynucleotide is said to "encode" a polypeptide if, in its native state or when manipulated by methods known to those skilled in the art, it can be transcribed and/or translated to produce the polypeptide of a fragment thereof. The anti-sense strand of such a polynucleotide is also said to encode the sequence.

A nucleotide sequence is operably linked when it is placed into a functional relationship with another nucleotide sequence. For instance, a promoter is operably linked to a coding sequence if the promoter affects its transcription or expression. Generally, operably linked means that the sequences being linked are contiguous and, where necessary to join two protein coding regions, contiguous and in reading frame. However, it is well known that certain genetic elements, such as enhancers, may be operably linked even at a distance, i.e., even if not contiguous.

The term "recombinant" polynucleotide refers to a polynucleotide which is made by the combination of two otherwise separated segments of sequence accomplished by the artificial manipulation of isolated segments of polynucleotides by genetic engineering techniques or by chemical synthesis. In so doing one may join together polynucleotide segments of desired functions to generate a desired combination of functions.

Polynucleotide probes include an isolated polynucleotide attached to a label or reporter molecule and may be used to identify and isolate other Lys-gingipain coding sequences. Probes comprising synthetic oligonucleotides or other polynucleotides may be derived from naturally occurring or recombinant single or double stranded nucleic acids or be chemically synthesized. Polynucleotide probes may be labelled by any of the methods known in the art, e.g., random hexamer labeling, nick translation, or the Klenow fill-in reaction.

Large amounts of the polynucleotides may be produced by replication in a suitable host cell. Natural or synthetic DNA fragments coding for a proteinase or a fragment thereof will be incorporated into recombinant polynucleotide constructs, typically DNA constructs, capable of introduction into and replication in a prokaryotic or eukaryotic cell. Usually the construct will be suitable for replication in a unicellular host, such as yeast or bacteria, but a multicellular eukaryotic host may also be appropriate, with or without integration within the genome of the host cells. Commonly used prokaryotic hosts include strains of *Escherichia coli*, although other prokaryotes, such as *Bacillus subtilis* or Pseudomonas may also be used. Mammalian or other eukaryotic host cells include yeast, filamentous fungi, plant, insect, amphibian and avian species. Such factors as ease of manipulation, ability to appropriately glycosylate expressed proteins, degree and control of protein expression, ease of purification of expressed proteins away from cellular contaminants or other factors may determine the choice of the host cell.

The polynucleotides may also be produced by chemical synthesis, e.g., by the phosphoramidite method described by Beaucage and Caruthers (1981) *Tetra. Letts.*, 22, 1859–1862 or the triester method according to Matteuci et al. (1981) *J. Am. Chem. Soc.*, 103, 3185, and may be performed on commercial automated oligonucleotide synthesizers. A double-stranded fragment may be obtained from the single stranded product of chemical synthesis either by synthesizing the complementary strand and annealing the strand together under appropriate conditions or by adding the complementary strand using DNA polymerase with an appropriate primer sequence.

DNA constructs prepared for introduction into a prokaryotic or eukaryotic host will typically comprise a replication system (i.e. vector) recognized by the host, including the intended DNA fragment encoding the desired polypeptide, and will preferably also include transcription and translational initiation regulatory sequences operably linked to the polypeptide-encoding segment. Expression systems (expression vectors) may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Signal peptides may also be included where appropriate from secreted polypeptides of the same or related species, which allow the protein to cross and/or lodge in cell membranes or be secreted from the cell.

An appropriate promoter and other necessary vector sequences will be selected so as to be functional in the host. Examples of workable combinations of cell lines and expression vectors are described in Sambrook et al. (1989) vide infra; Ausubel et al. (Eds.) (1987) *Current Protocols in Molecular Biology*, Greene Publishing and Wiley Interscience, New York; and Metzger et al. (1988) *Nature*, 334, 31–36. Many useful vectors for expression in bacteria, yeast, mammalian, insect, plant or other cells are well known in the art and may be obtained such vendors as Stratagene, New England Biolabs, Promega Biotech, and others. In addition, the construct may be joined to an amplifiable gene (e.g., DHFR) so that multiple copies of the gene may be made. For appropriate enhancer and other expression control sequences, see also *Enhancers and Eukaryotic Gene Expression*, Cold Spring Harbor Press, N.Y. (1983). While such expression vectors may replicate autonomously, they may less preferably replicate by being inserted into the genome of the host cell.

Expression and cloning vectors will likely contain a selectable marker, that is, a gene encoding a protein necessary for the survival or growth of a host cell transformed with the vector. Although such a marker gene may be carried on another polynucleotide sequence co-introduced into the host cell, it is most often contained on the cloning vector. Only those host cells into which the marker gene has been introduced will survive and/or grow under selective conditions. Typical selection genes encode proteins that (a) confer resistance to antibiotics or other toxic substances, e.g., ampicillin, neomycin, methotrexate, etc.; (b) complement auxotrophic deficiencies; or (c) supply critical nutrients not available from complex media. The choice of the proper selectable marker will depend on the host cell; appropriate markers for different hosts are known in the art.

The recombinant vectors containing the Lys-gingipain coding sequences of interest can be introduced (transformed, transfected) into the host cell by any of a number of appropriate means, including electroporation; transformation or transfection employing calcium chloride, rubidium chloride, calcium phosphate, DEAE-dextran, or other substances; microprojectile bombardment; lipofection; and transfection or infection (where the vector is an infectious agent, such as a viral or retroviral genome). The choice of such means will often depend on the host cell. Large quantities of the polynucleotides and polypeptides of the present invention may be prepared by transforming suitable prokaryotic or eukaryotic host cells with gingipain-1-encoding polynucleotides of the present invention in compatible vectors or other expression vehicles and culturing such transformed host cells under conditions suitable to attain expression of the Arg-gingipain-encoding gene. The Lys-gingipain may then be recovered from the host cell and purified.

The coding sequence for the "mature" form of Lys-gingipain 60 kDa component or polyprotein coding sequence is expressed after PCR site-directed mutagenesis and cloning into an expression vector suitable for use in *E. coli*, for example. Exemplary expression vectors for *E. coli* and other host cells are given, for example in Sambrook et al. (1989), vide infra, and in Pouwels et al. (Eds.) (1986) *Cloning Vectors*, Elsevier Science Publishers, Amsterdam, the Netherlands.

In order to eliminate leader sequences and precursor sequences at the 5' side of the coding sequence, a combination of restriction endonuclease cutting and site-directed mutagenesis via PCR using an oligonucleotide containing a desired restriction site for cloning (one not present in coding sequence), a ribosome binding site, an translation initiation codon (ATG) and the codons for the first amino acids of the (mature) Lys-gingipain 60 kDa enzymatically active component. The oligonucleotide for site-directed mutagenesis at the 3' end of the coding sequence for mature active component includes nucleotides encoding the carboxyterminal amino acids of mature 60 kDa gingipain component, a translation termination codon (TAA, TGA or TAG), and a second suitable restriction endonuclease recognition site not present in the remainder of the DNA sequence to be inserted into the expression vector. The site-directed mutagenesis strategy is similar to that of Boone et al. (1990) *Proc. Natl. Acad. Sci. USA* 87, 2800–2804, as modified for use with PCR.

In another embodiment, polyclonal and/or monoclonal antibodies capable of specifically binding to a proteinase or fragments thereof are provided. The term antibody is used to refer both to a homogenous molecular entity, or a mixture such as a serum product made up of a plurality of different molecular entities. Monoclonal or polyclonal antibodies specifically reacting with the Lys-gingipains may be made by methods known in the art. See, e.g., Harlow and Lane (1988) *Antibodies: A Laboratory Manual*, CSH Laboratories; Goding (1986) *Monoclonal Antibodies: Principles and Practice*, 2d ed., Academic Press, New York; and Ausubel et al. (1987) supra. Also, recombinant immunoglobulins may be produced by methods known in the art, including but not limited to the methods described in U.S. Pat. No. 4,816,567. Monoclonal antibodies with affinities of $10^8$ $M^{-1}$, preferably $10^9$ to $10^{10}$ or more are preferred.

Antibodies specific for Lys-gingipain may be useful, for example, as probes for screening DNA expression libraries or for detecting the presence of Lys-gingipain in a test sample. Frequently, the polypeptides and antibodies will be labeled by joining, either covalently or noncovalently, a substance which provides a detectable signal. Suitable labels include but are not limited to radionuclides, enzymes, substrates, cofactors, inhibitors, fluorescent agents, chemiluminescent agents, magnetic particles and the like. United States Patents describing the use of such labels include but are not limited to U.S. Pat. Nos. 3,817,837; 3,850,752; 3,939,350; 3,996,345; 4,277,437; 4,275,149; and 4,366,241. An exemplified antibody was raised against an immunogen consisting of a peptide of SEQ ID NO:1, the 21-N-terminal amino acids of the catalytic component of the Lys-gingipain complex.

Antibodies specific for Lys-gingipain(s) and capable of inhibiting its proteinase activity may be useful in treating animals, including man, suffering from periodontal disease. Such antibodies can be obtained by the methods described above and subsequently screening the Lys-gingipain-specific antibodies for their ability to inhibit proteinase activity.

Compositions and vaccine preparations comprising an immunogenic amount of a substantially purified Lys-gingipain(s) derived from *P. gingivalis* and a suitable carrier therefor are provided, and preferably the Lys-gingipain is in the complex described herein. Such vaccines are useful, for example, in immunizing an animal, including humans, against inflammatory response and tissue damage caused by *P. gingivalis* in periodontal disease. The vaccine preparations can further comprise an immunogenic amount of one or more Arg-gingipains or an immunogenic fragment(s) or subunit(s) thereof. Such vaccines may comprise one or more Lys-gingipain proteinases, or in combination with another *P. gingivalis* protein or other immunogen or in combination with antigens from one or more other oral pathogens. By "immunogenic amount" is meant an amount capable of eliciting the production of antibodies directed against Lys-gingipain(s) in an individual to which the vaccine has been administered.

Immunogenic carriers may be used to enhance the immunogenicity of the proteinases. Such carriers include but are not limited to proteins and polysaccharides, liposomes, and bacterial cells and membranes. Protein carriers may be joined to the proteinases to form fusion proteins by recombinant or synthetic means or by chemical coupling. Useful carriers and means of coupling such carriers to polypeptide antigens are known in the art.

The vaccines may be formulated by any of the means known in the art. Such vaccines are typically prepared as injectables, either as liquid solutions or suspensions. Solid forms suitable for solution in, or suspension in, liquid prior to injection may also be prepared. The preparation may also, for example, be emulsified, or the protein encapsulated in liposomes.

The active immunogenic ingredients are often mixed with excipients or carriers which are pharmaceutically acceptable and compatible with the active ingredient. Suitable excipients include but are not limited to water, saline, dextrose, glycerol, ethanol, or the like and combinations thereof. The concentration of the immunogenic polypeptide in injectable formulations is usually in the range of 0.2 to 5 mg/ml.

In addition, if desired, the vaccines may contain minor amounts of auxiliary substances such as wetting or emulsifying agents, pH buffering agents, and/or adjuvants which enhance the effectiveness of the vaccine. Examples of adjuvants which may be effective include but are not limited to: aluminum hydroxide; N-acetyl-muramyl-L-threonyl-D-isoglutamine (thr-MDP); N-acetyl-nor-muramyl-L-alanyl-D-isoglutamine (CGP 11637, referred to as nor-MDP); N-acetylmuramyl-L-alanyl-D-isoglutaminyl-L-alanine-2-(1'-2'-dipalmitoyl-sn-glycero-3hydroxyphosphoryloxy)-ethylamine (CGP 19835A, referred to as MTP-PE); and RIBI, which contains three components extracted from bacteria, monophosphoryl lipid A, trehalose dimycolate and cell wall skeleton (MPL+TDM+CWS) in a 2% squalene/Tween 80 emulsion. The effectiveness of an adjuvant may be determined by measuring the amount of antibodies directed against the immunogen resulting from administration of the immunogen in vaccines which are also comprised of the various adjuvants. Such additional formulations and modes of administration as are known in the art may also be used.

Lys-gingipain complex and components of either or both thereof may be formulated into vaccines as neutral or salt forms. Pharmaceutically acceptable salts include but are not limited to the acid addition salts (formed with free amino groups of the peptide) which are formed with inorganic acids, e.g., hydrochloric acid or phosphoric acids; and organic acids, e.g., acetic, oxalic, tartaric, or maleic acid. Salts formed with the free carboxyl groups may also be derived from inorganic bases, e.g., sodium, potassium, ammonium, calcium, or ferric hydroxides, and organic bases, e.g., isopropylamine, trimethylamine, 2-ethylamino-ethanol, histidine, and procaine.

The vaccines are administered in a manner compatible with the dosage formulation, and in such amount as will be prophylactically and/or therapeutically effective. The quantity to be administered, which is generally in the range of about 100 to 1,000 µg of protein per dose, more generally in the range of about 5 to 500 µg of protein per dose, depends on the subject to be treated, the capacity of the individual's immune system to synthesize antibodies, and the degree of protection desired. Precise amounts of the active ingredient required to be administered may depend on the judgment of the physician or doctor of dental medicine and may be peculiar to each individual, but such a determination is within the skill of such a practitioner.

The vaccine may be given in a single dose or multiple dose schedule. A multiple dose schedule is one in which a primary course of vaccination may include 1 to 10 or more separate doses, followed by other doses administered at subsequent time intervals as required to maintain and or reinforce the immune response, e.g., at 1 to 4 months for a second dose, and if needed, a subsequent dose(s) after several months.

A method of monitoring the exposure of an animal or human to Lys-gingipain is provided. Such monitoring methods are useful, for example, in monitoring the progress of a therapy designed to lessen the symptoms of periodontitis.

In general, a biological sample obtained from the animal (e.g., blood, saliva, tissue) is incubated with Lys-gingipain or portions thereof under conditions suitable for antibody-antigen interactions. The detection of the formation of such interactions is indicative of prior exposure of the animal and the subsequent development of an immune response to the proteinase. Examples of such tests include but are not limited to enzyme-linked immunosorbent assays (ELISA).

Alternatively, the subject may be exposed to gingipain-1 and the subsequent reaction monitored. Such exposure may be cutaneously (e.g., by application to the skin via pricking or scratching), intracutaneously (e.g., via intracutaneous injection), subcutaneously, or introduced in the form of an aerosol (generally an aqueous aerosol) into the nasal or bronchial passages (nasoprovocation or bronchoprovocation, respectively), using methods well known in the art. Typical reactions, e.g., a weal and erythema in skin testing, or precipitin reactions measured in vitro, indicate an immunological response to the protein. See, e.g., *Basic and Clinical Immunology*, 6th ed., Stites et al., eds., (Appleton & Lange, 1987), pp. 436–438, for a general description.

A Lys-gingipain may also be used in methods of identifying agents that modulate proteinase activity, e.g., by acting on the proteinase itself. One such method comprises the steps of incubating Lys-gingipain-1 with a putative therapeutic agent; determining the activity of the proteinase incubated with the agent; and comparing the activity obtained in step with the activity of a control sample of proteinase that has not been incubated with the agent.

All references cited herein are hereby incorporated by reference in their entirety.

Except as noted hereafter, standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al. (1989) *Molecular Cloning*, Second Edition, Cold Spring Harbor Laboratory, Plainview, N.Y.; Maniatis et al. (1982) *Molecular Cloning*, Cold Spring Harbor Laboratory, Plainview, N.Y.; Wu (ed.) (1993) Meth. Enzymol. 218, Part I; Wu (ed.) (1979) Meth Enzymol. 68; Wu et al. (eds.) (1983) Meth. Enzymol. 100 and 101; Grossman and Moldave (eds.) Meth. Enzymol. 65; Miller (ed.) (1972) *Experiments in Molecular Genetics*, Cold Spring Harbor Laboratory, Cold Spring Harbor, N.Y., Old and Primrose (1981) *Principles of Gene Manipulation*, University of California Press, Berkeley; Schleif and Wensink (1982) *Practical Methods in Molecular Biology*; Glover (ed.) (1985) *DNA Cloning* Vol. I and II, IRL Press, Oxford, UK; Hames and Higgins (eds.) (1985) *Nucleic Acid Hybridization*, IRL Press, Oxford, UK; Setlow and Hollaender (1979) *Genetic Engineering: Principles and Methods*, Vols. 1–4, Plenum Press, New York. Abbreviations and nomenclature, where employed, are deemed standard in the field and commonly used in professional journals such as those cited herein.

The foregoing discussion and the following examples illustrate but are not intended to limit the invention. The skilled artisan will understand that alternative methods may be used to implement the invention.

THE EXAMPLES

Example 1

Purification of Lys-Gingipain

Example 1.1

Bacterial Cultivation

*P. gingivalis* strain H66 was obtained from Roland Arnold (Emory University, Atlanta, Ga.). Cells were grown in 500 ml of broth containing 15.0 g Trypticase Soy Broth (Difco, Detroit, Mich.), 2.5 g yeast extract, 2.5 mg hemin, 0.25 g cysteine, 0.05 g dithiothreitol, 0.5 mg menadione (all from Sigma Chemical Company, St. Louis, Mo.) anaerobically at 37° C. for 48 hr in an atmosphere of 85% $N_2$, 10% $CO_2$, 5% $H_2$. The entire 500 ml culture was used to inoculate 20 liters of the same medium, and the latter was incubated in a fermentation tank at 37° C. for 48 hr (to a final optical density of 1.8 at 650 nm).

Example 1.2

Proteinase Purification (high molecular weight gingipain)

The culture supernatant (2,900 ml) was obtained by centrifugation of the whole culture (6,000×g, 30 min, 4° C.). Chilled acetone (4,350 ml) was added to this fraction over a period of 15 min, with the temperature of the solution maintained below 0° C. at all times, using an ice/salt bath to precipitate proteins. This mixture was centrifuged (6,000×g, 30 min, −15° C.). The precipitate was dissolved in 290 ml of 20 mM Bis-Tris-HCl, 150 mM NaCl, 5 mM $CaCl_2$, 0.02% (w/v) $NAN_3$, pH 6.8 (Buffer A), and dialyzed against Buffer A containing 1.5 mM 4,4'-Dithiodipyridine disulphide for 4 h, followed by 2 changes of Buffer A overnight. The dialyzed fraction was centrifuged (27,000×g, 30 min, 4° C.), following which the supernatant was concentrated to 40 ml by ultrafiltration using an Amicon PM-10 membrane. This concentrated fraction was applied to a Sephadex G-150 column (5×115 cm=2260 ml; Pharmacia, Piscataway, N.J.) which had previously been equilibrated with Buffer A, and the fractionation was carried out at 30 ml/h (1.5 cm/h). Fractions (9 ml) were assayed for activity against Bz-L-Arg-pNa and Z-L-Lys-pNa (Novabiochem; 0.5 mM). Amidolytic activities for Bz-L-Arg-pNa (0.5 mM) or Z-L-Lys-pNa were measured in 0.2M Tris-HCl, 1 mM $CaCl_2$, 0.02% (w/v) $NAN_3$, 10 mM L-cysteine, pH 7.6. Three peaks with activity against both pNA substrates were found. The highest molecular weight peak of activity contained most of the Z-L-Lys-pNA amidolytic activity. The fractions of the highest molecular weight peak of activity were pooled, concentrated to 60 ml using ultrafiltration and dialyzed overnight against two changes of 50 mM Tris-HCl, 1 mM $CaCl_2$, 0.02% $NAN_3$, pH 7.4 (Buffer B).

This high MW fraction concentrate was applied to an L-Arginine-Sepharose column (1.5×30 cm=50 ml), which had previously been equilibrated with Buffer B at a flow rate of 20 ml/hr (11.3 cm/h), following which the column was washed with two column volumes of Buffer B. Following this, a step gradient of 500 mM NaCl was applied in Buffer B and the column was washed with this concentration of NaCl until the $A_{280}$ baseline fell to zero. After re-equilibration of the column with Buffer B, a linear gradient from 0–750 mM L-Lysine in Buffer B was applied in a total volume of 300 ml, followed by 100 ml of Buffer B containing 750 mM L-Lysine. The column was once again re-equilibrated with Buffer B and a further gradient to 100 mM L-arginine in 300 ml was applied in the same way. Fractions (6 ml) from the Lys wash and from the Arg wash were assayed for activity against the two pNA substrates as described previously. The lysine gradient eluted a major peak of activity against Z-L-Lys-pNa only and the arginine gradient did the same for an enzyme degrading Bz-L-Arg-pNa. The active (for Z-L-Lys-pNA) fractions were pooled and dialyzed against two changes of 20 mM Bis-Tris-HCl, 1 mM $CaCl_2$, 0.02% (w/v) $NAN_3$, pH 6.4 (Buffer C) and the dialyzate was concentrated to 10 ml using Amicon PM-10 membranes.

The dialyzate was applied to an anion exchange FPLC column (Mono Q FPLC column, Pharmacia LKB Biotechnology Inc., Piscataway, N.J.) equilibrated in Buffer C, the column was washed with 5 column volumes of Buffer C at a flow rate of 1.0 ml/min, following which bound protein was eluted with a 3 step gradient [0–200 mM NaCl (10 min), followed by 200–275 mM NaCl (15 min) and 275–500 mM NaCl (5 min), each in Buffer C. The active fractions from Mono Q chromatography were pooled.

When pure High Molecular Weight Arg-gingipain was desired, the fractions from L-Arginine Sepharose with activity for Bz-L-Arg-pNA were similarly concentrated and dialized, and applied to a Mono Q FPLC column. After the Buffer C column wash described above, bound protein was eluted with a three-step gradient [0–200 mM NaCl (10 min); 200–275 mM NaCl (15 min); 275–500 mM NaCl (5 min)]. Bz-L-Arg-pNA hydrolysis was monitored for eluted fractions, and those with activity were pooled, concentrated and dialyzed for further study. These pooled fractions comprised the HGP (High Molecular Weight Arg-gingipain) complex.

Example 2

Characterization of Lys-Gingipain

Example 2.1

SDS-PAGE

SDS-PAGE was carried out using the method of Shagger and Von Janon (1987), *Analyt. Biochem.* 166, 368–379.

Example 2.2

Enzyme Assays

Unless otherwise noted, amidolytic activities of the Arg- and Lys-specific proteinases were measured with the substrates Bz-L-Arg-pNa (0.5 mM), S2251 (0.16 mM) and Z-L-Lys-pNa (0.5 mM) in 0.2M Tris-HCl, 1 mM CaCl$_2$, 0.02% (w/v) NAN$_3$, 10 mM L-cysteine, pH 7.6. For specific characterization of Lys-gingipain, the buffer used was at pH 8.0, however, and without CaCl$_2$.

General proteolytic activity was assayed using the same buffer system as described for detecting amidolytic activity, but using azocoll or azocasein (2% w/v) as substrate as described for Cathepsin L. by Barrett and Kirschke (1981), *Meth. Enzymol.* 80, 535–561.

Example 2.3

Enzyme Specificity

Potential substrates were incubated with Lys-gingipain complex at a molar ratio of 1:250 enzyme:substrate ratio in 50 mM Tris-HCl, 5 mM cysteine, pH 8.5 at 37° C. Aliquots were removed at various times, and the digestion was stopped by acidification with 5% TFA. Each aliquot was applied to an Ultrasphere ODS reverse phase column (5μ, 4.6 mm×25 cm, Beckman, Fullerton, Calif.) and fractionation accomplished by a program which consisted of a 5 minute initial hold in 0.1% TFA after injection, followed by a 2.5% per minute gradient to 0.08% TFA, containing 80% acetonitrile. Each peak detected by absorbance at 220 nm was collected and analyzed for amino acid content.

Example 2.4

Amino Acid Sequence Analysis

Proteins were prepared for sequencing, following SDS-PAGE and blotting to a PVDF membrane, as described by Matsudaira, P. (1987), *J. Biol. Chem.* 262, 10035–10038. The sequence analysis was performed with an Applied Biosystems 4760A gas-phase sequencer (Applied Biosystems, Foster City, Calif.) using the program designed by the manufacturer.

Example 2.5

Materials

Bz-L-Arg-pNa, Phenylmethane sulfonyl fluoride (PMSF), tosyl-L-lysine-chloromethyl ketone (TLCK), trans-epoxysuccinyl-L-leucylamide-(4-guanidino)butane) [E-64], azocasein, antipain, N-p-tosyl-Gly-Pro-Lys-pNa, adrenocorticotrophic hormone fragment 11–24, Met-Lys-Bradykinin and 62-Endorphin were from Sigma Chemical Co. (St. Louis, Mo.). S2390 (H-D-Val-Phe-Lys-pNA) and S2251 (D-Val-Leu-Lys-pNA) were from Kabi-Vitrum, (Beaumont, Tex.), DFP and leupeptin were from Calbiochem (La Jolla, Calif.). Z-L-Lys-pNa was from Novabiochem (La Jolla, Calif.), Melittin and neurotensin were from Boehringer-Mannheim (Indianapolis, Ind.). Two peptides used for specificity studies were prepared by the peptide synthesis facility at the University of Georgia.

Example 3

Hemagglutination assays

Hemagglutination assays were carried out as described by Garvey et al. (1977), *Methods in Immunology*, W. A. Benjamin, Inc., Reading, MA, using 1% sheep red blood cells in Tris buffered saline.

Example 4

Immunological Studies of Lys-gingipain

Example 4.1

Production of anti-Lys-gingipain anti-peptide antibodies

Two peptides were synthesized; one consisting of the first 15 N-Terminal amino acids from the 60 kDa catalytic subunit of Lys-gingipain (D V Y T D H G D L Y N T P V R; amino acids 1–15 of SEQ ID NO:1) attached to the multiple antigen peptide (MAP) resin (Tam, J. P. (1988) *Proc. Natl. Acad. Sci. USA* 85, 5409–5413) and other consisting of the first 21 amino acids (D V Y T D H G D L Y N T P V R M L V V A G; SEQ ID NO:1) synthesized in a free form.

The MAP-attached peptide was emulsified in a 1:1 ratio with Freund's complete adjuvant (FCA) and an amount representative of 200 μg of the peptide was injected subcutaneously into each of two rabbits. Two and six weeks after the first injection, further inoculations were made with the same amount in Freund's incomplete adjuvant. At week 7 a test bleed was made and the sera was tested in an ELISA. It was found that the anti-peptide antibody titer was high, but the response against the protein itself was quite low. This is similar to what other researchers have found with peptides attached to the MAP resin [Briand et al. (1992), *J. Immunol. Methods*, 156, 255–265]. In order to improve the anti-protein titer, the rabbits were injected with 200 μg of the 21 amino acid free peptide in FCA at weeks 10 and 14. A test bleed at this stage revealed that the titer of the anti-protein antibodies improved by approximately 100-fold.

Example 4.2

Preparation of fractions from *P. gingivalis*

Cultures of *P. gingivalis* strains H66, ATCC 33277 and ATCC 53978 were grown in 250 ml volumes exactly as described earlier. The cultures were centrifuged (6,000×g, 30 min, 4° C.) and the precipitated cells were washed 3 times with 50 mM Tris-HCl, 1 mM CaCl$_2$, 0.02% (w/v) NAN$_3$, pH 7.4. The cells were then resuspended in 30 ml of the above buffer and sonicated at 1500 Hz for 20 min using a 1 sec burst cycle. The ruptured cells were centrifuged (27,000×g, 30 min, 4° C.) and the cloudy supernatant was ultra-centrifuged (100,000×g, 60 min, 4° C.). The supernatant was regarded as the cytosol fraction and the precipitate, resuspended in 3 ml of buffer, as the membrane fraction. The culture fluid was also ultra-centrifuged (100,000×g, 60 min, 4° C.) and the precipitate, resuspended in 3 ml of the buffer, was regarded as the vesicle fraction.

Example 4.3

Immunoblotting of the *P. gingivalis* fractions.

The fractions from *P. gingivalis* were electrophoresed using the Tris/Tricine-SDS-PAGE system and then electroblotted to a nitrocellulose membrane as described by Towbin et al. (1979), *Proc. Natl. Acad. Sci. USA*, 76, 4350–4354.

Example 5.1

Oligonucleotide Synthesis

Oligonucleotide primers for PCR probes and sequencing were synthesized by the phosphoramidite method with an Applied Biosystems model 394 automated DNA synthesizer (Applied Biosystems, Foster City, Calif.) and purified by PAGE and desalted on Sep-Pak (Millipore Corp., Beverly, Mass.) using standard protocols. Primer MK-9-29 was designed to bind to the noncoding strand of Lys-gingipain DNA corresponding to the $NH_2$-terminal portion of the 60 kDa catalytic component, i.e., to the sequence encoding amino acids 1–6 within SEQ ID NO:1. The sequence of the 29-base primer consists of 17 bases specific for the Lys-gingipain catalytic protein and included a 6-base EcoRI site and six additional bases at the 5' end (underlined), as follows: 5'-AGATCTGAATTCGAYGTNTAYACNGAYCA-3' (SEQ ID NO:15), where Y is C or T and N is A or G or C or T. Primer MK-10-29 was designed to bind to the coding strand of Lys-gingipain catalytic protein DNA corresponding to the amino acids 16–21 of the mature protein, i.e., residues 16–21 of SEQ ID NO:1. The sequence of the 29-base primer consists of 17 bases specific for the Lys-gingipain complex catalytic component DNA and includes a 6-base HindIII restriction site and six additional bases at the 5' end (underlined), as follows: 5'-AGATCTAAGCTTCCNGCNACNACNARCAT-3', where R is A or G and N is A or G or C or T (SEQ ID NO:16). Primer Lys-1-33: 5'-CATACGAACCGGCGTATTATACAAGTCGCCATG-3' (SEQ ID NO:17) was designed to bind to the noncoding strand of Lys-gingipain complex active component DNA corresponding to amino acids 7–16 of the mature protein, i.e., amino acids 7–16 of SEQ ID NO:1, and was designed on the basis of partial DNA sequence information for the Lys-gingipain active component coding sequence (nucleotides 1351–1383 of SEQ ID NO:13). This primer was used as a probe to screen a λDASH *P. gingivalis* genomic DNA library (see below). A total of 34 20-mer internal primers were designed to sequence the Lys-gingipain complex coding sequence.

Example 5.2

Polymerase Chain Reaction

The DNA template used in PCR was *P. gingivalis* total cellular DNA. The PCR was run using primer MK-9-29 (SEQ ID NO:15) along with primer MK-10-29 (SEQ ID NO:16); PCR consistently yielded a single 76-base pair product (P76) detected on a 7% acrylamide gel representing a partial Lys-gingipain DNA. After treatment with the Klenow enzyme and double digest with EcoR1/HindIII, P76 was cloned in M13mp18 and 19 (NEN Biolabs, Beverly, Mass.). After sequence analysis of P76, specific primer lys-1-33 (SEQ ID NO:17) was designed to use as a probe. The $^{32}$P-labeled lys-1-33 probe was generated by kinase reaction for use in subsequent hybridization screening of the λDASH library. Incorporated nucleotides were separated from unincorporated nucleotides on a Sephadex G-25 column (Boehringer Mannheim Corporation, Indianapolis, Ind.)

Example 5.3

Construction of the genomic DNA library

A λDASH DNA library was constructed according to the protocols of Stratagene (La Jolla, Calif.), using the lambda DASH™ II/BamHI cloning kit. BamHI was used to cut the isolated *P. gingivalis* genomic DNA. A library of $2\times10^5$ independent recombinant clones was obtained.

Example 5.4

Screening the genomic DNA Library

Approximately $2\times10^5$ phages were grown on 5×150 mm agar plates, lifted in duplicate onto supported nitrocellulose transfer membrane (BAS-NC, Schleicher & Schuel, Keene, NH), hybridized to the $^{32}$P-labeled lys-1-33 probe described above. Hybridizations were performed overnight at 42° C. in 2× Denhardt's solution (Denhardt, D. T. (1966), *Biochem. Biophys. Res. Comm.* 23, 641–646), 6× SSC (SSC is 15 mM sodium citrate, 150 mM NaCl), 0.4% SDS (w/v), 500 µg/ml fish sperm DNA. The filters were washed in 2× SSC containing 0.05% SDS (w/v) at 48° C. Seven positively hybridizing plaques were purified. After extraction and purification, the DNA was analyzed by restriction enzyme digestion and agarose gel electrophoresis. The 3.8 kb BamHI and the 3.4 PstI fragment from clone A2 were subsequently cloned into pBluescript SK(−) (Stratagene, La Jolla, Calif.). The 3.4 kb PstI fragment and the 0.9 kb PstI/BamHI 3'-end fragment were subcloned into M13mp18 and 19 and sequenced. Standard protocols for cDNA library screening, lambda phage purification, agarose gel electrophoresis and plasmid cloning were employed (Maniatis et al., 1982 supra).

Example 5.5

Southern Blot Analysis

The membranes were washed as described above. BamHI, HindIII- or PstI-digested *P. gingivalis* DNA samples were hybridized with $^{32}$P-labeled lys-1-33 (SEQ ID NO:17). One BamHI fragment of approximately 3.8 kb and one PstI fragment of approximately 3 kb were found. No HindIII fragment was seen. BamHI- and PstI-digested λDASH DNA after screening and purification of positive recombinant clones from the library. The A2 clone was sequenced as described below.

Example 5.6

DNA Sequencing

Double-stranded DNA cloned into pBluescript SK(−) and single-stranded DNA cloned into M13mp18 and 19 were sequenced by the dideoxy terminator method [Sanger et al. (1977) *Proc. Natl. Acad. Sci. USA* 74, 5463–5467] using sequencing kits purchased from United States Biochemical Corp. (Sequenase version 2.0; Cleveland, Ohio). The DNA was sequenced using M13 universal primer, reverse sequencing primer and internal primers according to the strategy presented in FIG. 8.

We claim:

1. A proteinase preparation comprising a substantially pure Lys-gingipain protein complex, said Lys-gingipain having an apparent molecular mass of 105 kDa as estimated by sodium dodecyl sulfate polyacrylamide gel electrophoresis, wherein sample is prepared without boiling, said Lys-gingipain having amidolytic and proteolytic activity for cleavage after L-lysine residues and having no amidolytic and/or proteolytic activity for cleavage after L-arginine residues, wherein the amidolytic and/or proteolytic activity is inhibited by TLCK, glycyl-glycine, cysteine protease group-specific inhibitors including iodoacetamide and iodoacetic acid, wherein the amidolytic and/or proteolytic activity of said Lys-gingipain is not sensitive to inhibition by trans-epoxysuccinyl-L-leucylamido-(4-guanidino) butane, EDTA, leupeptin, antipain, serine protease group-specific inhibitors including diisopropylfluorophosphate and phenylmethyl sulfonylfluoride.

2. The proteinase preparation of claim 1 wherein said Lys-gingipain protein complex comprises a catalytic component characterized by an N-terminal amino acid sequence as in SEQ ID NO:1.

3. The proteinase preparation of claim 1 wherein said Lys-gingipain complex has an enzymatically active component characterized by the amino acid sequence as given in SEQ ID NO:14 from amino acid 1 through amino acid 509.

4. The proteinase preparation of claim 1 wherein said preparation comprises proteins of molecular weights of 60, 30, 27 and 17 kDa as estimated by sodium dodecyl sulfate polyacrylamide gel electrophoresis after boiling of a sample of said proteinase preparation.

5. The proteinase preparation of claim 4 wherein said 30 and 27 kDa proteins are each identified by an N-terminal amino acid sequence as given in SEQ ID NO:2.

6. The proteinase preparation of claim 4 wherein said 17 kDa protein is characterized by an N-terminal amino acid sequence as given in SEQ ID NO:3.

7. The proteinase preparation of claim 1 wherein said preparation comprises proteins of molecular weights of 60, 44, 27 and 17 kDa as estimated by SDS-PAGE.

8. The proteinase preparation of claim 7 wherein said 60 kDa protein is characterized by an N-terminal amino acid sequence as given in SEQ ID NO:1.

9. The proteinase preparation of claim 7 wherein said 44 and 27 kDa proteins are each identified by an N-terminal amino acid sequence as given in SEQ ID NO:2.

10. The proteinase preparation of claim 7 wherein said 17 kDa protein is characterized by an N-terminal amino acid sequence as given in SEQ ID NO:3.

11. A vaccine comprising a substantially purified Lys-gingipain protein complex preparation of claim 1 and a suitable carrier therefor.

12. The vaccine according to claim 11, further comprising high molecular weight Arg-gingipain.

13. The vaccine according to claim 11 wherein said Lys-gingipain complex catalytic component has an amino acid sequence as given in SEQ ID NO:14 from amino acid 1 through amino acid 509.

14. A method of monitoring exposure of an animal to a Lys-gingipain, comprising the steps of:

(a) obtaining a sample from the animal; incubating the sample with Lys-gingipain protein complex; or portions thereof under conditions suitable for antibody-antigen interaction; and (b) detecting the presence of antibody-antigen complexes;

wherein the presence of antigen-antibody complexes is indicative of exposure of the animal to Lys-gingipain.

15. A method of identifying agents that modulate the effect of a Lys-gingipain protein complex on animals comprising the steps of (a) incubating a Lys-gingipain complex with the agent;

(b) exposing animal cells sensitive to Lys-gingipain incubated with the agent;

(c) determining the ability of Lys-gingipain protein complex incubated with the agent to affect the cells;

(d) comparing the effect seen in step c) with the effect of a control sample of a Lys-gingipain complex that has not been incubated with the agent on animal cells susceptible to the Lys-gingipain complex;

wherein the agents that modulate the effect of the Lys-gingipain change the activity of the Lys-gingipain complex as compared to the control sample.

16. A method of identifying agents that modulate Lys-gingipain protein complex activity comprising the steps of:

(a) incubating a substantially pure preparation of a Lys-gingipain complex with the agent;

(b) determining the activity of said complex incubated with the agent; and (c) comparing the activity obtained in step b) with the activity of a control sample of said complex that has not been incubated with the agent.

17. A method of ameliorating the affects of Lys-gingipain on an animal affected by Lys-gingipain, comprising administering to the animal an effective amount of a physiologically acceptable Lys-gingipain inhibitor.

18. An antibody specific for Lys-gingipain or a catalytic component of a Lys-gingipain protein complex wherein said antibody reacts specifically with a protein identified by an amino acid sequence as given in SEQ. ID NO:1.

* * * * *

UNITED STATES PATENT AND TRADEMARK OFFICE
CERTIFICATE OF CORRECTION

PATENT NO. : 5,707,620          Page 1 of 4
DATED      : January 13, 1998
INVENTOR(S): Travis, et al It is certified that error appears in the above-indentified patent and that said Letters Patent is hereby corrected as shown below:

In the Abstract, first line, delete "Provide" and replace with --Provided--.

In column 4, line 57, delete "an" and replace with --a--.

In column 5, line 46, delete "Ph" and replace with --pH--.

In column 6, line 16, delete "terminus," and replace with --terminus--.

In column 6, line 37, please insert --BOC-- before "benzoyloxycarbonyl".

In column 10, line 3, delete "lys-gingipain" and replace with --Lys-gingipain--.

In column 11, line 27, delete "strates" and replace with --strate--.

In column 11, Table 5, lines 37 and 38, delete ↓ " LYENKPRRPYIL" and replace with ↓ --LYENKPRRPYIL--.

In column 11, Table 5, lines 39 and 40, delete ↓ ↓ " GIGAVLKVLTTGLPALISWIKRKREE" and replace with ↓ ↓ --GIGAVLKVLTTGLPALISWIKRKREE--.

UNITED STATES PATENT AND TRADEMARK OFFICE
CERTIFICATE OF CORRECTION

PATENT NO. : 5,707,620
DATED : January 13, 1998
INVENTOR(S) : Travis, et al

It is certified that error appears in the above-indentified patent and that said Letters Patent is hereby corrected as shown below:

In column 11, Table 5, lines 44 and 45, delete "GGFMTSEKSQTPLVTLFKNAIIKNAYKKGE" and replace with --GGFMTSEKSQTPLVTLFKNAIIKNAYKKGE--.

In column 11, Table 5, line 47, delete "MKRPPGFSPEFR" and replace with --MKRPPGFSPFR--.

In column 11, Table 5, lines 48 and 49, delete "EEISEVKMDAEFRHDSGYEVHHQKLVF" and replace with --EEISEVKMDAEFRHDSGYEVHHQKLVF--.

In column 11, Table 5, lines 51 and 52, delete "EEISEVDLDAEFRHDSGYEVHHQKLVF" and replace with --EEISEVDLDAEFRHDSGYEVHHQKLVF--.

In column 14, line 27, delete "protein, these" and replace with --protein. These--.

In column 17 and 18, in the bottom line of the sequence between 1500 and 1510, please delete "G" and replace with --T--.

UNITED STATES PATENT AND TRADEMARK OFFICE
CERTIFICATE OF CORRECTION

PATENT NO. : 5,707,620
DATED : January 13, 1998
INVENTOR(S) : Travis, et al

It is certified that error appears in the above-indentified patent and that said Letters Patent is hereby corrected as shown below:

In column 19 and 20, in the bottom line of the sequence between 2050 and 2060, please delete "T" and replace with --N--.

In column 21 and 22, in the middle line of the sequence between 2390 and 2400, please delete "ATA ATG" and replace with --ATG ATA--.

In column 25, line 47, delete "glutin" and replace with --glutinin--.

In column 26, line 17, delete "in" and replace with --and--.

In column 26, line 44, delete "protease-hemagglutin" and replace with --protease-hemagglutinin--.

In column 29, line 46, please insert --from-- between "obtained" and "such".

In column 30, line 19, delete "Arg-gingipain-encoding" and replace with --Lys-gingipain-encoding--.

In column 30, line 32, please insert --we used-- between "sequence," and "a".

In column 30, line 36, delete "an translation" and replace with --a translation--.

UNITED STATES PATENT AND TRADEMARK OFFICE
CERTIFICATE OF CORRECTION

PATENT NO. : 5,707,620
DATED : January 13, 1998
INVENTOR(S) : Travis, et al

It is certified that error appears in the above-indentified patent and that said Letters Patent is hereby corrected as shown below:

In column 34, lines 11, 25, 32 and 54, delete "NAN$_3$," and replace with --NaN$_3$--.

In column 35, line 28, delete "NAN$_3$," and replace with --NaN$_3$--.

In column 36, line 4, delete "62-Endorphin" and replace with --β-Endorphin--.

In column 36, line 60, delete "NAN$_3$," and replace with --NaN$_3$--.

Signed and Sealed this

Eighteenth Day of August, 1998

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 28

( 2 ) INFORMATION FOR SEQ ID NO:1:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: Porphyromonas gingivalis
        ( B ) STRAIN: H66

( x i ) SEQUENCE DESCRIPTION: SEQ ID NO:1:

```
Asp Val Tyr Thr Asp His Gly Asp Leu Tyr Asn Thr Pro Val Arg Met
1               5                   10                  15
Leu Val Val Ala Gly
            20
```

( 2 ) INFORMATION FOR SEQ ID NO:2:

( i ) SEQUENCE CHARACTERISTICS:
        ( A ) LENGTH: 26 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: Porphyromonas gingivalis
        ( B ) STRAIN: H66

( x i ) SEQUENCE DESCRIPTION: SEQ ID NO:2:

```
Ala Asn Glu Ala Lys Val Val Leu Ala Ala Asp Asn Val Trp Gly Asp
1               5                   10                  15
Asn Thr Gly Tyr Ser Phe Leu Leu Asp Ala
            20                  25
```

( 2 ) INFORMATION FOR SEQ ID NO:3:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( v ) FRAGMENT TYPE: N-terminal ( v i ) ORIGINAL SOURCE:
    ( A ) ORGANISM: Porphyromonas gingivalis
    ( B ) STRAIN: H66

( x i ) SEQUENCE DESCRIPTION: SEQ ID NO:3:

```
Pro  Gln  Phe  Thr  Glu  Ile  Phe  Arg  Gln  Val  Asp  Leu  Pro  Ala  Gly  Thr
1                   5                        10                       15
```

( 2 ) INFORMATION FOR SEQ ID NO:4:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( v ) FRAGMENT TYPE: N-terminal ( v i ) ORIGINAL SOURCE:
        ( A ) ORGANISM: Porphyromonas gingivalis
        ( B ) STRAIN: H66

( x i ) SEQUENCE DESCRIPTION: SEQ ID NO:4:

```
Tyr  Thr  Pro  Val  Glu  Glu  Lys  Gln  Asn  Gly  Arg  Met  Ile  Val  Ile  Val
1                   5                        10                       15

Ala  Lys  Lys  Tyr  Glu  Gly
                    20
```

( 2 ) INFORMATION FOR SEQ ID NO:5:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( v ) FRAGMENT TYPE: N-terminal ( v i ) ORIGINAL SOURCE:
        ( A ) ORGANISM: Porphyromonas gingivalis
        ( B ) STRAIN: H66

( i x ) FEATURE:
        ( A ) NAME/KEY: Modified-site
        ( B ) LOCATION: 1..15
        ( D ) OTHER INFORMATION: /label=Uncertain
            / note="Amino acid 14 has not been identified with
            certainty."

( x i ) SEQUENCE DESCRIPTION: SEQ ID NO:5:

```
Ser  Gly  Gln  Ala  Glu  Ile  Val  Leu  Glu  Ala  His  Asp  Val  Xaa  Asn  Asp
1                   5                        10                       15

Gly
```

( 2 ) INFORMATION FOR SEQ ID NO:6:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( x i ) SEQUENCE DESCRIPTION: SEQ ID NO:6:

```
Leu Tyr Glu Asn Lys Pro Arg Arg Pro Tyr Ile Leu
1               5                   10
```

( 2 ) INFORMATION FOR SEQ ID NO:7:

- ( i ) SEQUENCE CHARACTERISTICS:
  - ( A ) LENGTH: 26 amino acids
  - ( B ) TYPE: amino acid
  - ( C ) STRANDEDNESS: single
  - ( D ) TOPOLOGY: linear

- ( i i ) MOLECULE TYPE: peptide

- ( i i i ) HYPOTHETICAL: NO

- ( i v ) ANTI-SENSE: NO

- ( x i ) SEQUENCE DESCRIPTION: SEQ ID NO:7:

```
Gly Ile Gly Ala Val Leu Lys Val Leu Thr Thr Gly Leu Pro Ala Leu
1               5                   10                  15
Ile Ser Trp Ile Lys Arg Lys Arg Glu Glu
                20              25
```

( 2 ) INFORMATION FOR SEQ ID NO:8:

- ( i ) SEQUENCE CHARACTERISTICS:
  - ( A ) LENGTH: 14 amino acids
  - ( B ) TYPE: amino acid
  - ( C ) STRANDEDNESS: single
  - ( D ) TOPOLOGY: linear

- ( i i ) MOLECULE TYPE: peptide

- ( i i i ) HYPOTHETICAL: NO

- ( i v ) ANTI-SENSE: NO

- ( x i ) SEQUENCE DESCRIPTION: SEQ ID NO:8:

```
Lys Pro Val Gly Lys Lys Arg Arg Pro Val Lys Val Tyr Pro
1               5                   10
```

( 2 ) INFORMATION FOR SEQ ID NO:9:

- ( i ) SEQUENCE CHARACTERISTICS:
  - ( A ) LENGTH: 30 amino acids
  - ( B ) TYPE: amino acid
  - ( C ) STRANDEDNESS: single
  - ( D ) TOPOLOGY: linear

- ( i i ) MOLECULE TYPE: peptide

- ( i i i ) HYPOTHETICAL: NO

- ( i v ) ANTI-SENSE: NO

- ( x i ) SEQUENCE DESCRIPTION: SEQ ID NO:9:

```
Gly Gly Phe Met Thr Ser Glu Lys Ser Gln Thr Pro Leu Val Thr Leu
1               5                   10                  15
Phe Lys Asn Ala Ile Ile Lys Asn Ala Tyr Lys Lys Gly Glu
                20              25                  30
```

( 2 ) INFORMATION FOR SEQ ID NO:10:

- ( i ) SEQUENCE CHARACTERISTICS:
  - ( A ) LENGTH: 11 amino acids
  - ( B ) TYPE: amino acid
  - ( C ) STRANDEDNESS: single ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:10:

```
Met  Lys  Arg  Pro  Pro  Gly  Phe  Ser  Pro  Phe  Arg
 1                  5                        10
```

( 2 ) INFORMATION FOR SEQ ID NO:11:

( i ) SEQUENCE CHARACTERISTICS:
                    ( A ) LENGTH: 27 amino acids
                    ( B ) TYPE: amino acid
                    ( C ) STRANDEDNESS: single
                    ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:11:

```
Glu  Glu  Ile  Ser  Glu  Val  Lys  Met  Asp  Ala  Glu  Phe  Arg  His  Asp  Ser
 1                  5                        10                            15

Gly  Tyr  Glu  Val  His  His  Gln  Lys  Leu  Val  Phe
                 20                      25
```

( 2 ) INFORMATION FOR SEQ ID NO:12:

( i ) SEQUENCE CHARACTERISTICS:
                    ( A ) LENGTH: 27 amino acids
                    ( B ) TYPE: amino acid
                    ( C ) STRANDEDNESS: single
                    ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:12:

```
Glu  Glu  Ile  Ser  Glu  Val  Asp  Leu  Asp  Ala  Glu  Phe  Arg  His  Asp  Ser
 1                  5                        10                            15

Gly  Tyr  Glu  Val  His  His  Gln  Lys  Leu  Val  Phe
                 20                      25
```

( 2 ) INFORMATION FOR SEQ ID NO:13:

( i ) SEQUENCE CHARACTERISTICS:
                    ( A ) LENGTH: 3477 base pairs
                    ( B ) TYPE: nucleic acid
                    ( C ) STRANDEDNESS: double
                    ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
                    ( A ) NAME/KEY: CDS
                    ( B ) LOCATION: 652..3477

( i x ) FEATURE:
                    ( A ) NAME/KEY: mat_peptide ( B ) LOCATION: 1336..2862

( x i ) SEQUENCE DESCRIPTION: SEQ ID NO:13:

```
CTGCAGAAGT TCACTCTTTC GCATATAGTG ACCCTCTTTT CTCTCAGCAT AATGGCACCT      60

ATCATATCAG TAAGGGGCGT ATTGTCTTTT CGAACAATGT ACAGCCCGAG AACTCTTTAC     120

TTCCACATCA CACCCCCGAC TCCTTAGTCA AGGATCTTTT TTCCGCTTTC CCCTCCGCTC     180

TCTTCCTCAT GCTGGACTGA CTTAACCTTG GTCTGCTCTA CTTTTCGGTT GTAAATACAT     240

GCAACACAAT AACTTTTTTA AGTGTTGTTA GACAACACTT TTACAAGACT CTGACTTTTA     300

ATGAGGTGGA GCATGAACCT TTTCCTCTTT CATCTTCTCC TTCAGATTAC AGTCAATATT     360

TTGGCAAAAG GCTAATTGAC AGCCTTTTAT AAGGGTTAAT CCCTTGTCGC TTATATTGAA     420

AACATGTTCT TTACGATCCG ATACTCTTCT TAAATCGAAA TTTTCTCTA AATTGCGCCG      480

CAACAAAACT CCTTGAGAAA AGTACCAATA GAAATAGAAG GTAGCATTTT GCCTTTAAAT     540

TCCTTTTCTT TTCTTGGATT GTTCTTGAAA TGAATCTTAT TTGTGGATCT TTTTGTTTT     600

TTTTAACCCG GCCGTGGTTC TCTGAATCAC GACCATAAAT TGTTTAAAG T ATG AGG       657
                                                          Met Arg
                                                              -228

AAA TTA TTA TTG CTG ATC GCG GCG TCC CTT TTG GGA GTT GGT CTT TAC      705
Lys Leu Leu Leu Leu Ile Ala Ala Ser Leu Leu Gly Val Gly Leu Tyr
-225                 -220                 -215

GCC CAA AAC GCC AAG ATT AAG CTT GAT GCT CCG ACT ACT CGA ACG ACA      753
Ala Gln Asn Ala Lys Ile Lys Leu Asp Ala Pro Thr Thr Arg Thr Thr
-210             -205                 -200                 -195

TGC ACG AAC AAT AGC TTC AAG CAG TTC GAT GCA AGC TTT TCG TTC AAT      801
Cys Thr Asn Asn Ser Phe Lys Gln Phe Asp Ala Ser Phe Ser Phe Asn
             -190                 -185                 -180

GAA GTC GAG CTG ACA AAG GTG GAG ACC AAA GGT GGT ACT TTC GCC TCA      849
Glu Val Glu Leu Thr Lys Val Glu Thr Lys Gly Gly Thr Phe Ala Ser
         -175                 -170                 -165

GTG TCA ATT CCG GGT GCA TTC CCG ACC GGT GAG GTT GGT TCT CCC GAA      897
Val Ser Ile Pro Gly Ala Phe Pro Thr Gly Glu Val Gly Ser Pro Glu
     -160                 -155                 -150

GTG CCA GCA GTT AGG AAG TTG ATT GCT GTG CCT GTC GGA GCC ACA CCT      945
Val Pro Ala Val Arg Lys Leu Ile Ala Val Pro Val Gly Ala Thr Pro
-145                 -140                 -135

GTT GTT CGC GTG AAA AGT TTT ACC GAG CAA GTT TAC TCT CTG AAC CAA      993
Val Val Arg Val Lys Ser Phe Thr Glu Gln Val Tyr Ser Leu Asn Gln
-130                 -125                 -120                 -115

TAC GGT TCC GAA AAG CTC ATG CCA CAT CAA CCC TCT ATG AGC AAG AGT     1041
Tyr Gly Ser Glu Lys Leu Met Pro His Gln Pro Ser Met Ser Lys Ser
             -110                 -105                 -100

GAT GAT CCC GAA AAG GTT CCC TTC GCT TAC AAT GCT GCT GCT TAT GCA     1089
Asp Asp Pro Glu Lys Val Pro Phe Ala Tyr Asn Ala Ala Ala Tyr Ala
         -95                  -90                  -85

CGC AAA GGT TTT GTC GGA CAA GAA CTG ACC CAA GTA GAA ATG TTG GGG     1137
Arg Lys Gly Phe Val Gly Gln Glu Leu Thr Gln Val Glu Met Leu Gly
     -80                  -75                  -70

ACA ATG CGT GGT GTT CGC ATT GCA GCT CTT ACC ATT AAT CCT GTT CAG     1185
Thr Met Arg Gly Val Arg Ile Ala Ala Leu Thr Ile Asn Pro Val Gln
-65                  -60                  -55

TAT GAT GTA GTT GCA AAC CAA TTG AAG GTT AGA AAC AAC ATC GAA ATT     1233
Tyr Asp Val Val Ala Asn Gln Leu Lys Val Arg Asn Asn Ile Glu Ile
-50                  -45                  -40                  -35

GAA GTA AGC TTT CAG GGA GCT GAT GAA GTA GCT ACA CAA CGT TTG TAT     1281
Glu Val Ser Phe Gln Gly Ala Asp Glu Val Ala Thr Gln Arg Leu Tyr
             -30                  -25                  -20
```

| | | | | | | | | | | | | | | | | |
|---|---|---|---|---|---|---|---|---|---|---|---|---|---|---|---|---|
| GAT | GCT | TCT | TTT | AGC | CCT | TAT | TTC | GAA | ACA | GCT | TAT | AAA | CAG | CTC | TTC | 1329 |
| Asp | Ala | Ser | Phe | Ser | Pro | Tyr | Phe | Glu | Thr | Ala | Tyr | Lys | Gln | Leu | Phe | |
| | | | -15 | | | | -10 | | | | | | -5 | | | |
| AAT | AGA | GAT | GTT | TAT | ACA | GAT | CAT | GGC | GAC | TTG | TAT | AAT | ACG | CCG | GTT | 1377 |
| Asn | Arg | Asp | Val | Tyr | Thr | Asp | His | Gly | Asp | Leu | Tyr | Asn | Thr | Pro | Val | |
| | 1 | | | | 5 | | | | | | 10 | | | | | |
| CGT | ATG | CTT | GTT | GTT | GCA | GGT | GCA | AAA | TTC | AAA | GAA | GCT | CTC | AAG | CCT | 1425 |
| Arg | Met | Leu | Val | Val | Ala | Gly | Ala | Lys | Phe | Lys | Glu | Ala | Leu | Lys | Pro | |
| 15 | | | | 20 | | | | | 25 | | | | | | 30 | |
| TGG | CTC | ACT | TGG | AAG | GCT | CAA | AAG | GGC | TTC | TAT | CTG | GAT | GTG | CAT | TAC | 1473 |
| Trp | Leu | Thr | Trp | Lys | Ala | Gln | Lys | Gly | Phe | Tyr | Leu | Asp | Val | His | Tyr | |
| | | | 35 | | | | | 40 | | | | | | 45 | | |
| ACA | GAC | GAA | GCT | GAA | GTA | GGA | ACG | ACA | AAC | GCC | TCT | ATC | AAG | GCA | TTT | 1521 |
| Thr | Asp | Glu | Ala | Glu | Val | Gly | Thr | Thr | Asn | Ala | Ser | Ile | Lys | Ala | Phe | |
| | | | | 50 | | | | | 55 | | | | | 60 | | |
| ATT | CAC | AAG | AAA | TAC | AAT | GAT | GGA | TTG | GCA | GCT | AGT | GCT | GCT | CCG | GTC | 1569 |
| Ile | His | Lys | Lys | Tyr | Asn | Asp | Gly | Leu | Ala | Ala | Ser | Ala | Ala | Pro | Val | |
| | | 65 | | | | | 70 | | | | | 75 | | | | |
| TTC | TTG | GCT | TTG | GTT | GGT | GAC | ACT | GAC | GTT | ATT | AGC | GGA | GAA | AAA | GGA | 1617 |
| Phe | Leu | Ala | Leu | Val | Gly | Asp | Thr | Asp | Val | Ile | Ser | Gly | Glu | Lys | Gly | |
| | | 80 | | | | | 85 | | | | | 90 | | | | |
| AAG | AAA | ACA | AAA | AAA | GTT | ACC | GAC | TTG | TAT | TAC | AGT | GCA | GTC | GAT | GGC | 1665 |
| Lys | Lys | Thr | Lys | Lys | Val | Thr | Asp | Leu | Tyr | Tyr | Ser | Ala | Val | Asp | Gly | |
| 95 | | | | | 100 | | | | | 105 | | | | | 110 | |
| GAC | TAT | TTC | CCT | GAA | ATG | TAT | ACT | TTC | CGT | ATG | TCT | GCT | TCT | TCC | CCA | 1713 |
| Asp | Tyr | Phe | Pro | Glu | Met | Tyr | Thr | Phe | Arg | Met | Ser | Ala | Ser | Ser | Pro | |
| | | | | 115 | | | | | 120 | | | | | 125 | | |
| GAA | GAA | CTG | ACG | AAC | ATC | ATT | GAT | AAG | GTA | TTG | ATG | TAT | GAA | AAG | GCT | 1761 |
| Glu | Glu | Leu | Thr | Asn | Ile | Ile | Asp | Lys | Val | Leu | Met | Tyr | Glu | Lys | Ala | |
| | | | 130 | | | | | 135 | | | | | 140 | | | |
| ACT | ATG | CCG | GAT | AAG | AGC | TAT | TTG | GAA | AAG | GCC | CTC | TTG | ATT | GCC | GGT | 1809 |
| Thr | Met | Pro | Asp | Lys | Ser | Tyr | Leu | Glu | Lys | Ala | Leu | Leu | Ile | Ala | Gly | |
| | | 145 | | | | | 150 | | | | | 155 | | | | |
| GCT | GAC | TCC | TAC | TGG | AAT | CCT | AAG | ATA | GGC | CAG | CAA | ACC | ATC | AAA | TAT | 1857 |
| Ala | Asp | Ser | Tyr | Trp | Asn | Pro | Lys | Ile | Gly | Gln | Gln | Thr | Ile | Lys | Tyr | |
| | | 160 | | | | | 165 | | | | | 170 | | | | |
| GCT | GTA | CAG | TAT | TAC | TAC | AAT | CAA | GAT | CAT | GGC | TAT | ACA | GAT | GTG | TAC | 1905 |
| Ala | Val | Gln | Tyr | Tyr | Tyr | Asn | Gln | Asp | His | Gly | Tyr | Thr | Asp | Val | Tyr | |
| 175 | | | | | 180 | | | | | 185 | | | | | 190 | |
| AGT | TAC | CCT | AAA | GCT | CCT | TAT | ACA | GGC | TGC | TAT | AGT | CAC | TTG | AAT | ACC | 1953 |
| Ser | Tyr | Pro | Lys | Ala | Pro | Tyr | Thr | Gly | Cys | Tyr | Ser | His | Leu | Asn | Thr | |
| | | | | 195 | | | | | 200 | | | | | 205 | | |
| GGT | GTC | GGC | TTT | GCC | AAC | TAT | ACA | GCG | CAT | GGA | TCT | GAG | ACA | TCA | TGG | 2001 |
| Gly | Val | Gly | Phe | Ala | Asn | Tyr | Thr | Ala | His | Gly | Ser | Glu | Thr | Ser | Trp | |
| | | | 210 | | | | | 215 | | | | | 220 | | | |
| GCA | GAT | CCG | TCC | GTG | ACC | GCC | ACT | CAA | GTG | AAA | GCA | CTC | ACA | AAT | AAG | 2049 |
| Ala | Asp | Pro | Ser | Val | Thr | Ala | Thr | Gln | Val | Lys | Ala | Leu | Thr | Asn | Lys | |
| | | 225 | | | | | 230 | | | | | 235 | | | | |
| AAC | AAA | TAC | TTC | TTA | GCT | ATT | GGG | AAC | TGC | TGT | GTT | ACA | GCT | CAA | TTC | 2097 |
| Asn | Lys | Tyr | Phe | Leu | Ala | Ile | Gly | Asn | Cys | Cys | Val | Thr | Ala | Gln | Phe | |
| | 240 | | | | | 245 | | | | | 250 | | | | | |
| GAT | TAT | CCA | CAG | CCT | TGC | TTT | GGA | GAG | GTA | ATG | ACT | CGT | GTC | AAG | GAG | 2145 |
| Asp | Tyr | Pro | Gln | Pro | Cys | Phe | Gly | Glu | Val | Met | Thr | Arg | Val | Lys | Glu | |
| 255 | | | | | 260 | | | | | 265 | | | | | 270 | |
| AAA | GGT | GCT | TAT | GCC | TAT | ATC | GGT | TCA | TCT | CCA | AAT | TCT | TAT | TGG | GGC | 2193 |
| Lys | Gly | Ala | Tyr | Ala | Tyr | Ile | Gly | Ser | Ser | Pro | Asn | Ser | Tyr | Trp | Gly | |
| | | | | 275 | | | | | 280 | | | | | 285 | | |
| GAG | GAC | TAC | TAT | TGG | AGT | GTG | GGT | GCT | AAT | GCA | GTA | TTT | GGT | GTT | CAG | 2241 |
| Glu | Asp | Tyr | Tyr | Trp | Ser | Val | Gly | Ala | Asn | Ala | Val | Phe | Gly | Val | Gln | |
| | | | 290 | | | | | 295 | | | | | 300 | | | |

| | | | | | | | | | | | | | | | | |
|---|---|---|---|---|---|---|---|---|---|---|---|---|---|---|---|---|
| CCT | ACT | TTT | GAA | GGT | ACG | TCT | ATG | GGT | TCT | TAT | GAT | GCT | ACA | TTC | TTG | 2289 |
| Pro | Thr | Phe 305 | Glu | Gly | Thr | Ser | Met 310 | Gly | Ser | Tyr | Asp | Ala 315 | Thr | Phe | Leu | |
| GAA | GAT | TCG | TAC | AAC | ACA | GTG | AAC | TCT | ATT | ATG | TGG | GCA | GGT | AAT | CTT | 2337 |
| Glu | Asp | Ser 320 | Tyr | Asn | Thr | Val 325 | Asn | Ser | Ile | Met | Trp 330 | Ala | Gly | Asn | Leu | |
| GCT | GCT | ACT | CAT | GCC | GAA | AAT | ATC | GGC | AAT | GTT | ACC | CAT | ATC | GGT | GCT | 2385 |
| Ala 335 | Ala | Thr | His | Ala 340 | Glu | Asn | Ile | Gly | Asn 345 | Val | Thr | His | Ile | Gly 350 | Ala | |
| CAT | TAC | TAT | TGG | GAA | GCT | TAT | CAT | GTC | CTT | GGC | GAT | GGT | TCG | GTT | ATG | 2433 |
| His | Tyr | Tyr | Trp | Glu 355 | Ala | Tyr | His | Val | Leu 360 | Gly | Asp | Gly | Ser | Val 365 | Met | |
| CCT | TAT | CGT | GCA | ATG | CCT | AAG | ACC | AAT | ACT | TAT | ACG | CTT | CCT | GCT | TCT | 2481 |
| Pro | Tyr | Arg | Ala 370 | Met | Pro | Lys | Thr | Asn 375 | Thr | Tyr | Thr | Leu | Pro 380 | Ala | Ser | |
| CTG | CCT | CAG | AAT | CAG | GCT | TCT | TAT | AGC | ATT | CAG | GCT | TCT | GCC | GGT | TCT | 2529 |
| Leu | Pro | Gln | Asn 385 | Gln | Ala | Ser | Tyr | Ser 390 | Ile | Gln | Ala | Ser | Ala 395 | Gly | Ser | |
| TAC | GTA | GCT | ATT | TCT | AAA | GAT | GGA | GTT | TTG | TAT | GGA | ACA | GGT | GTT | GCT | 2577 |
| Tyr | Val | Ala | Ile 400 | Ser | Lys | Asp | Gly | Val 405 | Leu | Tyr | Gly | Thr | Gly 410 | Val | Ala | |
| AAT | GCC | AGC | GGT | GTT | GCG | ACT | GTG | AAT | ATG | ACT | AAG | CAG | ATT | ACG | GAA | 2625 |
| Asn 415 | Ala | Ser | Gly | Val | Ala 420 | Thr | Val | Asn | Met | Thr 425 | Lys | Gln | Ile | Thr | Glu 430 | |
| AAT | GGT | AAT | TAT | GAT | GTA | GTT | ATC | ACT | CGC | TCT | AAT | TAT | CTT | CCT | GTG | 2673 |
| Asn | Gly | Asn | Tyr | Asp 435 | Val | Val | Ile | Thr | Arg 440 | Ser | Asn | Tyr | Leu | Pro 445 | Val | |
| ATC | AAG | CAA | ATT | CAG | GCA | GGA | GAG | CCT | AGC | CCC | TAC | CAG | CCT | GTT | TCC | 2721 |
| Ile | Lys | Gln | Ile 450 | Gln | Ala | Gly | Glu | Pro 455 | Ser | Pro | Tyr | Gln | Pro 460 | Val | Ser | |
| AAC | TTG | ACT | GCT | ACA | ACG | CAG | GGT | CAG | AAA | GTA | ACG | CTC | AAG | TGG | GAT | 2769 |
| Asn | Leu | Thr 465 | Ala | Thr | Thr | Gln | Gly 470 | Gln | Lys | Val | Thr | Leu 475 | Lys | Trp | Asp | |
| GCC | CCG | AGC | GCA | AAG | AAG | GCA | GAA | GGT | TCC | CGT | GAA | GTA | AAA | CGG | ATC | 2817 |
| Ala | Pro | Ser 480 | Ala | Lys | Lys | Ala | Glu 485 | Gly | Ser | Arg | Glu | Val 490 | Lys | Arg | Ile | |
| GGA | GAC | GGT | CTT | TTC | GTT | ACG | ATC | GAA | CCT | GCA | AAC | GAT | GTA | CGT | GCC | 2865 |
| Gly | Asp | Gly | Leu | Phe 500 | Val | Thr | Ile | Glu | Pro 505 | Ala | Asn | Asp | Val | Arg 510 | Ala | |
| Gly 495 | | | | | | | | | | | | | | | | |
| AAC | GAA | GCC | AAG | GTT | GTG | CTC | GCA | GCA | GAC | AAC | GTA | TGG | GGA | GAC | AAT | 2913 |
| Asn | Glu | Ala | Lys | Val 515 | Val | Leu | Ala | Ala | Asp 520 | Asn | Val | Trp | Gly | Asp 525 | Asn | |
| ACG | GGT | TAC | CAG | TTC | TTG | TTG | GAT | GCC | GAT | CAC | AAT | ACA | TTC | GGA | AGT | 2961 |
| Thr | Gly | Tyr | Gln | Phe 530 | Leu | Leu | Asp | Ala | Asp 535 | His | Asn | Thr | Phe | Gly 540 | Ser | |
| GTC | ATT | CCG | GCA | ACC | GGT | CCT | CTC | TTT | ACC | GGA | ACA | GCT | TCT | TCC | AAT | 3009 |
| Val | Ile | Pro | Ala | Thr 545 | Gly | Pro | Leu | Phe | Thr 550 | Gly | Thr | Ala | Ser | Ser 555 | Asn | |
| CTT | TAC | AGT | GCG | AAC | TTC | GAG | TAT | TTG | ATC | CCG | GCC | AAT | GCC | GAT | CCT | 3057 |
| Leu | Tyr | Ser 560 | Ala | Asn | Phe | Glu | Tyr 565 | Leu | Ile | Pro | Ala | Asn 570 | Ala | Asp | Pro | |
| GTT | GTT | ACT | ACA | CAG | AAT | ATT | ATC | GTT | ACA | GGA | CAG | GGT | GAA | GTT | GTA | 3105 |
| Val 575 | Val | Thr | Thr | Gln | Asn 580 | Ile | Ile | Val | Thr | Gly 585 | Gln | Gly | Glu | Val | Val 590 | |
| ATC | CCC | GGT | GGT | GTT | TAC | GAC | TAT | TGC | ATT | ACG | AAC | CCG | GAA | CCT | GCA | 3153 |
| Ile | Pro | Gly | Gly | Val 595 | Tyr | Asp | Tyr | Cys | Ile 600 | Thr | Asn | Pro | Glu | Pro 605 | Ala | |
| TCC | GGA | AAG | ATG | TGG | ATC | GCA | GGA | GAT | GGA | GGC | AAC | CAG | CCT | GCA | CGT | 3201 |
| Ser | Gly | Lys | Met | Trp 610 | Ile | Ala | Gly | Asp | Gly 615 | Gly | Asn | Gln | Pro | Ala 620 | Arg | |

|  |  |  |  |  |  |  |  |  |  |  |  |  |  |  |  |
|---|---|---|---|---|---|---|---|---|---|---|---|---|---|---|---|
| TAT | GAC | GAT | TTC | ACA | TTC | GAA | GCA | GGC | AAG | AAG | TAC | ACC | TTC | ACG | ATG |
| Tyr | Asp | Asp | Phe | Thr | Phe | Glu | Ala | Gly | Lys | Lys | Tyr | Thr | Phe | Thr | Met |
|     | 625 |     |     |     |     |     | 630 |     |     |     |     | 635 |     |     |     |

3249

| CGT | CGC | GCC | GGA | ATG | GGA | GAT | GGA | ACT | GAT | ATG | GAA | GTC | GAA | GAC | GAT |
|---|---|---|---|---|---|---|---|---|---|---|---|---|---|---|---|
| Arg | Arg | Ala | Gly | Met | Gly | Asp | Gly | Thr | Asp | Met | Glu | Val | Glu | Asp | Asp |
|     | 640 |     |     |     |     |     | 645 |     |     |     |     | 650 |     |     |     |

3297

| TCA | CCT | GCA | AGC | TAT | ACC | TAC | ACG | GTG | TAT | CGT | GAC | GGC | ACG | AAG | ATC |
|---|---|---|---|---|---|---|---|---|---|---|---|---|---|---|---|
| Ser | Pro | Ala | Ser | Tyr | Thr | Tyr | Thr | Val | Tyr | Arg | Asp | Gly | Thr | Lys | Ile |
| 655 |     |     |     |     | 660 |     |     |     |     | 665 |     |     |     |     | 670 |

3345

| AAG | GAA | GGT | CTG | ACG | GCT | ACG | ACA | TTC | GAA | GAA | GAC | GGT | GTA | GCT | GCA |
|---|---|---|---|---|---|---|---|---|---|---|---|---|---|---|---|
| Lys | Glu | Gly | Leu | Thr | Ala | Thr | Thr | Phe | Glu | Glu | Asp | Gly | Val | Ala | Ala |
|     |     |     |     | 675 |     |     |     |     | 680 |     |     |     |     | 685 |     |

3393

| GGC | AAT | CAT | GAG | TAT | TGC | GTG | GAA | GTT | AAG | TAC | ACA | GCC | GGC | GTA | TCT |
|---|---|---|---|---|---|---|---|---|---|---|---|---|---|---|---|
| Gly | Asn | His | Glu | Tyr | Cys | Val | Glu | Val | Lys | Tyr | Thr | Ala | Gly | Val | Ser |
|     |     |     | 690 |     |     |     |     | 695 |     |     |     |     | 700 |     |     |

3441

| CCG | AAG | GTA | TGT | AAA | GAC | GTT | ACG | GTA | GAA | GGA | TCC |
|---|---|---|---|---|---|---|---|---|---|---|---|
| Pro | Lys | Val | Cys | Lys | Asp | Val | Thr | Val | Glu | Gly | Ser |
|     |     | 705 |     |     |     |     | 710 |     |     |     |     |

3477

( 2 ) INFORMATION FOR SEQ ID NO:14:

( i ) SEQUENCE CHARACTERISTICS:
        ( A ) LENGTH: 942 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

```
Met Arg Lys Leu Leu Leu Leu Ile Ala Ala Ser Leu Leu Gly Val Gly
-228          -225              -220              -215

Leu Tyr Ala Gln Asn Ala Lys Ile Lys Leu Asp Ala Pro Thr Thr Arg
         -210              -205              -200

Thr Thr Cys Thr Asn Asn Ser Phe Lys Gln Phe Asp Ala Ser Phe Ser
         -195              -190              -185

Phe Asn Glu Val Glu Leu Thr Lys Val Glu Thr Lys Gly Gly Thr Phe
-180              -175              -170                      -165

Ala Ser Val Ser Ile Pro Gly Ala Phe Pro Thr Gly Glu Val Gly Ser
             -160              -155                      -150

Pro Glu Val Pro Ala Val Arg Lys Leu Ile Ala Val Pro Val Gly Ala
         -145              -140                      -135

Thr Pro Val Val Arg Val Lys Ser Phe Thr Glu Gln Val Tyr Ser Leu
         -130              -125                      -120

Asn Gln Tyr Gly Ser Glu Lys Leu Met Pro His Gln Pro Ser Met Ser
    -115              -110                      -105

Lys Ser Asp Asp Pro Glu Lys Val Pro Phe Ala Tyr Asn Ala Ala Ala
-100              -95               -90                        -85

Tyr Ala Arg Lys Gly Phe Val Gly Gln Glu Leu Thr Gln Val Glu Met
         -80                -75                       -70

Leu Gly Thr Met Arg Gly Val Arg Ile Ala Ala Leu Thr Ile Asn Pro
             -65                -60                       -55

Val Gln Tyr Asp Val Val Ala Asn Gln Leu Lys Val Arg Asn Asn Ile
             -50                -45                -40

Glu Ile Glu Val Ser Phe Gln Gly Ala Asp Glu Val Ala Thr Gln Arg
    -35                -30                -25

Leu Tyr Asp Ala Ser Phe Ser Pro Tyr Phe Glu Thr Ala Tyr Lys Gln
-20                -15                -10                     -5

Leu Phe Asn Arg Asp Val Tyr Thr Asp His Gly Asp Leu Tyr Asn Thr
        1                  5                      10
```

```
Pro Val Arg Met Leu Val Val Ala Gly Ala Lys Phe Lys Glu Ala Leu
     15                  20                  25
Lys Pro Trp Leu Thr Trp Lys Ala Gln Lys Gly Phe Tyr Leu Asp Val
     30                  35                  40
His Tyr Thr Asp Glu Ala Glu Val Gly Thr Thr Asn Ala Ser Ile Lys
 45                  50                  55                   60
Ala Phe Ile His Lys Lys Tyr Asn Asp Gly Leu Ala Ala Ser Ala Ala
             65                  70                  75
Pro Val Phe Leu Ala Leu Val Gly Asp Thr Asp Val Ile Ser Gly Glu
             80                  85                  90
Lys Gly Lys Lys Thr Lys Lys Val Thr Asp Leu Tyr Tyr Ser Ala Val
         95                 100                 105
Asp Gly Asp Tyr Phe Pro Glu Met Tyr Thr Phe Arg Met Ser Ala Ser
    110                 115                 120
Ser Pro Glu Glu Leu Thr Asn Ile Ile Asp Lys Val Leu Met Tyr Glu
125                 130                 135                 140
Lys Ala Thr Met Pro Asp Lys Ser Tyr Leu Glu Lys Ala Leu Leu Ile
                145                 150                 155
Ala Gly Ala Asp Ser Tyr Trp Asn Pro Lys Ile Gly Gln Gln Thr Ile
            160                 165                 170
Lys Tyr Ala Val Gln Tyr Tyr Asn Gln Asp His Gly Tyr Thr Asp
        175                 180                 185
Val Tyr Ser Tyr Pro Lys Ala Pro Tyr Thr Gly Cys Tyr Ser His Leu
    190                 195                 200
Asn Thr Gly Val Gly Phe Ala Asn Tyr Thr Ala His Gly Ser Glu Thr
205                 210                 215                 220
Ser Trp Ala Asp Pro Ser Val Thr Ala Thr Gln Val Lys Ala Leu Thr
                225                 230                 235
Asn Lys Asn Lys Tyr Phe Leu Ala Ile Gly Asn Cys Cys Val Thr Ala
            240                 245                 250
Gln Phe Asp Tyr Pro Gln Pro Cys Phe Gly Glu Val Met Thr Arg Val
        255                 260                 265
Lys Glu Lys Gly Ala Tyr Ala Tyr Ile Gly Ser Ser Pro Asn Ser Tyr
    270                 275                 280
Trp Gly Glu Asp Tyr Tyr Trp Ser Val Gly Ala Asn Ala Val Phe Gly
285                 290                 295                 300
Val Gln Pro Thr Phe Glu Gly Thr Ser Met Gly Ser Tyr Asp Ala Thr
                305                 310                 315
Phe Leu Glu Asp Ser Tyr Asn Thr Val Asn Ser Ile Met Trp Ala Gly
            320                 325                 330
Asn Leu Ala Ala Thr His Ala Glu Asn Ile Gly Asn Val Thr His Ile
        335                 340                 345
Gly Ala His Tyr Tyr Trp Glu Ala Tyr His Val Leu Gly Asp Gly Ser
    350                 355                 360
Val Met Pro Tyr Arg Ala Met Pro Lys Thr Asn Thr Tyr Thr Leu Pro
365                 370                 375                 380
Ala Ser Leu Pro Gln Asn Gln Ala Ser Tyr Ser Ile Gln Ala Ser Ala
                385                 390                 395
Gly Ser Tyr Val Ala Ile Ser Lys Asp Gly Val Leu Tyr Gly Thr Gly
            400                 405                 410
Val Ala Asn Ala Ser Gly Val Ala Thr Val Asn Met Thr Lys Gln Ile
        415                 420                 425
Thr Glu Asn Gly Asn Tyr Asp Val Val Ile Thr Arg Ser Asn Tyr Leu
```

|     |     |     | 430 |     |     |     |     | 435 |     |     |     |     | 440 |     |
|-----|-----|-----|-----|-----|-----|-----|-----|-----|-----|-----|-----|-----|-----|-----|

Pro Val Ile Lys Gln Ile Gln Ala Gly Glu Pro Ser Pro Tyr Gln Pro
445                     450                     455                     460

Val Ser Asn Leu Thr Ala Thr Thr Gln Gly Gln Lys Val Thr Leu Lys
                465                     470                     475

Trp Asp Ala Pro Ser Ala Lys Lys Ala Glu Gly Ser Arg Glu Val Lys
            480                     485                     490

Arg Ile Gly Asp Gly Leu Phe Val Thr Ile Glu Pro Ala Asn Asp Val
        495                     500                     505

Arg Ala Asn Glu Ala Lys Val Val Leu Ala Ala Asp Asn Val Trp Gly
    510                     515                     520

Asp Asn Thr Gly Tyr Gln Phe Leu Leu Asp Ala Asp His Asn Thr Phe
525                     530                     535                     540

Gly Ser Val Ile Pro Ala Thr Gly Pro Leu Phe Thr Gly Thr Ala Ser
                545                     550                     555

Ser Asn Leu Tyr Ser Ala Asn Phe Glu Tyr Leu Ile Pro Ala Asn Ala
            560                     565                     570

Asp Pro Val Val Thr Thr Gln Asn Ile Ile Val Thr Gly Gln Gly Glu
        575                     580                     585

Val Val Ile Pro Gly Gly Val Tyr Asp Tyr Cys Ile Thr Asn Pro Glu
    590                     595                     600

Pro Ala Ser Gly Lys Met Trp Ile Ala Gly Asp Gly Gly Asn Gln Pro
605                     610                     615                     620

Ala Arg Tyr Asp Asp Phe Thr Phe Glu Ala Gly Lys Lys Tyr Thr Phe
                625                     630                     635

Thr Met Arg Arg Ala Gly Met Gly Asp Gly Thr Asp Met Glu Val Glu
            640                     645                     650

Asp Asp Ser Pro Ala Ser Tyr Thr Tyr Thr Val Tyr Arg Asp Gly Thr
        655                     660                     665

Lys Ile Lys Glu Gly Leu Thr Ala Thr Thr Phe Glu Glu Asp Gly Val
    670                     675                     680

Ala Ala Gly Asn His Glu Tyr Cys Val Glu Val Lys Tyr Thr Ala Gly
685                     690                     695                     700

Val Ser Pro Lys Val Cys Lys Asp Val Thr Val Glu Gly Ser
                705                     710

( 2 ) INFORMATION FOR SEQ ID NO:15:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (other nucleic acid)

( i i i ) HYPOTHETICAL: NO ( i v ) ANTI-SENSE: NO ( x i ) SEQUENCE DESCRIPTION: SEQ ID NO:15:

AGATCTGAAT TCGA Y GTNTA Y ACN-GA Y CA        29

( 2 ) INFORMATION FOR SEQ ID NO:16:

( i ) SEQUENCE CHARACTERISTICS:
        ( A ) LENGTH: 29 base pairs
        ( B ) TYPE: nucleic acid
        ( C ) STRANDEDNESS: single ( D ) TOPOLOGY: linear ( i i ) MOLECULE TYPE: DNA (other nucleic acid)

( i i i ) HYPOTHETICAL: NO ( i v ) ANTI-SENSE: NO ( x i ) SEQUENCE DESCRIPTION: SEQ ID NO:16:

AGATCTAAGC TTCCNGCNAC NACNARCAT             29

( 2 ) INFORMATION FOR SEQ ID NO:17:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( i i ) MOLECULE TYPE: DNA (other nucleic acid)

( i i i ) HYPOTHETICAL: NO ( i v ) ANTI-SENSE: NO ( x i ) SEQUENCE DESCRIPTION: SEQ ID NO:17:

CATACGAACC GGCGTATTAT ACAAGTCGCC ATG             33

( 2 ) INFORMATION FOR SEQ ID NO:18:

( i ) SEQUENCE CHARACTERISTICS:
( A ) LENGTH: 24 amino acids
( B ) TYPE: amino acid
( C ) STRANDEDNESS: single
( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( v i ) ORIGINAL SOURCE:
( A ) ORGANISM: Porphyromonas gingivalis
( B ) STRAIN: H66

( x i ) SEQUENCE DESCRIPTION: SEQ ID NO:18:

His Ala Glu Asn Ile Gly Asn Val Thr His Ile Gly Ala His Tyr Tyr
1               5                   10                  15

Trp Glu Ala Tyr His Val Leu Gly
            20

( 2 ) INFORMATION FOR SEQ ID NO:19:

( i ) SEQUENCE CHARACTERISTICS:
( A ) LENGTH: 24 amino acids
( B ) TYPE: amino acid
( C ) STRANDEDNESS: single
( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( x i ) SEQUENCE DESCRIPTION: SEQ ID NO:19:

His Ala Tyr Thr Val Leu Gly Tyr Thr Val Ser Asn Gly Ala Tyr Tyr

```
               1               5                   10                  15
          Leu Ile Ile Arg Asn Pro Trp Gly
                           20
```

(2) INFORMATION FOR SEQ ID NO:20:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: internal (xi) SEQUENCE DESCRIPTION: SEQ ID NO:20:

```
     His Ala Val Thr Ala Val Gly Tyr Gly Lys Ser Gly Gly Lys Gly Tyr
     1               5                   10                  15

Ile Leu Ile Lys Asn Ser Trp Gly
                     20
```

(2) INFORMATION FOR SEQ ID NO:21:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: internal (xi) SEQUENCE DESCRIPTION: SEQ ID NO:21:

```
     His Ala Val Leu Ala Val Gly Tyr Gly Glu Gln Asn Gly Leu Leu Tyr
     1               5                   10                  15

Trp Ile Val Lys Asn Ser Trp Gly
                     20
```

(2) INFORMATION FOR SEQ ID NO:22:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: internal (xi) SEQUENCE DESCRIPTION: SEQ ID NO:22:

```
     His Ala Val Asn Ile Val Gly Tyr Ser Asn Ala Gln Gly Val Asp Tyr
     1               5                   10                  15

Trp Ile Val Arg Asn Ser Trp Asp
                     20
```

( 2 ) INFORMATION FOR SEQ ID NO:23:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( x i ) SEQUENCE DESCRIPTION: SEQ ID NO:23:

```
Gly Cys Val Thr Ala Val Gly Tyr Gly Ser Asn Ser Asn Gly Lys Tyr
 1               5                   10                  15
Trp Ile Val Lys Asn Ser Trp
            20
```

( 2 ) INFORMATION FOR SEQ ID NO:24:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( x i ) SEQUENCE DESCRIPTION: SEQ ID NO:24:

```
His Gly Val Leu Leu Val Gly Tyr Asn Asp Asn Ser Asn Pro Pro Tyr
 1               5                   10                  15
Trp Ile Val Lys Asn Ser Trp
            20
```

( 2 ) INFORMATION FOR SEQ ID NO:25:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( x i ) SEQUENCE DESCRIPTION: SEQ ID NO:25:

```
Gly Gly Leu Leu Leu Val Gly Tyr Asn Asp Ser Ala Ala Val Pro Tyr
 1               5                   10                  15
Trp Ile Ile Lys Asn Ser Trp
            20
```

( 2 ) INFORMATION FOR SEQ ID NO:26:

( i ) SEQUENCE CHARACTERISTICS:
        ( A ) LENGTH: 24 amino acids (B) TYPE: amino acid
          (C) STRANDEDNESS: single
          (D) TOPOLOGY: linear (ii) MOLECULE TYPE: protein (iii) HYPOTHETICAL: NO (iv) ANTI-SENSE: NO (v) FRAGMENT TYPE: internal (xi) SEQUENCE DESCRIPTION: SEQ ID NO:26:

His Ala Ile Val Ile Val Gly Tyr Gly Thr Glu Gly Gly Val Asp Tyr
    1               5                   10                  15

Trp Ile Val Lys Asn Ser Trp Asp
                20

(2) INFORMATION FOR SEQ ID NO:27:

(i) SEQUENCE CHARACTERISTICS:
          (A) LENGTH: 24 amino acids
          (B) TYPE: amino acid
          (C) STRANDEDNESS: single
          (D) TOPOLOGY: linear (ii) MOLECULE TYPE: protein (iii) HYPOTHETICAL: NO (iv) ANTI-SENSE: NO (v) FRAGMENT TYPE: internal (xi) SEQUENCE DESCRIPTION: SEQ ID NO:27:

His Ala Ile Arg Ile Leu Gly Trp Gly Val Glu Asn Gly Thr Pro Tyr
    1               5                   10                  15

Trp Leu Val Ala Asn Ser Trp Asn
                20

(2) INFORMATION FOR SEQ ID NO:28:

(i) SEQUENCE CHARACTERISTICS:
          (A) LENGTH: 20 amino acids
          (B) TYPE: amino acid
          (C) STRANDEDNESS: single
          (D) TOPOLOGY: linear (ii) MOLECULE TYPE: protein (iii) HYPOTHETICAL: NO (iv) ANTI-SENSE: NO (v) FRAGMENT TYPE: internal (xi) SEQUENCE DESCRIPTION: SEQ ID NO:28:

His Ala Val Ala Ala Val Gly Tyr Asn Pro Gly Tyr Ile Leu Val Lys
    1               5                   10                  15

Asn Ser Trp Gly
                20